United States Patent
Gray et al.

(10) Patent No.: US 10,544,138 B2
(45) Date of Patent: Jan. 28, 2020

(54) TRICYCLIC KINASE INHIBITORS OF MELK AND METHODS OF USE

(71) Applicant: Dana-Farber Cancer Institute, Inc., Boston, MA (US)

(72) Inventors: Nathanael Gray, Boston, MA (US); Tinghu Zhang, Brookline, MA (US); Hai-Tsang Huang, Boston, MA (US); Yubao Wang, Newton, MA (US); Jean Zhao, Brookline, MA (US); Hwan Geun Choi, Seoul (KR)

(73) Assignee: Dana-Farber Cancer Institute, Inc., Boston, MA (US)

(*) Notice: Subject to any disclaimer, the term of this patent is extended or adjusted under 35 U.S.C. 154(b) by 0 days.

(21) Appl. No.: 15/554,595

(22) PCT Filed: Mar. 4, 2016

(86) PCT No.: PCT/US2016/020904
§ 371 (c)(1),
(2) Date: Aug. 30, 2017

(87) PCT Pub. No.: WO2016/141296
PCT Pub. Date: Sep. 9, 2016

(65) Prior Publication Data
US 2019/0084977 A1    Mar. 21, 2019

Related U.S. Application Data

(60) Provisional application No. 62/128,261, filed on Mar. 4, 2015.

(51) Int. Cl.
| | | |
|---|---|---|
| *C07D 471/04* | (2006.01) | |
| *A61K 31/337* | (2006.01) | |
| *A61K 31/4745* | (2006.01) | |
| *A61P 35/00* | (2006.01) | |
| *A61K 31/519* | (2006.01) | |

(52) U.S. Cl.
CPC .......... *C07D 471/04* (2013.01); *A61K 31/337* (2013.01); *A61K 31/4745* (2013.01); *A61K 31/519* (2013.01); *A61P 35/00* (2018.01)

(58) Field of Classification Search
None
See application file for complete search history.

(56) References Cited

U.S. PATENT DOCUMENTS 8,889,706 B2 * 11/2014 Gray ............... C07D 471/04
514/292
2008/0194579 A1    8/2008 Garcia-Echeverria et al.
2011/0190326 A1    8/2011 Cheng et al.

FOREIGN PATENT DOCUMENTS

| WO | WO-2009/152027 A1 | 12/2009 | |
|---|---|---|---|
| WO | WO-2010/044885 A2 | 4/2010 | |
| WO | WO-2011/011716 A1 | 1/2011 | |
| WO | WO-2011/035019 A1 | 3/2011 | |
| WO | WO-2012/007926 A1 | 1/2012 | |
| WO | WO-2012/016082 A1 | 2/2012 | |
| WO | WO-2013/071698 A1 | 5/2013 | |
| WO | WO-2013/109388 A2 | 7/2013 | |
| WO | WO-2015073804 A2 * | 5/2015 | ......... A61K 31/4353 |

OTHER PUBLICATIONS

Extended European Search Report for European Application No. EP 16759581 dated Oct. 10, 2018.
International Search Report and Written Opinion for International Application No. PCT/US16/20904 dated May 17, 2016.
Liu et al., "Discovery of 1-(4-(4-Propionylpiperazin-1-yl)-3-(trifluoromethyl)phenyl)-9-(quinolin-3-yl)benzo[h][1,6] naphthyridin-2(1 H)—one as a Highly Potent, Selective Mammalian Target of Rapamycin (mTOR) Inhibitor for the Treatment of Cancer," Journal of Medicinal Chemistry, 53(19):7146-7155 (2010).
Ganguly et al., "Maternal Embryonic Leucine Zipper Kinase: Key Kinase for Stem Cell Phenotype in Glioma and Other Cancers," Mole Canc Therapeut 13(6):1393-1398 (2014).

* cited by examiner

*Primary Examiner* — Heidi Reese
(74) *Attorney, Agent, or Firm* — Foley Hoag LLP

(57) ABSTRACT

Provided herein are tricyclic small molecule inhibitors of maternal embryonic leucine zipper kinase (MELK). The compounds are useful for treating cancer and other conditions or diseases associated with aberrant MELK expression. Also provided herein are pharmaceutical compositions comprising a tricyclic compound of the invention and a pharmaceutically acceptable carrier. The invention also provides methods of treating cancers associated with over-expression of MELK.

20 Claims, 22 Drawing Sheets

Specification includes a Sequence Listing.

F

TRICYCLIC KINASE INHIBITORS OF MELK AND METHODS OF USE

RELATED APPLICATIONS

This application is the United States National Stage application of PCT/US2016/020904, filed Mar. 4, 2016, which claims the benefit of priority to U.S. Provisional Patent Application Ser. No. 62/128,261, filed Mar. 4, 2015, the contents of which are hereby incorporated by reference.

SEQUENCE LISTING

The instant application contains a Sequence Listing which has been filed electronically in ASCII format and is hereby incorporated by reference in its entirety. Said ASCII copy, created on Oct. 29, 2018, is named DFS-15001_SL.txt and is 1,348 bytes in size.

GOVERNMENT SUPPORT

This invention was made with government support under grant number P50CA168504 awarded by The National Institutes of Health. The government has certain rights in the invention.

BACKGROUND

Despite marked advances in the diagnosis and treatment of breast cancer, patients with basal-like breast cancer (BBC), an aggressive subtype of breast cancer, continue to be confronted with limited treatment options due to current lack of molecular targets in this tumor type. Therefore, the identification of a "druggable" target that is specifically required for basal-like breast tumors is one of the most pressing challenges facing cancer researchers today. The inventors recently identified maternal embryonic leucine zipper kinase (MELK), a novel oncogenic kinase that emerged from an unbiased, in vivo tumorigenesis screen, as a therapeutic target in BBC.

MELK is an atypical member of the AMPK family. While MELK has been implicated in regulating cell cycle progression, cellular proliferation, mitosis, apoptosis, and mRNA splicing (Badouel et al. (2006) *Cell Cycle* 5:883-889 and Badouel et al. (2010) *Exp. Cell Res.* 316:2166-2173), the exact function of MELK is unknown. MELK is overexpressed in a number of cancers, including cancers of the colon, breast, ovaries, pancreas, prostate, and brain (Gangulu, R., et al. (2014) *Mol. Cancer Ther.* 13(6), 1393-1398). In particular, MELK is highly overexpressed selectively in the BBC subtype. Preliminary data shows that overexpression of wild type MELK induces robust oncogenic transformation both in vitro and in vivo with a transforming potency comparable to that of a highly oncogenic mutant allele of PIK3CA. Even more striking is the finding that only human BBC cells, but not luminal breast cancer cells or normal non-cancerous cells, depend on MELK for proliferation. Notably, the kinase activity of MELK is required for its transforming activity as well as for the survival and proliferation of BBC cells. Thus, MELK is potentially a novel oncogenic driver of basal-like breast carcinoma and a promising target for small molecule-based therapeutic intervention.

Because overexpression of MELK has been associated with a number of cancers, there remains a need to develop small molecule-based therapeutic agents that target MELK and that can be used in the treatment of cancers such as BBC that are specifically dependent on MELK. There also remains a need to develop preclinical models for evaluating the efficacy of candidate therapeutic agents against MELK in vivo, and for assessing on-target effects and side-effects of systemic loss of MELK in vivo.

SUMMARY OF THE INVENTION

The invention described herein provides compounds of formula (I), or pharmaceutically acceptable salts thereof:

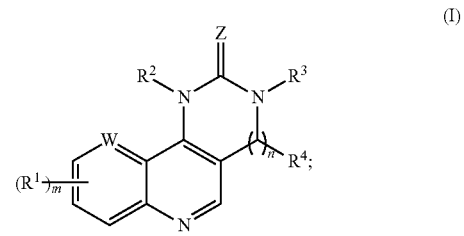

(I)

wherein:
Z represents O, S, NH, or N(alkyl);
$R^1$, independently for each occurrence, represents substituted or unsubstituted aryl or heteroaryl;
$R^2$ represents aryl, aralkyl, heteroaryl, heteroaralkyl, cycloalkyl, cycloalkylalkyl, heterocycloalkyl, or heterocycloalkylalkyl, optionally substituted by one or more occurrences of substituent $R^5$;
$R^3$ and $R^4$ are each independently selected from the group consisting of H, alkyl, aralkyl, and aryl;
$R^5$, independently for each occurrence, is selected from the group consisting of substituted or unsubstituted alkyl, alkenyl, alkynyl, halo, haloalkyl, alkoxyl, amino, aminoalkyl, hydroxy, hydroxyalkyl, aryl, aryloxy, arylalkoxy, heteroaryl, heteroaryloxy, heteroarylalkoxy, cyano, nitro, cycloalkyl, and heterocycloalkyl;
W represents N, CH, or $CR^1$;
m is an integer from 1-3; and
n is 0 or 1.

The invention described herein also provides compounds of formula (IV) and pharmaceutically acceptable salts thereof,

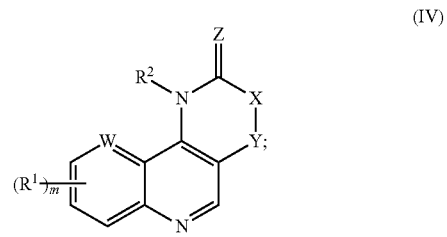

(IV)

wherein:
Z represents O, S, NH, or N(alkyl);
—X—Y— represents —$CR^3$=$CR^4$— or —$CHR^3$—$CHR^4$—;
$R^1$, independently for each occurrence, represents aryl, substituted by one or more substituents $R^x$, which, independently for each occurrence, is selected from the group consisting of halo, ($C_1$-$C_6$)alkyl, ($C_1$-$C_6$)alkenyl, ($C_1$-$C_6$)alkynyl, ($C_1$-$C_6$)haloalkyl, aryl, —OH, ($C_3$-$C_6$) cycloalkyl, ($C_1$-$C_6$)alkoxyl, ($C_1$-$C_6$)haloalkoxyl, —SH, —S(($C_1$-$C_6$)alkyl), ($C_1$-$C_6$)hydroxyalkyl, ($C_1$-$C_6$)alkoxy($C_1$-$C_6$)alkyl, —CN, —$CF_3$, —$NO_2$, —$NH_2$, —NH($R^6$), —N($R^6$)$_2$, ($C_1$-$C_6$)alkyl substituted by —N($R^6$)$_2$, —C(O)$NH_2$, —C(O)NH($R^6$), —C(O)N($R^6$)$_2$, —N(H)C(O)($R^6$), —N($R^6$)C(O)($R^6$), —S(O)$_2$$NH_2$, —S(O)$_2$NH($R^6$), —S(O)$_2$N($R^6$)$_2$, —N(H)S(O)$_2$($R^6$), and —N($R^6$)S(O)$_2$($R^6$);

wherein at least one occurrence of $R^x$ is OH;

$R^2$ represents aryl, aralkyl, heteroaryl, heteroaralkyl, cycloalkyl, cycloalkylalkyl, heterocycloalkyl, or heterocycloalkylalkyl, optionally substituted by one or more occurrences of substituent $R^5$;

$R^3$ and $R^4$ are each independently selected from the group consisting of H, alkyl, aralkyl, and aryl;

$R^5$, independently for each occurrence, is selected from the group consisting of substituted or unsubstituted alkyl, alkenyl, alkynyl, halo, haloalkyl, alkoxyl, amino, aminoalkyl, hydroxy, hydroxyalkyl, aryl, aryloxy, arylalkoxy, heteroaryl, heteroaryloxy, heteroarylalkoxy, cyano, nitro, cycloalkyl, and heterocycloalkyl;

$R^6$, independently for each occurrence, is selected from the group consisting of ($C_1$-$C_6$)alkyl, aryl, and aryl($C_1$-$C_6$)alkyl, or, for —N($R^6$)$_2$, —C(O)N($R^6$)$_2$, and —S(O)$_2$N($R^6$)$_2$, or two occurrences of $R^6$, together with the nitrogen atom to which they are attached can be taken together to form an optionally substituted ring;

W represents N, CH, or $CR^1$; and m is an integer from 1-3.

The invention further provides compounds of formula (V), or pharmaceutically acceptable salts thereof,

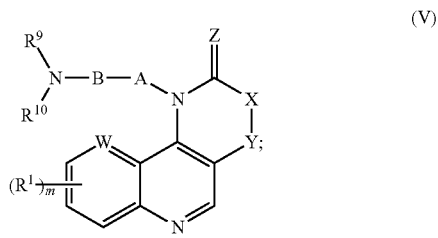

(V)

wherein:

A is represented by 1,4-cyclohexanediyl, 1,3-cyclohexanediyl, 1,2-cyclohexanediyl, 1,4-phenylene, 1,4-cycloheptanediyl, 1,3-cycloheptanediyl, 1,3-cyclooctanediyl, 1,4-cyclooctanediyl, 1,5-cyclooctanediyl;

B is represented by ($C_1$-$C_6$)alkylene or a bond; and $R^9$ and $R^{10}$ are each independently selected from the group consisting of H, ($C_1$-$C_6$)alkyl, aryl, and aryl($C_1$-$C_6$)alkyl, or, $R^9$ and $R^{10}$, together with the nitrogen atom to which they are attached can be taken together to form an optionally substituted heterocyclic ring.

The invention also relates to pharmaceutical compositions, comprising a compound of any of formulae (I), (II), (III), (IV), or (V) as described herein, and a pharmaceutically acceptable carrier.

In another aspect, the invention relates to methods of treating cancer, comprising administering to a subject in need thereof a therapeutically effective amount of a compound of any of formula (I), (II), (III), (IV), or (V) as described herein. In another aspect, the invention relates to methods for treating or preventing a condition associated with aberrant maternal embryonic leucine zipper kinase (MELK).

In another aspect, the invention relates to methods of inhibiting maternal embryonic leucine zipper kinase (MELK), comprising contacting MELK with a compound of any of formulae (I), (II), (III), (IV), or (V) as described herein in an amount effective to inhibit MELK.

In another aspect, the invention relates to methods of decreasing the rate of mitosis in a cancer cell, comprising contacting the cancer cell with a compound of any of formulae (I), (II), (III), (IV), or (V) as described herein in an amount effective to decrease the rate of mitosis of the cancer cell.

DETAILED DESCRIPTION OF THE INVENTION

Figure 1:
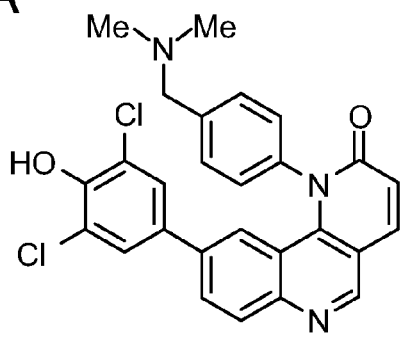
FIG. 1 shows the structure of and inhibition data for MELK inhibitor THZ-4-63-1 (also referred to herein as 01-047) and consists of Panels A, B, C, D, and E. Panel A shows the structure of THZ-4-63-1. Panel B shows graphs that demonstrate that THZ-4-63-1 preferentially targets MELK. Biomedical assays were performed with recombinant protein of the indicated mitotic kinase (left) and AMPK family kinases (right) in the presence of THZ-4-63-1. Panels C-E show that THZ-4-63-1 alters the electrophoretic mobility of mitotic MELK. Specifically, Panel C shows electrophoretic mobility of MELK in different cell cycle phase. Cells were treated with nocodazole (100 ng/ml) for 18 h or not treated (Asyn., asynchronous). Nocodazole-arrested mitotic cells (M) were isolated via shake-off. The attached cells enriched in G2 phase (G2) were harvested. A portion of the mitotic cells were washed off nocodazole and released into G1 phase after 4 hours of incubation (G1). MELK in mitotic cells exhibits the lowest electrophoretic mobility. In Panel D, mitotic lysates were prepared from the indicated cells, and treated with λ-phosphatase at 30° C. In Panel E, nocodazole-arrested mitotic cells were treated with increasing concentration of THZ-4-63-1 for 30 min. Cell lysates were subjected to immunoblotting.
Figure 1:
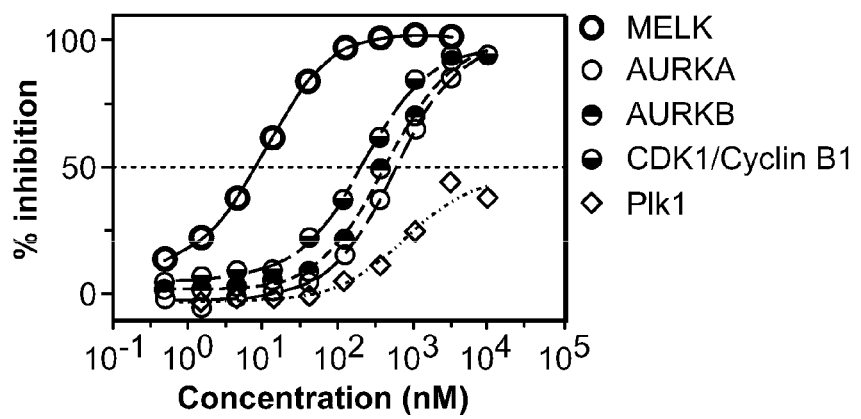
Figure 1:
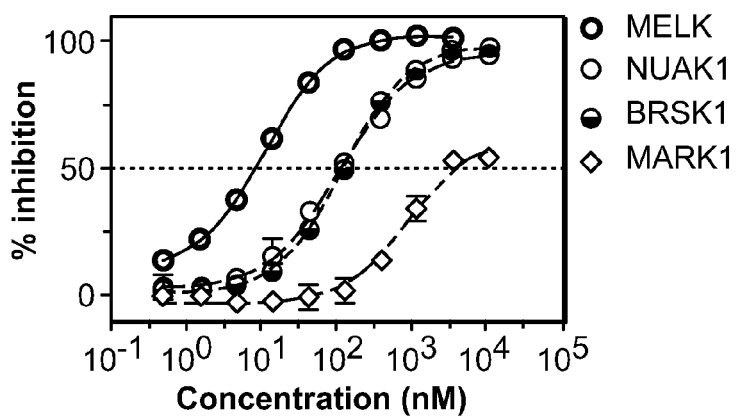
Figure 1:
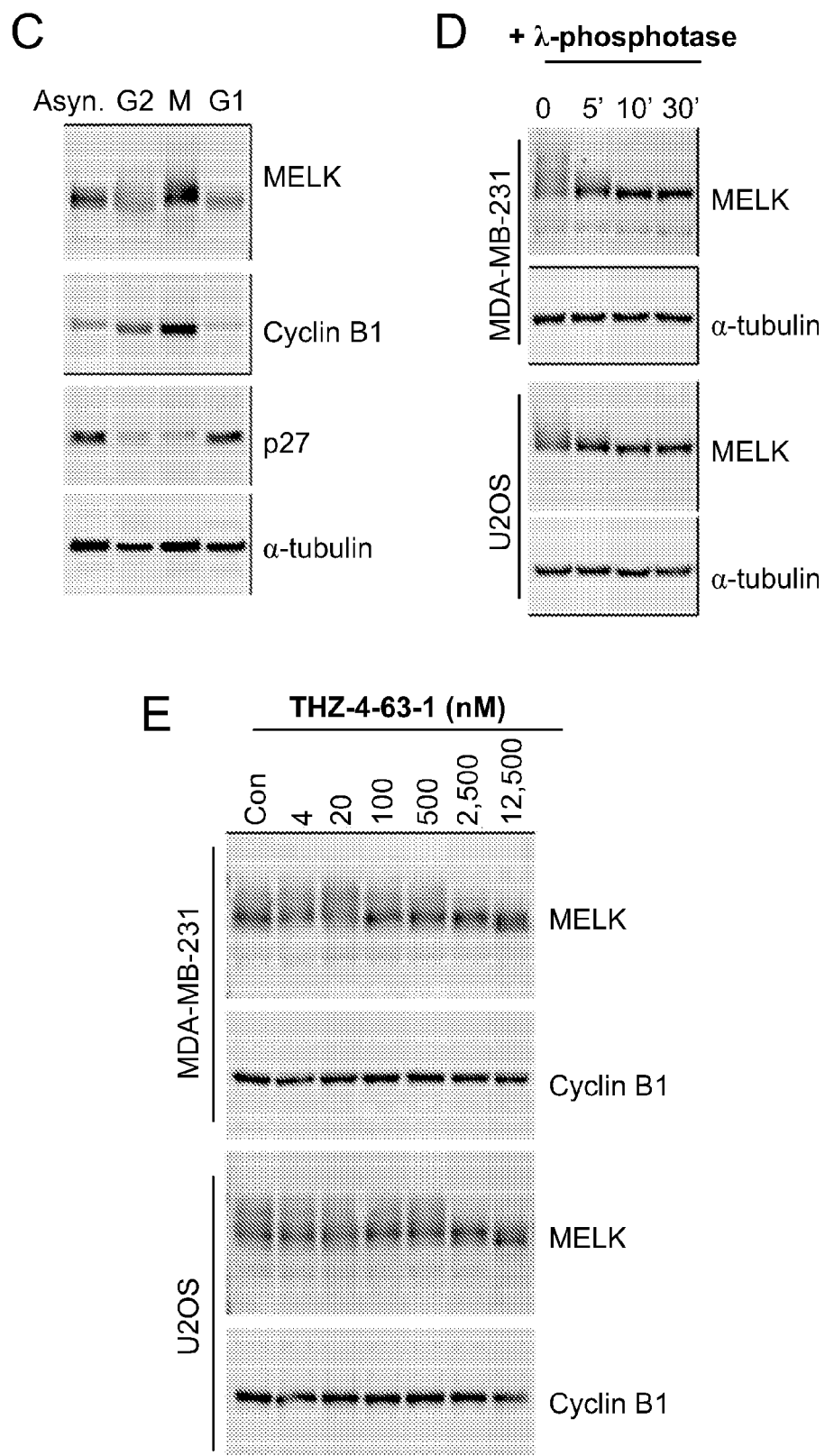

Maternal embryonic leucine zipper kinase (MELK) is an oncogenic kinase that is overexpressed in a number of cancers, including cancers of the colon, breast, ovaries, pancreas, prostate, and brain. Activation of this kinase is associated with survival and proliferation of cancer stem cells in various organs. Accordingly, inhibition of this kinase presents a therapeutic strategy for the treatment of cancers associated with MELK expression.

The present invention is based, at least in part, on the discovery of a class of small molecule compounds having inhibitory activity for MELK. These compounds exhibit suitable pharmacological properties, which facilitate their use in therapeutic applications.

I. Definitions

The articles "a" and "an" are used herein to refer to one or to more than one (i.e., to at least one) of the grammatical object of the article. By way of example, "an element" means one element or more than one element.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

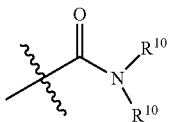

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

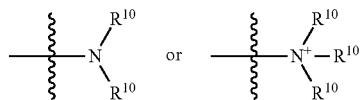

wherein each $R^{10}$ independently represents a hydrogen or a hydrocarbyl group, or two $R^{10}$ are taken together with the N atom to which they are attached complete a heterocycle having from 4 to 8 atoms in the ring structure. In certain embodiments, amine encompasses cyclic amines, including bicyclic amines. In certain embodiments, amine includes DABCO (1,4-diazabicyclo[2.2.2]octane).

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. Substituents of a substituted aryl may include any of the groups contemplated as substituents for alkyl and cycloalkyl groups, which are described herein.

The term "carbamate" is art-recognized and refers to a group

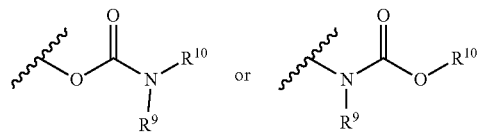

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

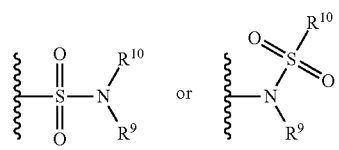

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl. In certain embodiments, the sulfoxide may be a stereogenic center. In certain such embodiments, the compounds may be enriched for one isomer of the sulfoxide.

The term "sulfonate" is art-recognized and refers to the group $SO_3H$, or a pharmaceutically acceptable salt thereof. A sulfonate ester refers to a group $—S(O)_2—OR^{10}$, wherein $R^{10}$ represents a hydrocarbyl.

The term "sulfone" is art-recognized and refers to the group $—S(O)_2—R^{10}$, wherein $R^{10}$ represents a hydrocarbyl.

The term "thioalkyl", as used herein, refers to an alkyl group substituted with a thiol group.

The term "thioester", as used herein, refers to a group $—C(O)SR^{10}$ or $—SC(O)R^{10}$ wherein $R^{10}$ represents a hydrocarbyl.

The term "thioether", as used herein, is equivalent to an ether, wherein the oxygen is replaced with a sulfur.

The term "disulfide" refers to a group $—S—S—R^{10}$, wherein $R^{10}$ represents a hydrocarbyl.

The term "urea" is art-recognized and may be represented by the general formula

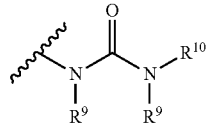

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

The term "tertiary carbon" refers to an sp$^3$-hybridized carbon atom bonded to exactly one hydrogen atom and three non-hydrogen substituents, preferably carbon-based substituents such as alkyl, alkenyl, alkynyl, aryl, aralkyl, heteroaryl, heteroaralkyl, cycloalkyl, heterocyclyl, acyl, carboxy, ester, hydroxyalkyl, haloalkyl, and the like. The term "quaternary carbon" refers to an sp$^3$-hybridized carbon atom bonded to four non-hydrogen substituents, preferably carbon-based substituents such as alkyl, alkenyl, alkynyl, aryl, aralkyl, heteroaryl heteroaralkyl, cycloalkyl, heterocyclyl, acyl, carboxy, ester, hydroxyalkyl, haloalkyl, and the like.

As used herein, "MELK" refers to the MELK member of the protein kinase superfamily and is alternatively known as "pEG3 kinase," "protein kinase Eg3," "protein kinase," and "serine/threonine-protein kinase MELK." A discussion of the splice variants encoding distinct human MELK isoforms, representative National Center for Biotechnology Information Reference Sequence numbers, and representative DNA and amino acid sequences appear in PCT/US/ 2014/065173, which is incorporated herein by reference.

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a solid tumor, but such cells may exist alone within an animal, or may be a non-tumorigenic cancer cell, such as a leukemia cell. Cancers include, but are not limited to, B cell cancer, e.g., multiple myeloma, Waldenström's marcoglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung cancer, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In certain embodiments, the cancer is associated with the overexpression of MELK. Also included are any cancers in which the gene encoding MELK is amplified or overexpressed. In certain embodiments, the cancer is breast cancer, ovarian cancer, or melanoma. In certain embodiments, the breast cancer is basal-like breast cancer (BBC).

As used herein, the term "inhibit" includes the decrease, limitation, or blockage, of, for example a particular action, function, or interaction. For example, cancer is "inhibited" if at least one symptom of the cancer, such as hyperproliferative growth, is alleviated, terminated, slowed, or prevented. As used herein, cancer is also "inhibited" if recurrence or metastasis of the cancer is reduced, slowed, delayed, or prevented. An enzyme, for example, a kinase is inhibited if a native biological function of the kinase is reduced, diminished, or stopped.

The term "modulate" includes up-regulation and down-regulation, e.g., enhancing or inhibiting a response.

The term "subject" refers to any healthy animal, mammal or human, or any animal, mammal or human afflicted with a condition of interest (e.g., cancer). The term "subject" is interchangeable with "patient." In other embodiments, the subject has breast cancer, ovarian cancer, or melanoma.

II. Compounds of the Invention

The invention provides compounds according to formula (I), or pharmaceutically acceptable salts thereof;

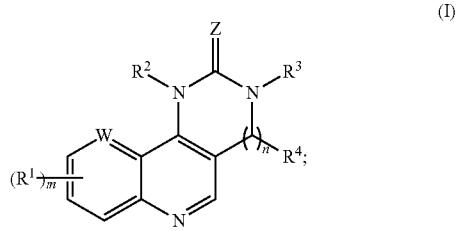

wherein:
Z represents O, S, NH, or N(alkyl);
$R^1$, independently for each occurrence, represents substituted or unsubstituted aryl or heteroaryl;
$R^2$ represents aryl, aralkyl, heteroaryl, heteroaralkyl, cycloalkyl, cycloalkylalkyl, heterocycloalkyl, or heterocycloalkylalkyl, optionally substituted by one or more occurrences of substituent $R^5$;
$R^3$ and $R^4$ are each independently selected from the group consisting of H, alkyl, aralkyl, and aryl;
$R^5$, independently for each occurrence, is selected from the group consisting of substituted or unsubstituted alkyl, alkenyl, alkynyl, halo, haloalkyl, alkoxyl, amino, aminoalkyl, hydroxy, hydroxyalkyl, aryl, aryloxy, arylalkoxy, heteroaryl, heteroaryloxy, heteroarylalkoxy, cyano, nitro, cycloalkyl, and heterocycloalkyl;

W represents N, CH, or $CR^1$;
m is an integer from 1-3; and
n is 0 or 1.

In certain embodiments, Z is O.
In certain embodiments, W is N.
In certain embodiments, W is CH.
In certain embodiments, n is 0. In certain such embodiments, $R^3$ can be H. Alternatively, $R^3$ can be $(C_1-C_6)$alkyl.
In certain embodiments, the compound of formula (I) has the structure represented by formula (II),

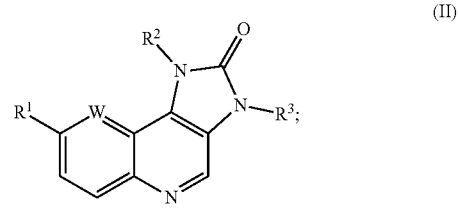

wherein:
$R^1$, independently for each occurrence, represents aryl, optionally substituted by one or more substituents selected from the group consisting of halo, $(C_1-C_6)$alkyl, $(C_1-C_6)$alkenyl, $(C_1-C_6)$alkynyl, $(C_1-C_6)$haloalkyl, aryl, —OH, $(C_3-C_6)$cycloalkyl, $(C_1-C_6)$alkoxyl, $(C_1-C_6)$haloalkoxyl, —SH, —S$((C_1-C_6)$alkyl), $(C_1-C_6)$hydroxyalkyl, $(C_1-C_6)$alkoxy$(C_1-C_6)$alkyl, —CN, —$CF_3$, —$NO_2$, —$NH_2$, —NH($R^6$), —N$(R^6)_2$, $(C_1-C_6)$alkyl substituted by —N$(R^6)_2$, —C(O)$NH_2$, —C(O)NH($R^6$), —C(O)N$(R^6)_2$, —N(H)C(O)($R^6$), —N($R^6$)C(O)($R^6$), —S$(O)_2NH_2$, —S$(O)_2$NH($R^6$), —S$(O)_2$N$(R^6)_2$, —N(H)S$(O)_2$($R^6$), and —N($R^6$)S$(O)_2$($R^6$);
wherein each occurrence of $R^6$ is independently selected from the group consisting of $(C_1-C_6)$alkyl, aryl, and aryl$(C_1-C_6)$alkyl, or, for —N$(R^6)_2$, —C(O)N$(R^6)_2$, and —S$(O)_2$N$(R^6)_2$, two occurrences of $R^6$, together with the nitrogen atom to which they are attached can be taken together to form an optionally substituted ring.

In certain embodiments, in the compound of formula (II), W is N. In alternative embodiments, W is CH.

In certain embodiments in which n is 0 (e.g., in the compound of formula (II)), $R^1$, independently for each occurrence, can represent aryl, optionally substituted by one or more substituents selected from the group consisting of $C_1-C_6$alkyl, $(C_1-C_6)$alkoxy, $(C_1-C_6)$haloalkyl, halo, —OH, $(C_1-C_6)$haloalkoxyl, —SH, —S$((C_1-C_6)$alkyl), $(C_1-C_6)$hydroxyalkyl, and —$CF_3$.

In certain embodiments, $R^1$ is

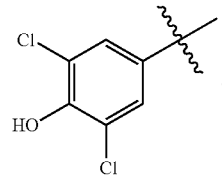

In certain embodiments in which n is 0 (e.g., in the compound of formula (II)), $R^2$ represents aryl, aralkyl, cycloalkyl, cycloalkylalkyl, heterocycloalkyl, or heterocycloalkylalkyl, optionally substituted by one or more occurrences of substituent $R^5$, wherein $R^5$ is selected from the group consisting of substituted or unsubstituted alkyl, halo, haloalkyl, amino, aminoalkyl, heteroaryl, heteroaryloxy, and heterocycloalkyl.

In certain embodiments, the compound of formula (II) is one of the following compounds, or a pharmaceutically acceptable salt thereof:

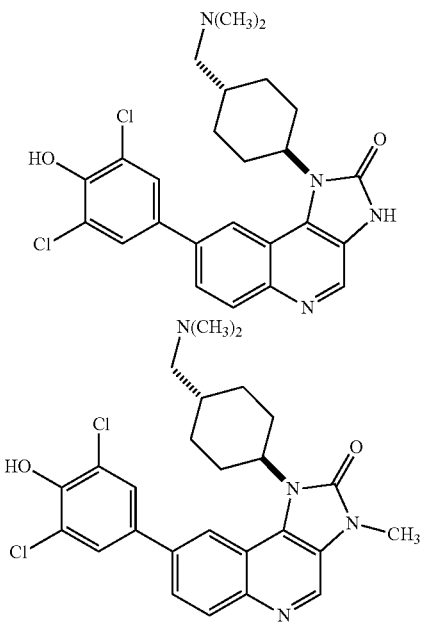

In certain embodiments, n is 1. In certain such embodiments, $R^4$ is preferably H. $R^3$ can be H, or alternatively, $R^3$ can be $(C_1-C_6)$alkyl.

In certain embodiments, the compound of formula (I) has the structure represented by formula (III),

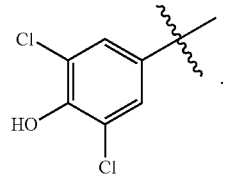

(III)

wherein:
$R^1$, independently for each occurrence, represents aryl or heteroaryl, optionally substituted by one or more substituents selected from the group consisting of halo, $(C_1-C_6)$alkyl, $(C_1-C_6)$alkenyl, $(C_1-C_6)$alkynyl, $(C_1-C_6)$haloalkyl, aryl, —OH, $(C_3-C_6)$cycloalkyl, $(C_1-C_6)$alkoxyl, $(C_1-C_6)$haloalkoxyl, —SH, —S($(C_1-C_6)$alkyl), $(C_1-C_6)$hydroxyalkyl, $(C_1-C_6)$alkoxy$(C_1-C_6)$alkyl, —CN, —CF_3, —NO_2, —NH_2, —NH($R^6$), —N($R^6$)_2, $(C_1-C_6)$alkyl substituted by —N($R^6$)_2, —C(O)NH_2, —C(O)NH($R^6$), —C(O)N($R^6$)_2, —N(H)C(O)($R^6$), —N($R^6$)C(O)($R^6$), —S(O)_2NH_2, —S(O)_2NH($R^6$), —S(O)_2N($R^6$)_2, —N(H)S(O)_2($R^6$), —N($R^6$)S(O)_2($R^6$);
wherein each occurrence of $R^6$ is independently selected from the group consisting of $(C_1-C_6)$alkyl), aryl, and aryl$(C_1-C_6)$alkyl, or, for —N($R^6$)_2, —C(O)N($R^6$)_2, and —S(O)_2N($R^6$)_2, two occurrences of $R^6$, together with the nitrogen atom to which they are attached can be taken together to form an optionally substituted ring.

In certain embodiments in which n is 1 (e.g., in the compound of formula (III)), $R^1$, independently for each occurrence, can represent aryl, optionally substituted by one or more substituents selected from the group consisting of halo, $(C_1-C_6)$alkyl, $(C_1-C_6)$alkenyl, $(C_1-C_6)$alkynyl, $(C_1-C_6)$haloalkyl, aryl, —OH, $(C_3-C_6)$cycloalkyl, $(C_1-C_6)$alkoxyl, $(C_1-C_6)$haloalkoxyl, —SH, —S($(C_1-C_6)$alkyl), $(C_1-C_6)$hydroxyalkyl, $(C_1-C_6)$alkoxy$(C_1-C_6)$alkyl, —CN, —CF_3, —NO_2, —NH_2, —NH($R^6$), —N($R^6$)_2, $(C_1-C_6)$alkyl substituted by —N($R^6$)_2, —C(O)NH_2, —C(O)NH($R^6$), —C(O)N($R^6$)_2, —N(H)C(O)($R^6$), —N($R^6$)C(O)($R^6$), —S(O)_2NH_2, —S(O)_2NH($R^6$), —S(O)_2N($R^6$)_2, —N(H)S(O)_2($R^6$), —N($R^6$)S(O)_2($R^6$);
wherein each occurrence of $R^6$ is independently selected from the group consisting of $(C_1-C_6)$alkyl), aryl, and aryl$(C_1-C_6)$alkyl, or, for —N($R^6$)_2, —C(O)N($R^6$)_2, and —S(O)_2N($R^6$)_2, two occurrences of $R^6$, together with the nitrogen atom to which they are attached can be taken together to form an optionally substituted ring.

In certain embodiments, $R^1$, independently for each occurrence, represents aryl, optionally substituted by one or more substituents selected from the group consisting of $C_1-C_6$alkyl, $(C_1-C_6)$alkoxy, $(C_1-C_6)$haloalkyl, halo, —OH, $(C_1-C_6)$haloalkoxyl, —SH, —S($(C_1-C_6)$alkyl), $(C_1-C_6)$hydroxyalkyl, and —CF_3.

In certain embodiments, $R^1$ is

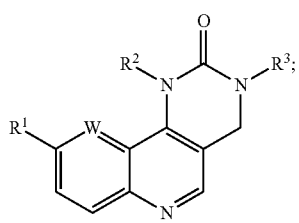

In certain embodiments, $R^2$ represents aryl, aralkyl, cycloalkyl, cycloalkylalkyl, heterocycloalkyl, or heterocycloalkylalkyl, optionally substituted by one or more occurrences of substituent $R^5$;
wherein $R^5$, independently for each occurrence, is selected from the group consisting of substituted or unsubstituted alkyl, halo, haloalkyl, amino, aminoalkyl, heteroaryl, heteroaryloxy, and heterocycloalkyl.

In certain embodiments, the compound of formula (III) is represented by one of the following structures, or a pharmaceutically acceptable salt thereof:

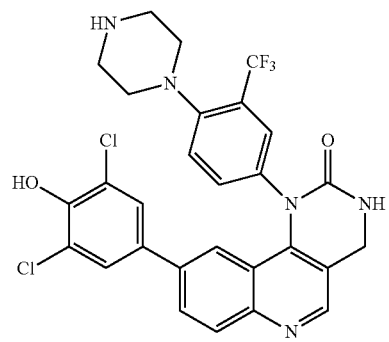

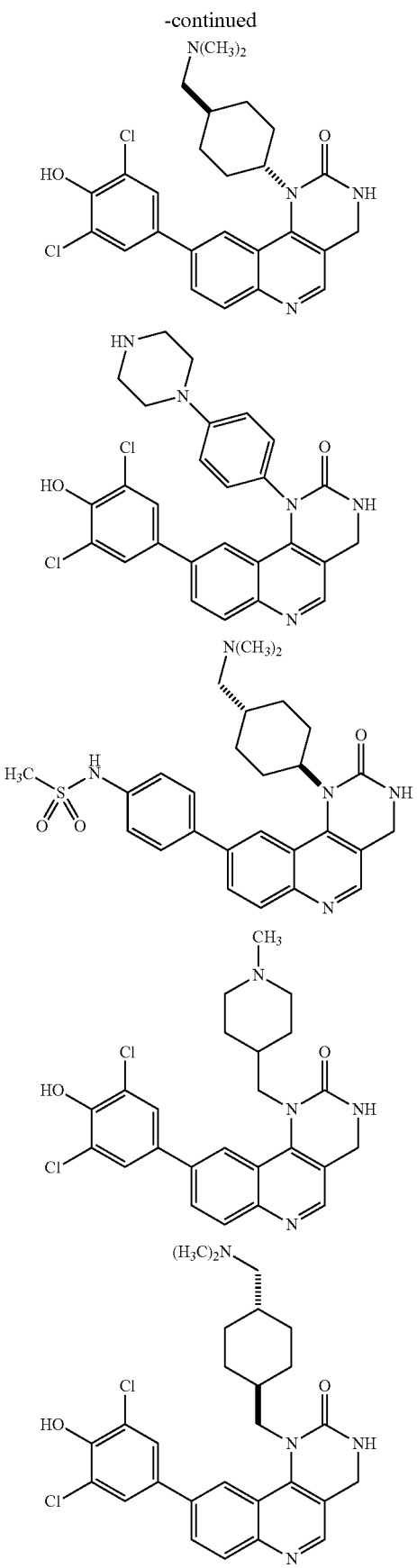
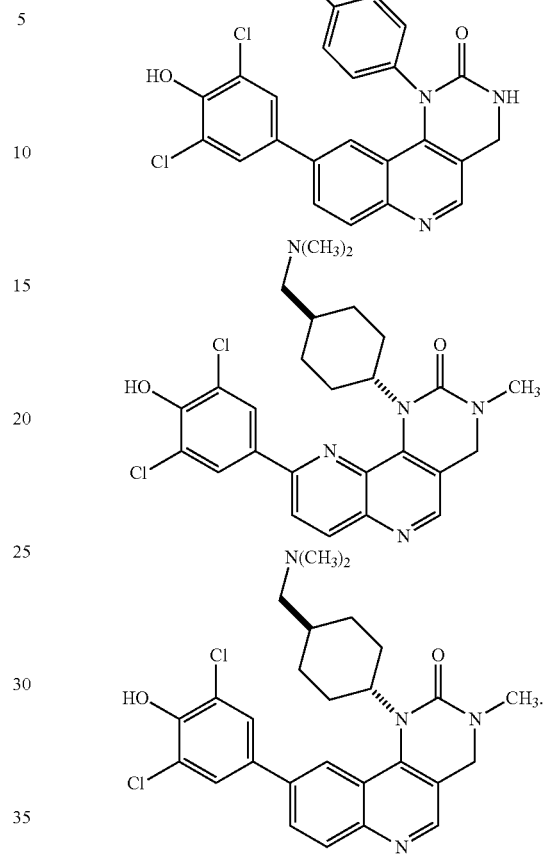

In certain embodiments, the invention provides a compound represented by formula (IV), or a pharmaceutically acceptable salt thereof:

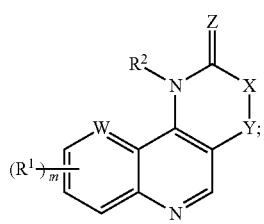

(IV)

wherein:
Z represents O, S, NH, or N(alkyl);
—X—Y— represents —CR$^3$=CR$^4$— or —CHR$^3$—CHR$^4$—;
R$^1$, independently for each occurrence, represents aryl, substituted by one or more substituents R$^x$, which, independently for each occurrence, is selected from the group consisting of halo, (C$_1$-C$_6$)alkyl, (C$_1$-C$_6$)alkenyl, (C$_1$-C$_6$)alkynyl, (C$_1$-C$_6$)haloalkyl, aryl, —OH, (C$_3$-C$_6$)cycloalkyl, (C$_1$-C$_6$)alkoxyl, (C$_1$-C$_6$)haloalkoxyl, —SH, —S((C$_1$-C$_6$)alkyl), (C$_1$-C$_6$)hydroxyalkyl, (C$_1$-C$_6$)alkoxy(C$_1$-C$_6$)alkyl, —CN, —CF$_3$, —NO$_2$, —NH$_2$, —NH(R$^6$), —N(R$^6$)$_2$, (C$_1$-C$_6$)alkyl substituted by —N(R$^6$)$_2$, —C(O)NH$_2$, —C(O)NH(R$^6$), —C(O)N (R⁶)₂, —N(H)C(O)(R⁶), —N(R⁶)C(O)(R⁶), —S(O)₂NH₂, —S(O)₂NH(R⁶), —S(O)₂N(R⁶)₂, —N(H)S(O)₂(R⁶), and —N(R⁶)S(O)₂(R⁶);
wherein at least one occurrence of R$^x$ is OH;
R² represents aryl, aralkyl, heteroaryl, heteroaralkyl, cycloalkyl, cycloalkylalkyl, heterocycloalkyl, or heterocycloalkylalkyl, optionally substituted by one or more occurrences of substituent R⁵;
R³ and R⁴ are each independently selected from the group consisting of H, alkyl, aralkyl, and aryl;
R⁵, independently for each occurrence, is selected from the group consisting of substituted or unsubstituted alkyl, alkenyl, alkynyl, halo, haloalkyl, alkoxyl, amino, aminoalkyl, hydroxy, hydroxyalkyl, aryl, aryloxy, arylalkoxy, heteroaryl, heteroaryloxy, heteroarylalkoxy, cyano, nitro, cycloalkyl, and heterocycloalkyl;
R⁶, independently for each occurrence, is selected from the group consisting of (C₁-C₆)alkyl, aryl, and aryl(C₁-C₆)alkyl, or, for —N(R⁶)₂, —C(O)N(R⁶)₂, and —S(O)₂ N(R⁶)₂, or two occurrences of R⁶, together with the nitrogen atom to which they are attached can be taken together to form an optionally substituted ring;
W represents N, CH, or CR¹; and
m is an integer from 1-3.

In certain embodiments, Z is O.

In certain embodiments, W is N. In alternative embodiments, W is CH.

In certain embodiments, —X—Y— is —CH₂—CH₂—. Alternatively, —X—Y— can be —CH=CH—.

In certain embodiments, R¹ of formula (IV) represents aryl, substituted by one or more substituents R$^x$, which, independently for each occurrence, is selected from the group consisting of (C₁-C₆)alkyl, (C₁-C₆)alkoxy, (C₁-C₆)haloalkyl, halo, —OH, (C₁-C₆)haloalkoxyl, —SH, —S((C₁-C₆)alkyl), (C₁-C₆)hydroxyalkyl, and —CF₃, wherein at least one occurrence of R$^x$ is OH. In other words, R¹ is an optionally substituted phenolyl group.

The R$^x$ that represents OH can be at any position on the aryl ring. In embodiments in which aryl is phenyl, the R$^x$ that represents OH can be at the ortho, meta, or para position of the phenyl ring. More than one occurrence of R$^x$ can be OH.

In certain embodiments, R¹ of formula (IV) represents aryl, substituted by at least two occurrences of R$^x$. Alternatively, R¹ of formula (IV) can be aryl, substituted by at least three occurrences of R$^x$.

In certain embodiments, R¹ represents aryl, substituted by at least two substituents R$^x$, which, independently for each occurrence, are selected from the group consisting of (C₁-C₆)haloalkyl, halo, —OH, (C₁-C₆)hydroxyalkyl, and —CF₃.

In exemplary embodiments, R$^x$ is

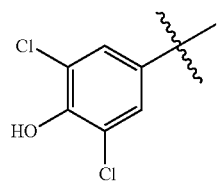

In various embodiments of the compound of formula (IV), at least one occurrence of R$^x$ is OH. In certain alternative embodiments, at least one occurrence of R$^x$ is —CH₂OH (e.g., R¹ is an optionally substituted benzyl alcohol, or (hydroxyalkyl)aryl.

In some embodiments, m is 1.

In certain embodiments, the compound of formula (IV) has the structure represented by formula (IVa):

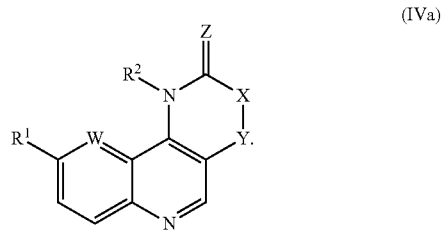

In certain embodiments, R² represents aryl, aralkyl, heteroaryl, heteroaralkyl, cycloalkyl, cycloalkylalkyl, heterocycloalkyl, or heterocycloalkylalkyl, substituted by one or more occurrences of substituent R⁵, wherein at least one occurrence of R⁵ is amino or aminoalkyl.

In some embodiments, the at least one occurrence of R⁵ that is amino or aminoalkyl is selected from the group consisting of —N(R⁷)(R⁸) and —(C₁-C₆)alkylene(N(R⁷)(R⁸)), wherein R⁷ and R⁸ are each independently selected from the group consisting of H, (C₁-C₆)alkyl, aryl, and aryl(C₁-C₆)alkyl, or, R⁷ and R⁸, together with the nitrogen atom to which they are attached can be taken together to form an optionally substituted heterocyclic ring.

In certain embodiments, R⁷ and R⁸ are each independently selected from the group consisting of H, (C₁-C₆)alkyl, and aryl(C₁-C₆)alkyl.

The compound of formula (IV) can alternatively be represented by formula (V),

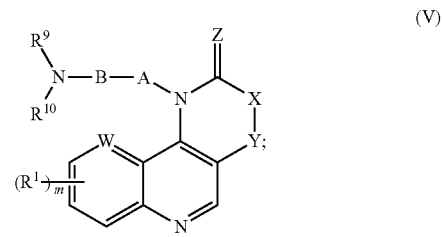

wherein:
A is represented by 1,4-cyclohexanediyl, 1,3-cyclohexanediyl, 1,2-cyclohexanediyl, 1,4-phenylene, 1,4-cycloheptanediyl, 1,3-cycloheptanediyl, 1,3-cyclooctanediyl, 1,4-cyclooctanediyl, 1,5-cyclooctanediyl;
B is represented by (C₁-C₆)alkylene or a bond; and
R⁹ and R¹⁰ are each independently selected from the group consisting of H, (C₁-C₆)alkyl, aryl, and aryl(C₁-C₆)alkyl, or, R⁹ and R¹⁰, together with the nitrogen atom to which they are attached can be taken together to form an optionally substituted heterocyclic ring.

In certain embodiments, R⁹ and R¹⁰ are each independently selected from the group consisting of H, (C₁-C₆) alkyl, and aryl(C₁-C₆)alkyl. In preferred embodiments, R⁹ and R¹⁰ are each independently H or (C₁-C₆)alkyl.

In certain embodiments, A represents 1,4-cyclohexanediyl.

In certain embodiments, B represents —CH₂— or a bond.

In certain embodiments, the compounds of the invention can be represented by one of the following structures, or a pharmaceutically acceptable salt thereof.

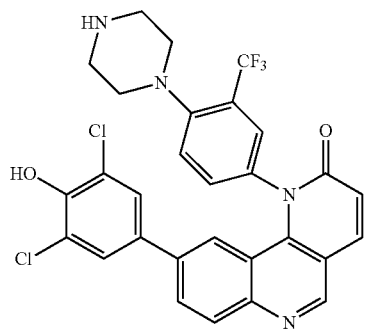

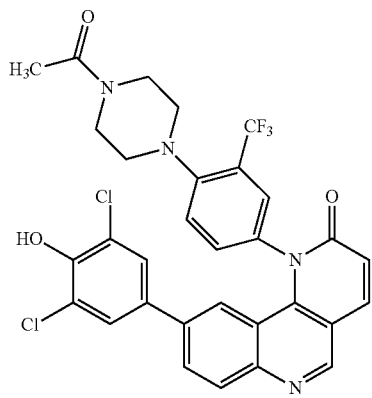

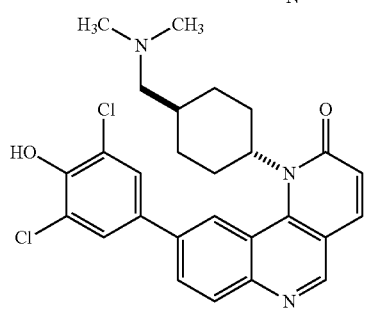

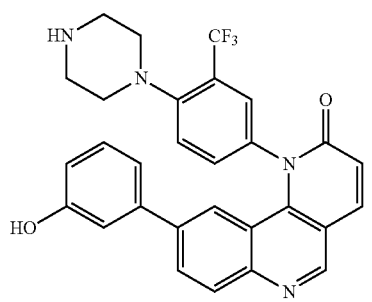

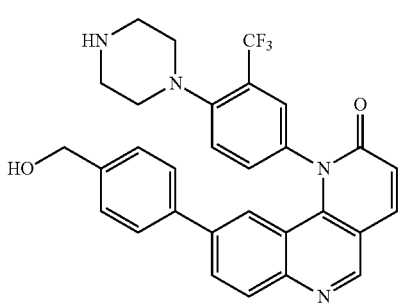

-continued

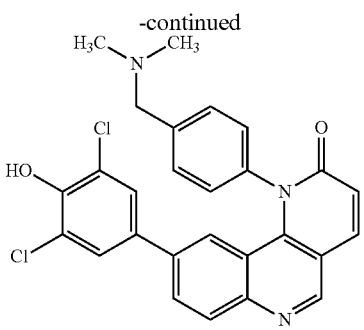

In certain embodiments of the compound of any one of formulae (I), (II), or (III), $R^1$ is aryl or heteroaryl (e.g., phenyl), substituted by one or more substituents, at least one of which is a hydrogen bond donor. Exemplary substituents that are hydrogen bond donors include —OH, —NH$_2$, —SH, (C$_1$-C$_6$)hydroxyalkyl, —NH(R$^6$), —C(O)NH$_2$, —C(O)NH(R$^6$), —N(H)C(O)(R$^6$), —S(O)$_2$NH$_2$, —S(O)$_2$NH(R$^6$), or —N(H)S(O)$_2$(R$^6$), and preferably include —OH, —NH$_2$, or —SH.

In certain preferred embodiments, the hydrogen bond donor substituent is attached at the para position of the aryl or heteroaryl ring.

III. Pharmaceutical Compositions of the Compounds of the Invention

In certain embodiments, the invention also provides pharmaceutical compositions, comprising a compound of the invention and a pharmaceutically acceptable carrier.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. In certain embodiments, the composition is a form suitable for injection, systemic administration, or topical administration. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch.

The composition can also be present in a solution or suspension suitable for topical administration. The topically applicable form of the composition can a transdermal patch, ointment, cream, gel, suspension, liquid, elixir, or eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for administration to the mouth may be presented as a mouthwash, or an oral spray, or an oral ointment.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Alternatively or additionally, compositions can be formulated for delivery via a catheter, stent, wire, or other intraluminal device. Delivery via such devices may be especially useful for delivery to the bladder, urethra, ureter, rectum, or intestine.

Dosage forms for the topical administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

IV. Methods of Using the Compounds of the Invention

MELK (maternal embryonic leucine zipper kinase) is serine/threonine kinase that has been implicated in the regulation of mitosis. Similar to other established mitotic factors such as Aurora kinases and Cyclin B1, MELK demonstrates an increased protein abundance during mitosis, and is degraded when cells progress into G1 phase.[1, 2] Recent studies propose an essential role of MELK in the mitotic progression of specific cancer cells, with MELK knockdown resulting in multiple mitotic defects including G2/M arrest, mitotic cell death, and cytokinesis failure.[2] During the early embryonic development of Xenopus, perturbing the expression of MELK through either knockdown or overexpression causes abortive cell division in embryos.[3] In addition, MELK is found to antagonize the activity of CDC25B, to potentially inhibit the mitotic entry leading to G2 arrest.[4] Thus, these seemingly paradoxical observations challenge a unified biology function of MELK in mitosis.

Adding to the difficulty in studying MELK is a lack of tool that enables fast and efficient control of the kinase activity of MELK. The dynamic nature of mitosis especially demands such a tool, to discriminate any observed phenotypes from indirect consequences of gene silencing or overexpression. Indeed, studies of mitotic factors with intrinsic enzymatic activity have been traditionally facilitated by the use of small molecule inhibitors, an approach that can offer fast and complete inhibition of its targets to facilitate investigation of proteins in sub-phase of mitosis. The compounds described herein present the first small molecule compounds that selectively inhibit MELK.

In certain embodiments, the invention provides methods of treating cancer, comprising administering to a patient in need thereof a therapeutically effective amount of a compound of the invention that is described herein.

In certain embodiments, the cancer is associated with overexpression of MELK. For example, cancer cells or tissues may have a higher or significantly higher expression level of MELK as compared to the expression level in normal cells or tissues. MELK expression can be determined through methods known to those of skill in the art, and such methods include microarray analysis of RNA samples prepared from normal and cancerous tissues.

The "normal" level of expression of a marker (e.g., MELK) is the level of expression of the marker in cells of a subject, e.g., a human patient, not afflicted with a cancer. An "over-expression" or "significantly higher level of expression" of a marker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

In certain embodiments, the invention relates to a method of treating a cancer selected from cervical cancer, colon cancer, breast cancer, gastric cancer, head and neck cancer, leukemia, lung cancer, ovarian cancer, pancreatic cancer, prostate cancer, and brain cancer. In certain embodiments, the cancer is breast cancer, ovarian cancer, or melanoma. In certain embodiments, the invention relates to treating basal-like breast cancer (BBC) with a compound of the invention. For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

The term "administering" is intended to include routes of administration which allow the agent to perform its intended function of inhibiting the activity of MELK. Examples of routes of administration which can be used include injection (subcutaneous, intravenous, parenterally, intraperitoneally, intrathecal, etc.), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, the methods of the invention further comprise conjointly administering to the patient a therapeutically effective amount of a second chemotherapeutic agent.

As used herein, the phrase "conjoint administration" refers to any form of administration of two or more different therapeutic compounds such that the second compound is administered while the previously administered therapeutic compound is still effective in the body (e.g., the two compounds are simultaneously effective in the patient). For example, the different therapeutic compounds can be administered either in the same formulation or in a separate formulation. The different therapeutic compounds, when administered in separate formulations, can be administered either concomitantly (i.e., simultaneously) or sequentially. In certain embodiments, the different therapeutic compounds can be administered within 5 minutes, 30 minutes, one hour, 12 hours, 24 hours, 36 hours, 48 hours, 72 hours, or 168 hours (one week) of one another. Thus, an individual who receives such treatment can benefit from a combined effect of different therapeutic compounds.

In certain embodiments, conjoint administration of compounds of the invention with one or more additional therapeutic agents (e.g., one or more additional chemotherapeutic agents) provides improved efficacy relative to each individual administration of the compound of the invention (e.g., a compound of Formula (I)) or the one or more additional therapeutic agents. In certain such embodiments, the conjoint administration provides an additive effect, wherein an additive effect refers to the sum of each of the effects of individual administration of the compound of the invention and the one or more additional therapeutic agents.

In certain embodiments, conjoint administration of compounds of the invention with one or more additional therapeutic agents (e.g., one or more additional chemotherapeutic agents) provides improved efficacy relative to the sum of each of the effects of individual administration of the compound of the invention and the one or more additional therapeutic agents (i.e., relative to the additive effect). In certain such embodiments, conjoint administration of the compound of the invention and the second chemotherapeutic agent provides a synergistic effect. In certain embodiments, the second chemotherapeutic agent is paclitaxel.

In certain embodiments, the methods of the invention further comprise conjointly administering to the patient radiation therapy.

The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, Pd-103, Ir-192), intravenous administration of radioisotopes such as strontium-89, thoracic radiation therapy, intraperitoneal $^{32}$P radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In certain embodiments, the methods of the invention further comprise conjointly administering to the patient an additional anti-cancer agent such as immunotherapy, hormone therapy, and gene therapy. Such therapies include, but are not limited to, the use of antisense polynucleotides, ribozymes, RNA interference molecules, triple helix polynucleotides and the like, where the nucleotide sequence of such compounds are related to the nucleotide sequences of DNA and/or RNA of genes that are linked to the initiation, progression, and/or pathology of a tumor or cancer. For example, oncogenes, growth factor genes, growth factor receptor genes, cell cycle genes, DNA repair genes, and others, may be targeted in such therapies.

Immunotherapy may comprise, for example, use of cancer vaccines and/or sensitized antigen presenting cells. Immunotherapy can also involve derepression of immunoinhibitory pathways, such as by targeting PD-L1, PD-L2, PD-1, CTLA-4, and the like. The immunotherapy can involve passive immunity for short-term protection of a host, achieved by the administration of an antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

The invention also provides methods for inhibiting MELK, comprising contacting MELK with a compound of the invention in an amount effective to inhibit MELK. In certain embodiments, the method is conducted in vitro. In certain embodiments, the method is conducted in vivo. Inhibition of MELK can be determined by the Z'-LYTE® biochemical assay from Life Technologies (Life Technologies Z'-LYTE® Screening Protocol and Assay Conditions, June 2012, incorporated herein by reference).

The invention also provides methods for treating or preventing a condition associated with aberrant maternal embryonic leucine zipper kinase (MELK), comprising administering to a subject in need thereof a therapeutically effective amount of a compound of the invention.

In certain embodiments, the invention provides methods for treating or preventing a condition associated with hyperactivation of MELK, or a condition associated with an essential role of MELK in disease progression and/or maintenance.

In certain embodiments, the condition to be treated is associated with heightened expression of MELK. In certain embodiments, the condition to be treated is associated with heightened activity of MELK.

The invention also provides methods for decreasing the rate of mitosis in a cancer cell, comprising contacting a cancer cell a compound of the invention in an amount effective to decrease the rate of mitosis of the cancer cell. The rate of mitosis of cancer cells can be measured through methods known to persons of skill in the art. These methods include immunohistochemical analysis of established mitotic markers, such as Histone H3 phosphorylation.

In addition to the assessing the rate of mitosis of a cancer cell after treatment with a compound of the invention, the response to cancer therapy can be assessed. The term "response to cancer therapy" or "outcome of cancer therapy" relates to any response of the hyperproliferative disorder (e.g., cancer) to a cancer therapy, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Response may also be assessed by caliper measurement or pathological examination of the tumor after biopsy or surgical resection for solid cancers. Responses may be recorded in a quantitative fashion like percentage change in tumor volume. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to copy number, level of expression, level of activity, etc. of a marker (e.g., MELK) determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom the measurement values are known. In certain embodiments, the same doses of cancer therapeutic agents are administered to each subject. In related embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Outcomes can also be measured in terms of a "hazard ratio" (the ratio of death rates for one patient group to another; provides likelihood of death at a certain time point), "overall survival" (OS), and/or "progression free survival." In certain embodiments, the prognosis comprises likelihood of overall survival rate at 1 year, 2 years, 3 years, 4 years, or any other suitable time point. The significance associated with the prognosis of poor outcome in all aspects of the present invention is measured by techniques known in the art. For example, significance may be measured with calculation of odds ratio. In a further embodiment, the significance is measured by a percentage. In one embodiment, a significant risk of poor outcome is measured as odds ratio of 0.8 or less or at least about 1.2, including by not limited to: 0.1, 0.2, 0.3, 0.4, 0.5, 0.6, 0.7, 0.8, 1.2, 1.3, 1.4, 1.5, 1.6, 1.7, 1.8, 1.9, 2.0, 2.5, 3.0, 4.0, 5.0, 10.0, 15.0, 20.0, 25.0, 30.0 and 40.0. In a further embodiment, a significant increase or reduction in risk is at least about 20%, including but not limited to about 25%, 30%, 35%, 40%, 45%, 50%, 55%, 60%, 65%, 70%, 75%, 80%, 85%, 90%, 95% and 98%. In a further embodiment, a significant increase in risk is at least about 50%.

EXAMPLES

Example 1

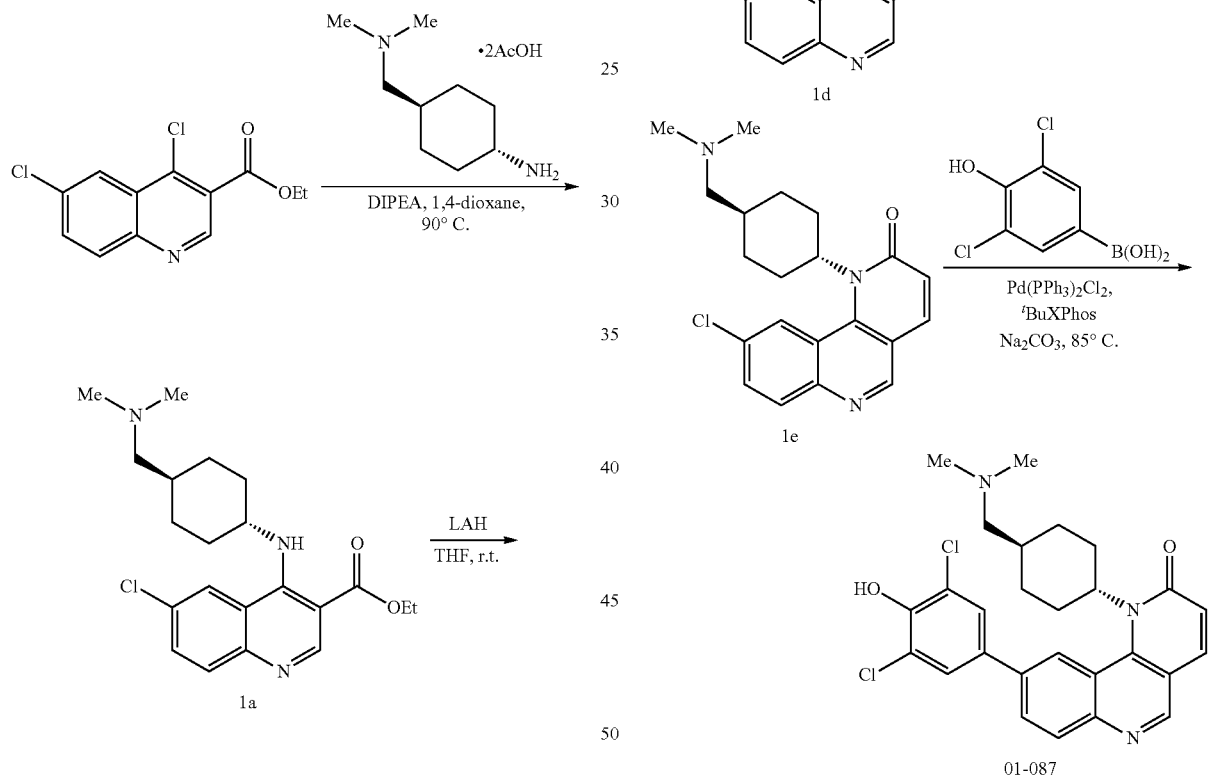

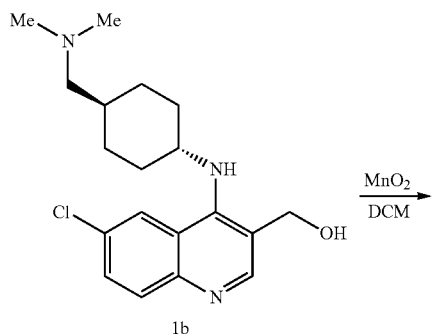

Ethyl 6-chloro-4-((trans-4-((dimethylamino)methyl)cyclohexyl)amino)quinoline-3-carboxylate (1a)

In a stirring 1,4-dioxane solution (8 ml) of ethyl 4,6-dichloroquinoline-3-carboxylate (1 equiv., 0.716 mmol), trans-4-((dimethylamino)methyl)cyclohexan-1-amine diacetic acid (1 equiv., 0.716 mmol) and N,N-diisopropylethylamine (10 equiv., 7.16 mmol) were added and allowed to dissolve. The resulting solution was heated up to 90° C., and stirred for 12 hours before cooling to room temperature. The solvent was removed under reduced pressure, and the resultant crude was purified by Flash Column Chromatography on silica gel with 0-10% CH$_2$Cl$_2$/methanol (1.75N ammonia) gradient to afford compound 1a. MS (ESI) calculated for $C_{21}H_{29}ClN_3O_2$ [M+H]$^+$, 390; found 390.

(6-chloro-4-(trans-4-((dimethylamino)methyl)cyclohexyl)amino)quinolin-3-yl)methanol (1)

To a THF (9 mL) solution of ethyl 6-chloro-4-((trans-4-((dimethylamino)methyl)cyclohexyl)-amino)quinoline-3-carboxylate (1a, 1 equiv., 0.308 mmol) purged with argon and sitting in an ice bath, lithium aluminium hydride (70 mg, 6 equiv., 1.85 mmol) was slowly added in three portions. The reaction mixture was allowed to warm up to room temperature and stirred overnight. The reaction was quenched by an addition of 70 μL of water, followed by 70 μL of 15% NaOH (aq) and 210 μL of water. Filter the crude through Celite. Purification was performed by Flash Column Chromatography on silica gel with 0-20% $CH_2Cl_2$/methanol (1.75N ammonia) gradient to afford compound 1b. MS (ESI) calculated for $C_{19}H_{27}ClN_3O$ [M+H]$^+$, 348; found 348.

Ethyl (E)-3-(6-chloro-4-((trans-4-((dimethylamino) methyl)cyclohexyl)amino)quinolin-3-yl)acrylate (1d)

To a dichloromethane (2.5 mL) solution of (6-chloro-4-((trans-4-((dimethylamino)methyl)cyclohexyl)amino)quinolin-3-yl)methanol (1b, 89 mg, 1 equiv., 0.256 mmol) was added manganese oxide (445 mg, 5 mass equiv.) and stirred for 3 hours at room temperature. The reaction mixture was filtered and concentrated to afford the crude product, 6-chloro-4-((trans-4-((dimethylamino)methyl)cyclohexyl) amino)quinoline-3-carbaldehyde (1c), which was used in the next step without further purification.

To an ethanol (5 mL) solution of compound 1c (1.0 equiv., 0.256 mmol) was added triethyl phosphonoacetate (2.0 equiv., 0.512 mmol) and potassium carbonate (3.0 equiv., 0.768 mmol). The reaction was heated up to 100° C., and stirred for 5 hours before cooling to room temperature. The reaction mixture was filtered through cotton, and concentrated under reduced pressure. Purification was performed by Flash Column Chromatography on silica gel with 0-20% $CH_2Cl_2$/methanol (1.75N ammonia) gradient to afford the compound 1d. MS (ESI) calculated for $C_{23}H_{31}ClN_3O_2$ [M+H]$^+$, 416; found 416.

9-chloro-1-(trans-4-((dimethylamino)methyl)cyclohexyl)benzo-[h][1,6]naphthyridin-2(1H)-one (1e)

To a 2-ethoxyethanol solution of ethyl (E)-3-(6-chloro-4-((trans-4-((dimethylamino)methyl)cyclohexyl)amino)quinolin-3-yl)acrylate (1d, 1.0 equiv., 0.27 mmol) was added potassium carbonate (0.1 equiv., 0.03 mmol). The reaction was heated to 150° C., and stirred for 12 hours. The reaction mixture was filtered through cotton, and concentrated under reduced pressure. Purification was performed by Flash Column Chromatography on silica gel with 0-10% $CH_2Cl_2$/methanol (1.75N ammonia) gradient to afford the compound 1e. MS (ESI) calculated for $C_{21}H_{25}ClN_3O$ [M+H]$^+$, 370; found 370.

9-(3,5-dichloro-4-hydroxyphenyl)-1-(trans-4-((dimethylamino)methyl)cyclohexyl)benzo-[h][1,6]naphthyridin-2(1H)-one (01-087)

In a 1,4-dioxane/sat. $Na_2CO_3$(aq)(3:1) solution (0.8 mL) containing 9-chloro-1-(trans-4-((dimethylamino)methyl)cyclohexyl)benzo-[h][1,6]naphthyridin-2(1H)-one (1e, 1.0 equiv., 0.023 mmol) was added (3,5-dichloro-4-hydroxyphenyl)boronic acid (1.5 equiv., 0.034 mmol) and 2-di-tert-butylphosphino-2',4',6'-triisopropylbiphenyl (10% equiv., 0.002 mmol). The reaction was purged thoroughly with argon, to which 10% equivalent of bis(tripheylphosphine) palladium(II) dichloride (0.002 mmol) was added. The reaction was heated to 85° C. and continue stirring overnight. The reaction was worked up in water (10 mL) and $CHCl_3$: iPrOH (4:1) (15 mL×3). The organic layers were collected and washed with brine solution (10 mL). Purification was performed by reverse-phase prep-HPLC (C18) using water (0.05% trifluoroacetic acid)/methanol (0.05% trifluoroacetic acid) gradient to afford the compound 01-087 as a trifluoroacetic salt.

Compound 01-087. $^1$H NMR (400 MHz, DMSO) δ 10.60-10.45 (br, 1H), 9.16-9.03 (br, 1H), 9.04 (s, 1H), 8.25 (s, 1H), 8.19 (dd, J=8.8, 1.6 Hz, 1H), 8.15 (d, J=8.6 Hz, 1H), 8.11 (d, J=9.4 Hz, 1H), 7.87 (s, 2H), 6.72 (d, J=9.4 Hz, 1H), 4.68 (m, 1H), 2.97-2.83 (m, 4H), 2.78 (s, 3H), 2.77 (s, 3H), 2.03 (m, 2H), 1.93-1.80 (m, 3H), 1.10 (m, 2H). MELK IC$_{50}$ as determined by Z'-LYTE® biochemical assay: 9.6 nM. TFA salt. MS (ESI) calculated for $C_{27}H_{28}Cl_2N_3O_2$ [M+H]$^+$, 495.148; found 496.

Example 2

Compounds 01-045, 01-047, 01-071, 01-092, and 01-101 were synthesized in procedures analogous to compound 01-087.

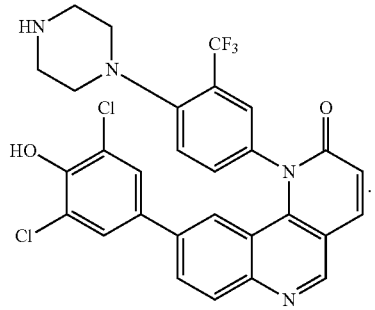

Compound 01-045

Calculated mass: 584.099. Observed mass: 585. MELK IC$_{50}$ as determined by Z'-LYTE® biochemical assay: 7.63 nM. TFA salt.

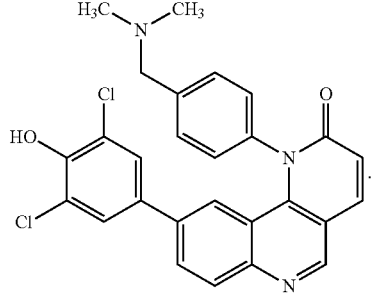 [SMILES: CN(C)Cc1ccc(-n2c(=O)ccc3cnc4ccc(-c5cc(Cl)c(O)c(Cl)c5)cc4c32)cc1]

Compound 01-047

Calculated mass: 489.101. Observed mass: 490. MELK IC$_{50}$: 10.8. TFA salt.

39
Compound 01-071
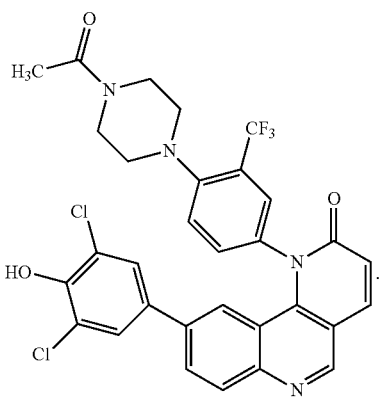
Calculated mass: 626.11. Observed mass: 627. MELK $IC_{50}$: 294. TFA salt.
Compound 01-092
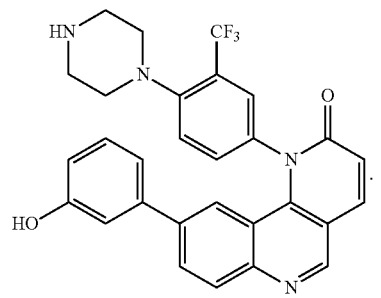
Calculated mass: 516.177. Observed mass: 517. MELK $IC_{50}$: 146. TFA salt.
Compound 01-101
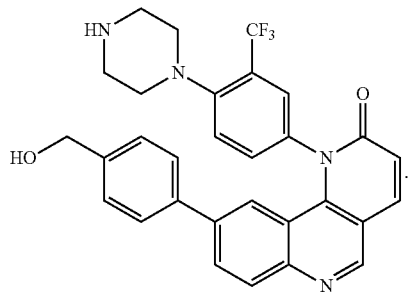
Calculated mass: 530.193. Observed mass: 531. MELK $IC_{50}$: 119. TFA salt.
40
Example 3
Scheme 2. Synthesis Scheme for 01-091.
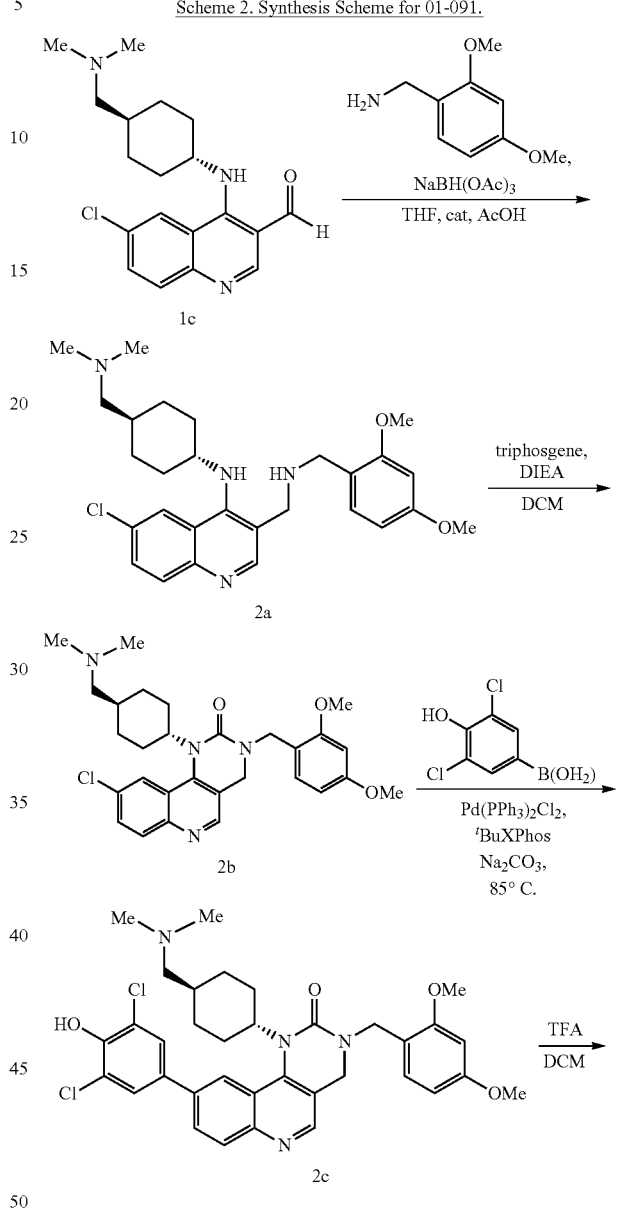

6-chloro-3-(((2,4-dimethoxybenzyl)amino)methyl)-N-(trans-4-((dimethylamino)methyl)-cyclohexyl) quinolin-4-amine (2a)

To a tetrahydrofuran (1 mL) solution containing 6-chloro-4-((trans-4-((dimethylamino)methyl)cyclohexyl)amino)quinoline-3-carbaldehyde (1c, 1 equiv., 0.05 mmol), (2,4-dimethoxyphenyl)methanamine (2.0 equiv., 0.10 mmol) and one drop of acetic acid was added sodium triacetoxyborohydride (5.0 equiv., 0.25 mmol). Stir at room temperature overnight. The reaction was worked up in water (10 mL) and dichloromethane (15 mL×3). The organic layers were collected and washed with brine solution (10 mL). Purification was performed by Flash Column Chromatography on silica gel with 0-10% $CH_2Cl_2$/methanol (1.75N ammonia) gradient to afford the compound 2a. MS (ESI) calculated for $C_{28}H_{38}ClN_4O_2$ $[M+H]^+$, 497; found 497.

9-chloro-3-(2,4-dimethoxybenzyl)-1-(trans-4-((dimethylamino)methyl)cyclohexyl)-3,4-dihydropyrimido[5,4-c]quinolin-2(1H)-one (2b)

To a dichloromethane solution containing 6-chloro-3-(((2,4-dimethoxybenzyl)amino)methyl)-N-(trans-4-((dimethylamino)methyl)-cyclohexyl)quinolin-4-amine (2a, 1.0 equiv., 0.037 mmol) and diisopropylethylamine (3.0 equiv., 0.111 mmol) in ice bath was added triphosgene (1.0 equiv., 0.037 mmol). Stir for 1 hour. Remove the solvent under reduced pressure. Purification was performed by Flash Column Chromatography on silica gel with 0-10% $CH_2Cl_2$/methanol (1.75N ammonia) gradient to afford the compound 2b. MS (ESI) calculated for $C_{29}H_{36}ClN_4O_3$ $[M+H]^+$, 523; found 523.

9-(3,5-dichloro-4-hydroxyphenyl)-1-(trans-4-((dimethylamino)methyl)cyclohexyl)-3,4-dihydropyrimido[5,4-c]quinolin-2(1H)-one (01-091)

In a 1,4-dioxane/sat. $Na_2CO_3$(aq)(3:1) solution (0.8 mL) containing 9-chloro-3-(2,4-dimethoxybenzyl)-1-(trans-4-((dimethylamino)methyl)cyclohexyl)-3,4-dihydropyrimido[5,4-c]quinolin-2(1H)-one (2b, 1.0 equiv., 0.015 mmol) was added (3,5-dichloro-4-hydroxyphenyl)boronic acid (1.5 equiv., 0.023 mmol) and 2-di-tert-butylphosphino-2',4',6'-triisopropylbiphenyl (10% equiv., 0.0015 mmol). The reaction was purged thoroughly with argon, to which 10% equivalent of bis(triphenylphosphine)palladium(II) dichloride (0.0015 mmol) was added. The reaction was heated to 85° C. and continue stirring for 2 hours. The reaction was worked up in water (10 mL) and $CHCl_3$:iPrOH (4:1) (15 mL×3). The organic layers were collected and washed with brine solution (10 mL). The solvent was removed under reduced pressure to afford the crude product 9-(3,5-dichloro-4-hydroxyphenyl)-3-(2,4-dimethoxybenzyl)-1-(trans-4-((dimethylamino)methyl)-cyclohexyl)-3,4-dihydropyrimido[5,4-c]quinolin-2(1H)-one (2c), which was used in the next step without further purification. MS (ESI) calculated for $C_{35}H_{39}Cl_2N_4O_4$ $[M+H]^-$, 649; found 649.

9-(3,5-Dichloro-4-hydroxyphenyl)-3-(2,4-dimethoxybenzyl)-1-(trans-4-((dimethylamino)methyl)cyclohexyl)-3,4-dihydropyrimido[5,4-c]quinolin-2(1H)-one (2c, 1.0 equiv., 0.015 mmol) was stirred in a trifluoroacetic acid/dichloromethane (1:1, 1 mL) solution overnight. The solvent was removed under reduced pressure, and the crude was purified by reverse-phase prep-HPLC (C18) using water (0.05% trifluoroacetic acid)/methanol (0.05% trifluoroacetic acid) gradient to afford the compound 01-091 as a trifluoroacetic salt.

Compound 01-091. $^1$H NMR (400 MHz, DMSO) δ 10.63-10.49 (br, 1H), 9.14-9.04 (br, 1H), 8.78 (s, 1H), 8.19 (dd, J=8.6, 1.8 Hz, 1H), 8.10 (d, J=8.6 Hz, 1H), 8.09 (d, J=1.8 Hz, 1H), 7.84 (s, 2H), 7.63 (s, 1H), 4.40 (s, 2H), 3.85 (m, 1H), 2.89 (t, J=6.3 Hz, 2H), 2.77 (s, 3H), 2.76 (s, 3H), 2.61 (m, 2H), 2.18 (m, 2H), 1.87 (m, 2H), 1.80 (m, 1H), 1.07 (m, 2H). MS (ESI) calculated for $C_{26}H_{29}Cl_2N_4O_2$ $[M+H]^+$, 499; found 499. MELK $IC_{50}$ as determined by Z'-LYTE® biochemical assay: 10.5 nM. TFA salt.

Example 4

Compounds 01-088, 01-100, 01-131, 01-144, 02-020, and 02-029 were synthesized in procedures analogous to compound 01-091.

Compound 01-088

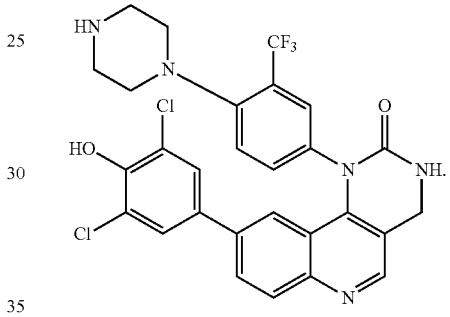

$^1$H NMR (400 MHz, DMSO) δ 10.52-10.38 (br, 1H), 8.92-8.80 (br, 2H), 8.84 (s, 1H), 8.03 (d, J=9.0, 1H), 7.99-7.92 (m, 3H), 7.62 (dd, J=8.6, 2.3 Hz, 1H), 7.54 (d, J=8.6 Hz, 1H), 7.16 (s, 2H), 7.09 (d, J=1.6 Hz, 1H), 4.63 (s, 2H), 3.20 (m, 4H), 3.02 (m, 4H). Calculated mass: 587.11. Observed mass: 588. MELK $IC_{50}$ as determined by Z'-LYTE® biochemical assay: 5.48 nM. TFA salt.

Compound 01-100

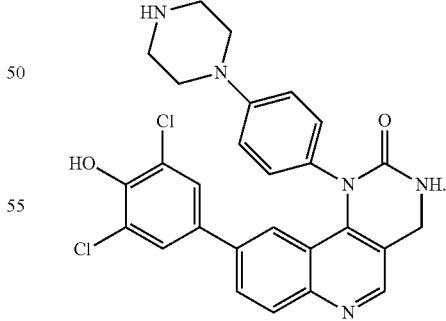

$^1$H NMR (400 MHz, DMSO) δ 10.59-10.38 (br, 1H), 8.88-8.75 (br, 2H), 8.87 (s, 1H), 8.06 (dd, J=9.0, 1.8 Hz, 1H), 8.01 (d, J=9.0 Hz, 1H), 7.90 (s, 1H), 7.44 (d, J=1.8 Hz, 1H), 7.37 (d, J=9.0 Hz, 2H), 7.19 (s, 2H), 7.11 (d, J=9.0 Hz, 2H), 4.62 (s, 2H), 3.45 (m, 4H), 3.25 (m, 4H). Calculated mass: 519.123. Observed mass: 520. MELK $IC_{50}$: 2.16. TFA salt.

Compound 01-131
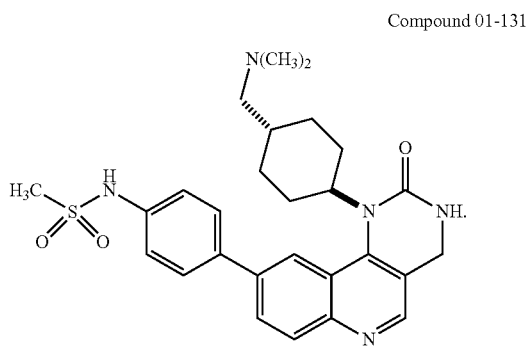
Calculated mass: 507.23. Observed mass: 508. MELK IC$_{50}$: 4990. TFA salt.
Compound 02-029
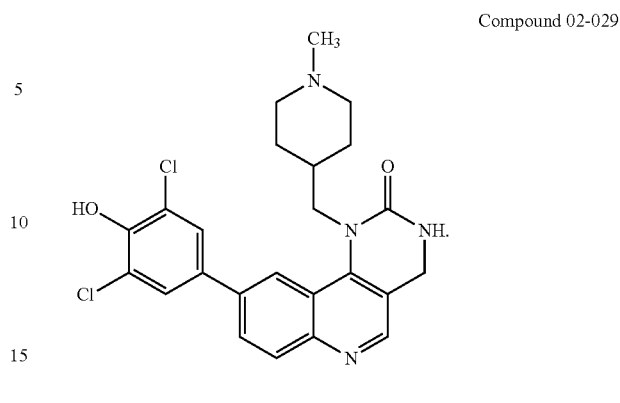
Calculated mass: 470.128. Observed mass: 471. MELK IC$_{50}$: 386. TFA salt.
Example 5
Compound 01-144
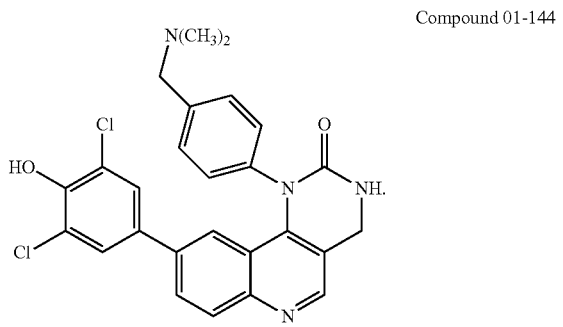 [SMILES: CN(C)Cc1ccc(N2C(=O)NCc3cnc4ccc(-c5cc(Cl)c(O)c(Cl)c5)cc4c32)cc1]
$^1$H NMR (400 MHz, DMSO) δ 10.54-10.41 (br, 1H), 9.82-9.70 (br, 1H), 8.84 (s, 1H), 8.01 (d, J=9.0 Hz, 1H), 7.96 (dd, J=9.0, 2.0 Hz, 1H), 7.90 (s, 1H), 7.61 (s, 4H), 7.18 (d, J=2.0 Hz, 1H), 7.08 (s, 2H), 4.63 (s, 2H), 4.39 (d, J=3.9 Hz, 2H), 2.71 (s, 3H), 2.70 (s, 3H). Calculated mass: 492.112. Observed mass: 493. MELK IC$_{50}$: 9.4. TFA salt.
Compound 02-020
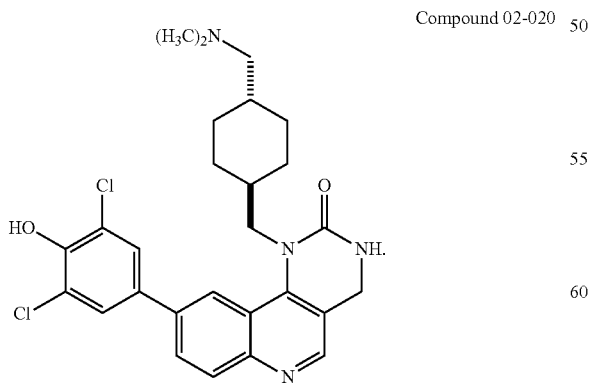
Calculated mass: 512.175. Observed mass: 513. MELK IC$_{50}$: 404. TFA salt.
Scheme 3. Synthetic Scheme for 02-095.
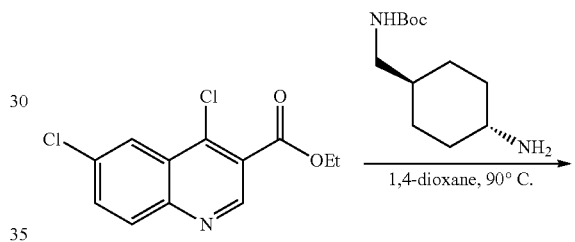
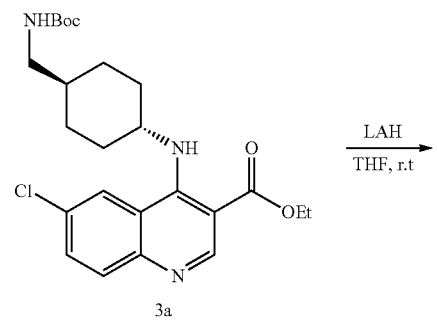
3a
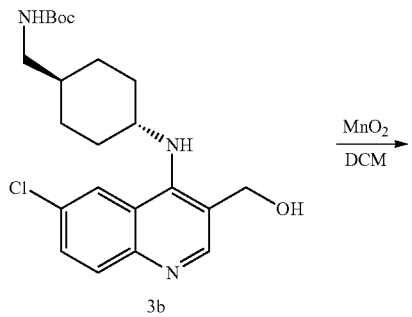
3b

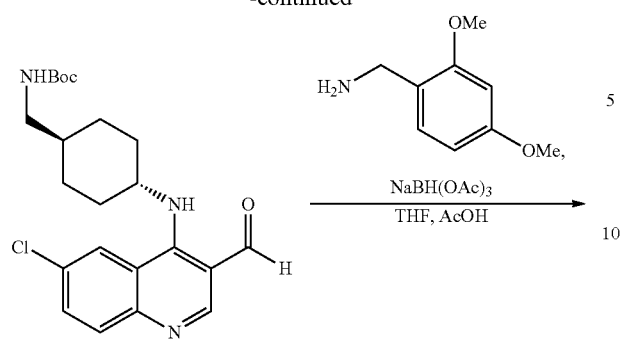

3c

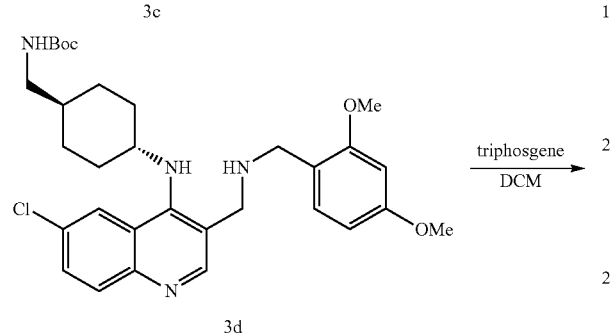

3d

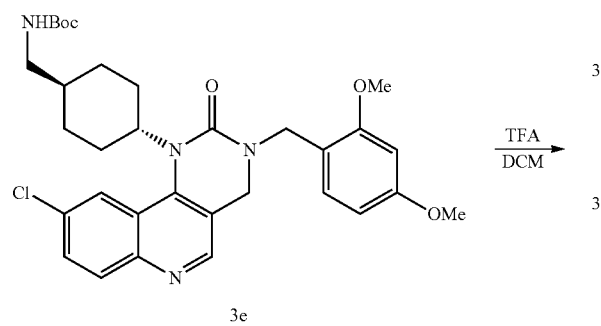

3e

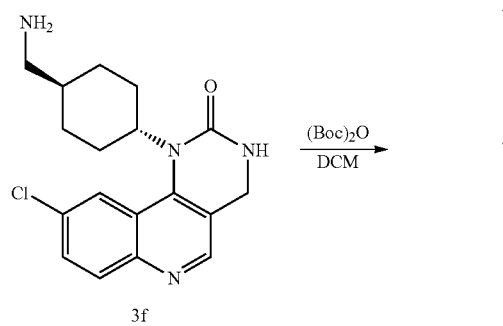

3f

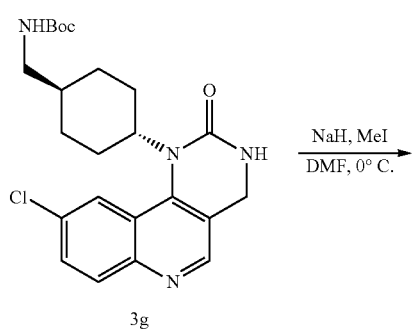

3g

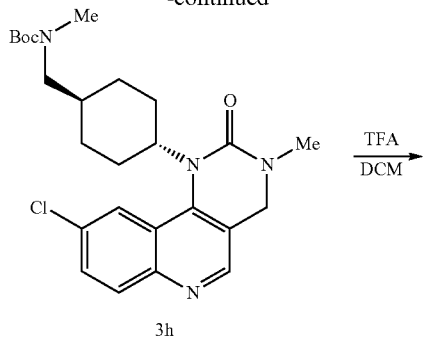

3h

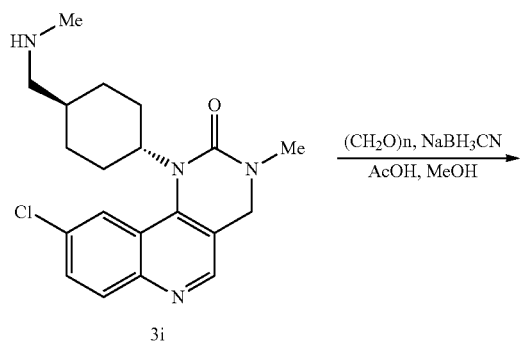

3i

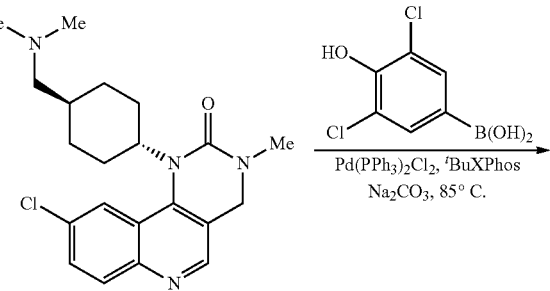

3j 02-095 tert-butyl (((trans-4-((6-chloro-3-(hydroxymethyl)quinolin-4-yl)amino)cyclohexyl)methyl)-carbamate (3b)

In a stirring 1,4-dioxane solution (8 ml) of ethyl 4,6-dichloroquinoline-3-carboxylate (1 equiv., 1.0 mmol), tert-butyl ((trans-4-aminocyclohexyl)methyl)carbamate (1 equiv., 1.0 mmol) and N,N-diisopropylethylamine (3 equiv., 3.0 mmol) were added and allowed to dissolve. The resulting solution was heated up to 90° C., and overnight before cooling to room temperature. The solvent was removed under reduced pressure to afford the crude product ethyl 4-((trans-4-(((tert-butoxycarbonyl)amino)methyl)cyclohexyl)amino)-6-chloroquinoline-3-carboxylate (3a), which was used for the next step without purification. MS (ESI) calculated for $C_{24}H_{33}ClN_3O_4$ [M+H]$^+$, 462; found 462.

To a THF (10 mL) solution of ethyl 4-((trans-4-(((tert-butoxycarbonyl)amino)methyl)-cyclohexyl)amino)-6-chloroquinoline-3-carboxylate (3a, 1 equiv., 1.0 mmol) purged with argon and sitting in an ice bath, lithium aluminium hydride (190 mg, 5 equiv., 5.0 mmol) was slowly added in three portions. The reaction mixture was allowed to warm up to room temperature and stirred overnight. The reaction was quenched by an addition of 190 μL of water, followed by 190 μL of 15% NaOH(aq) and 570 μL of water. Filter the crude through Celite. Purification was performed by Flash Column Chromatography on silica gel with 0-20% $CH_2Cl_2$/methanol (1.75N ammonia) gradient to afford the compound tert-butyl ((trans-4-((6-chloro-3-(hydroxymethyl)quinolin-4-yl) amino)cyclohexyl)methyl)carbamate (3b). MS (ESI) calculated for $C_{22}H_{31}ClN_3O_3$ [M+H]$^+$, 420; found 420.

tert-butyl ((trans-4-((6-chloro-3-(((2,4-dimethoxybenzyl)amino)methyl)quinolin-4-yl)amino)cyclohexyl)methyl)carbamate (3d)

To a dichloromethane (8 mL) solution of tert-butyl ((trans-4-((6-chloro-3-(hydroxymethyl)quinolin-4-yl) amino)cyclohexyl)methyl)carbamate (3b, 192.8 mg, 1 equiv., 0.46 mmol) was added manganese oxide (1 g, 5 mass equiv.) and stirred for 3 hours at room temperature. The reaction mixture was filtered and concentrated to afford the crude product, tert-butyl ((trans-4-((6-chloro-3-formylquinolin-4-yl)amino)cyclohexyl)methyl)carbamate (3c), which was used in the next step without further purification. MS (ESI) calculated for $C_{22}H_{29}ClN_3O_3$ [M+H]$^+$, 418; found 418.

To a tetrahydrofuran (4 mL) solution containing tert-butyl ((trans-4-((6-chloro-3-formylquinolin-4-yl)amino)cyclohexyl)methyl)carbamate (3c, 1 equiv., 0.263 mmol), (2,4-dimethoxyphenyl)methanamine (2.0 equiv., 0.562 mmol) and two drops of acetic acid was added sodium triacetoxyborohydride (5.0 equiv., 1.316 mmol). Stir at room temperature overnight. The reaction was worked up in water (20 mL) and dichloromethane (30 mL×3). The organic layers were collected and washed with brine solution (15 mL). Purification was performed by Flash Column Chromatography on silica gel with 0-20% $CH_2Cl_2$/methanol (1.75N ammonia) gradient to afford the compound tert-butyl ((trans-4-((6-chloro-3-(((2,4-dimethoxybenzyl)amino)methyl)quinolin-4-yl)amino)cyclohexyl)methyl)carbamate (3d). MS (ESI) calculated for $C_{31}H_{42}ClN_4O_4$ [M+H]$^+$, 569, found 569.

1-(trans-4-(aminomethyl)cyclohexyl)-9-chloro-3,4-dihydropyrimido[5,4-c]quinolin-2(1H)-one (3f)

To a dichloromethane (10 mL) solution containing tert-butyl ((trans-4-((6-chloro-3-(((2,4-dimethoxybenzyl)amino) methyl)quinolin-4-yl)amino)cyclohexyl)methyl)carbamate (3d, 1.0 equiv., 0.571 mmol) and triethylamine (6.0 equiv., 3.43 mmol) in ice bath was added triphosgene (1.0 equiv., 0.571 mmol). Stir for 1 hour. Remove the solvent under reduced pressure to afford the product tert-butyl ((trans-4-(9-chloro-3-(2,4-dimethoxybenzyl)-2-oxo-3,4-dihydropyrimido[5,4-c]quinolin-1(2H)-yl)cyclohexyl)methyl)carbamate (3e), which was used in the next step without further purification. MS (ESI) calculated for $C_{32}H_{40}ClN_4O_5$ [M+H]$^+$, 595; found 595.

tert-Butyl ((trans-4-(9-chloro-3-(2,4-dimethoxybenzyl)-2-oxo-3,4-dihydropyrimido[5,4-c]quinolin-1(2H)-yl)cyclohexyl)methyl)carbamate (3e, 1.0 equiv., 0.571 mmol) was stirred in a trifluoroacetic acid/dichloromethane (1:1, 2 mL) solution overnight. The solvent was removed under reduced pressure, and the crude was purified by Flash Column Chromatography on silica gel with 0-20% $CH_2Cl_2$/methanol (1.75N ammonia) gradient to afford the compound 1-(trans-4-(aminomethyl)cyclohexyl)-9-chloro-3,4-dihydropyrimido [4,5-c]quinolin-2(1H)-one (3f). MS (ESI) calculated for $C_{18}H_{22}ClN_4O$ [M+H]$^+$, 345; found 345.

9-chloro-3-methyl-1-(trans-4-((methylamino)methyl) cyclohexyl)-3,4-dihydropyrimido[5,4-c]quinolin-2 (1H)-one (3i)

To a dichloromethane solution containing 1-(trans-4-(aminomethyl)cyclohexyl)-9-chloro-3,4-dihydropyrimido [5,4-c]quinolin-2(1H)-one (3f, 1.0 equiv., 0.046 mmol) and triethylamine (2.0 equiv., 0.092 mmol) was added di-tert-butyl dicarbonate (1.5 equiv., 0.070 mmol). Stir at room temperature for 1 hour. The reaction was worked up in sat. $Na_2CO_{3(aq)}$ (5 mL) and dichloromethane (15 mL×3). The organic layers were collected, washed with brine solution (10 mL), and concentrated to afford the crude tert-butyl ((trans-4-(9-chloro-2-oxo-3,4-dihydropyrimido[5,4-c]quinolin-1(2H)-yl)cyclohexyl)methyl)carbamate (3g), which was used in the next step without purification.

To a stirring solution of N,N-dimethylformamide solution containing tert-butyl ((trans-4-(9-chloro-2-oxo-3,4-dihydropyrimido[5,4-c]quinolin-1(2H)-yl)cyclohexyl)methyl)carbamate (3g, 1.0 equiv., 0.063 mmol) in an ice bath was added methyl iodide (4.0 equiv., 0.252 mmol). To the reaction mixture was added sodium hydride (4.0 equiv., 0.252 mmol) slowly, and continue stirring for 1 hour. The reaction was worked up in 1N NaOH$_{(aq)}$ (10 mL) and dichloromethane (15 mL×3). The organic layers were collected, washed with brine solution (10 mL), and concentrated to afford the crude tert-butyl ((trans-4-(9-chloro-3-methyl-2-oxo-3,4-dihydropyrimido[5,4-c]quinolin-1(2H)-yl)cyclohexyl)methyl)(methyl)carbamate (3h), which was used in the next step without purification.

To a dichloromethane (1 mL) solution of tert-Butyl ((trans-4-(9-chloro-3-methyl-2-oxo-3,4-dihydropyrimido[5, 4-c]quinolin-1(2H)-yl)cyclohexyl)methyl)(methyl)carbamate (3h, 1.0 equiv., 0.063 mmol) was added 0.1 mL of trifluoroacetic acid. Stir for an hour, and remove the solvent under reduced pressure. Purification was performed by Flash Column Chromatography on silica gel with 0-20% $CH_2Cl_2$/methanol (1.75N ammonia) gradient to afford the compound 9-chloro-3-methyl-1-(trans-4-((methylamino)methyl)cyclohexyl)-3,4-dihydropyrimido[5,4-c]quinolin-2(1H)-one (3i). MS (ESI) calculated for $C_{20}H_{26}ClN_4O$ [M+H]$^+$, 373; found 373.

9-chloro-1-(trans-4-((dimethylamino)methyl)cyclohexyl)-3-methyl-3,4-dihydropyrimido[5,4-c]quinolin-2(1H)-one (3j)

To a methanol (0.5 mL) solution containing 9-chloro-3-methyl-1-(trans-4-((methylamino)methyl)cyclohexyl)-3,4-dihydropyrimido[5,4-c]quinolin-2(1H)-one (3i, 1 equiv., 0.024 mmol) was added paraformaldehyde (3.0 equiv., 0.072 mmol) and a drop of acetic acid. The mixture was stirred for 30 min at room temperature, and added with sodium cyanoborohydride (3.0 equiv., 0.072 mmol). Continue stirring at room temperature overnight. The reaction was worked up in water (10 mL) and CHCl$_3$:iPrOH (4:1) (15 mL×3). Purification was performed by Flash Column Chromatography on silica gel with 0-20% CH₂Cl₂/methanol (1.75N ammonia) gradient to afford the compound 9-chloro-1-(trans-4-((dimethylamino)methyl)cyclohexyl)-3-methyl-3,4-dihydropyrimido[5,4-c]quinolin-2(1H)-one (3j). MS (ESI) calculated for $C_{21}H_{28}ClN_4O$ [M+H]⁺, 387; found 387.

9-(3,5-dichloro-4-hydroxyphenyl)-1-(trans-4-((dimethylamino)methyl)cyclohexyl)-3-methyl-3,4-dihydropyrimido[5,4-c]quinolin-2(1H)-one (02-095)

In a 1,4-dioxane/sat. Na₂CO₃(aq)(3:1) solution (0.8 mL) containing 9-chloro-1-(trans-4-((dimethylamino)methyl)cyclohexyl)-3-methyl-3,4-dihydropyrimido[5,4-c]quinolin-2(1H)-one (3j, 1.0 equiv., 0.014 mmol) was added (3,5-dichloro-4-hydroxyphenyl)boronic acid (1.5 equiv., 0.021 mmol) and 2-di-tert-butylphosphino-2',4',6'-triisopropylbiphenyl (10% equiv., 0.0014 mmol). The reaction was purged thoroughly with argon, to which 10% equivalent of bis(tripheylphosphine)palladium(II) dichloride (0.0014 mmol) was added. The reaction was heated to 85° C. and continue stirring for 2 hours. The reaction was worked up in water (10 mL) and CHCl₃:iPrOH (4:1) (15 mL×3). The organic layers were collected and washed with brine solution (10 mL). The solvent was removed under reduced pressure, and the crude was purified by reverse-phase prep-HPLC (C18) using water (0.05% trifluoroacetic acid)/methanol (0.05% trifluoroacetic acid) gradient to afford compound 02-095 as a trifluoroacetic salt.

Compound 02-095. ¹H NMR (400 MHz, DMSO) δ 10.60-10.42 (br, 1H), 9.06 (s, 1H), 8.72 (s, 1H), 8.13 (d, J=8.8 Hz, 1H), 8.08 (d, J=8.8 Hz, 1H), 8.05 (s, 1H), 7.82 (s, 2H), 4.51 (s, 2H), 3.83 (m, 1H), 2.93 (s, 3H), 2.89 (t, J=6.1 Hz, 2H), 2.77 (s, 3H), 2.76 (s, 3H), 2.58 (m, 2H), 2.14 (m, 2H), 1.85 (m, 2H), 1.79 (m, 1H), 1.07 (m, 2H). Calculated mass: 512.175. Observed mass: 513. MELK IC₅₀ as determined by Z'-LYTE® biochemical assay: 27.1 nM. TFA salt.

Compound 02-096 was synthesized in a manner analogous to 02-095, using 4,6-dichloro-1,5-naphthyridine-3-carboxylate.

Compound 02-096

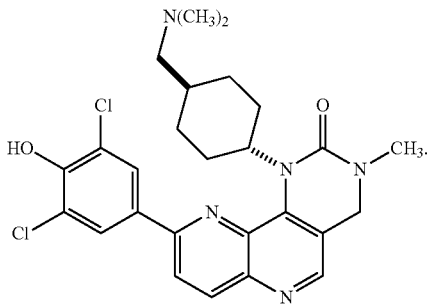

¹H NMR (400 MHz, DMSO) δ 10.80-10.68 (br, 1H), 9.04 (s, 1H), 8.69 (s, 1H), 8.41 (d, J=9.0 Hz, 1H), 8.36 (d, J=9.0 Hz, 1H), 8.21 (s, 2H), 4.55 (tt, J=11.7, 3.5 Hz, 1H), 4.50 (s, 2H), 2.93 (s, 3H), 2.89 (t, J=6.1 Hz, 2H), 2.77 (s, 3H), 2.76 (s, 3H), 2.60 (m, 2H), 2.23 (m, 2H), 1.87 (m, 2H), 1.78 (m, 1H), 1.00 (m, 2H). Calculated mass: 513.17. Observed mass: 514. MELK IC₅₀: 2.8. TFA salt.

Example 6

Scheme 4. Synthetic Scheme for 02-022.

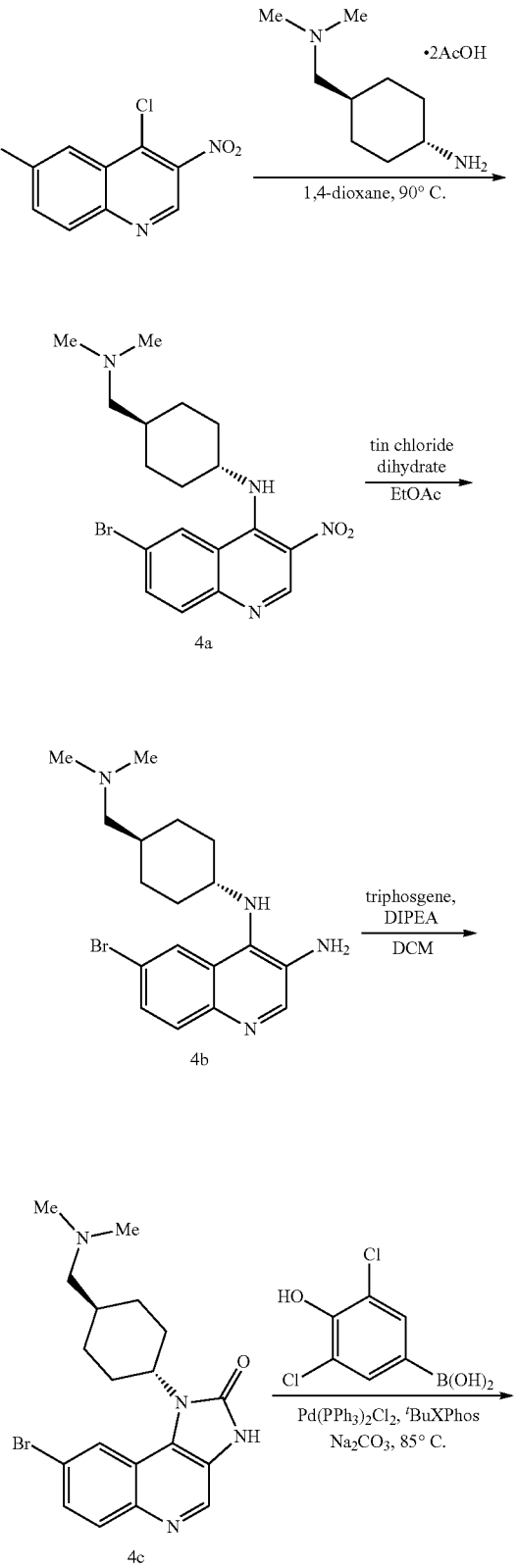

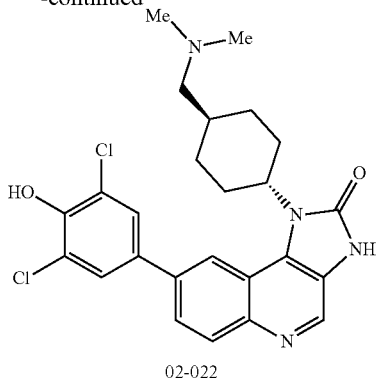

02-022

6-bromo-N⁴-(trans-4-((dimethylamino)methyl)cyclohexyl)quinoline-3,4-diamine (4b)

In a stirring 1,4-dioxane solution (5 ml) of 6-bromo-4-chloro-3-nitroquinoline (1 equiv., 0.537 mmol), trans-4-((dimethylamino)methyl)cyclohexan-1-amine diacetic acid (1 equiv., 0.537 mmol) and N,N-diisopropylethylamine (10 equiv., 5.37 mmol) were added and allowed to dissolve. The resulting solution was heated up to 90° C., and stirred for 12 hours before cooling to room temperature. The solvent was removed under reduced pressure, and worked up in sat. $NaHCO_{3(aq)}$ (10 mL) and ethyl acetate (15 mL×3). The organic layers were collected, and concentrated to afford the crude product 6-bromo-N-(trans-4-((dimethylamino)methyl)cyclohexyl)-3-nitroquinolin-4-amine (4a), which was used in the next step without further purification.

To an ethyl acetate (10 mL) solution containing 6-bromo-N-(trans-4-((dimethylamino)methyl)cyclohexyl)-3-nitroquinolin-4-amine (4a, 1.0 equiv., 0.354 mmol) was added tin chloride dihydrate (5.0 equiv., 1.77 mmol). The reaction mixture was heated to 70° C. and stirred overnight. The mixture was extracted with sat. $NaHCO_{3(aq)}$ (10 mL) and $CHCl_3$:iPrOH (4:1) (20 mL×3). Purification was performed by Flash Column Chromatography on silica gel with 0-20% $CH_2Cl_2$/methanol (1.75N ammonia) gradient to afford the compound 6-bromo-N⁴-(trans-4-((dimethylamino)methyl)cyclohexyl)quinoline-3,4-diamine (4b). MS (ESI) calculated for $C_{18}H_{26}BrN_4$ $[M+H]^+$, 377; found 377.

8-bromo-1-(trans-4-((dimethylamino)methyl)cyclohexyl)-1,3-dihydro-2H-imidao[4,5-c]quinolin-2-one (4c)

To a dichloromethane (1 mL) solution containing 6-bromo-N⁴-(trans-4-((dimethylamino)methyl)cyclohexyl)quinoline-3,4-diamine (4b, 1.0 equiv., 0.090 mmol) and diisopropylethylamine (5.0 equiv., 0.45 mmol) in ice bath was added triphosgene (1.0 equiv., 0.090 mmol). Stir for 1 hour. Remove the solvent under reduced pressure. Purification was performed by Flash Column Chromatography on silica gel with 0-20% $CH_2Cl_2$/methanol (1.75N ammonia) gradient to afford the compound 8-bromo-1-(trans-4-((dimethylamino)methyl)cyclohexyl)-1,3-dihydro-2H-imidazo[4,5-c]quinolin-2-one (4c). MS (ESI) calculated for $C_{19}H_{24}BrN_4O$ $[M+H]^+$, 403; found 403.

8-(3,5-dichloro-4-hydroxyphenyl)-1-(trans-4-((dimethylamino)methyl)cyclohexyl)-1,3-dihydro-2H-imidazo[4,5-c]quinolin-2-one (02-022)

In a 1,4-dioxane/sat. $Na_2CO_3(aq)$(3:1) solution (0.8 mL) containing 8-bromo-1-(trans-4-((dimethylamino)methyl)cyclohexyl)-1,3-dihydro-2H-imidazo[4,5-c]quinolin-2-one (4c, 1.0 equiv., 0.025 mmol) was added (3,5-dichloro-4-hydroxyphenyl)boronic acid (1.5 equiv., 0.037 mmol) and 2-di-tert-butylphosphino-2',4',6'-triisopropylbiphenyl (10% equiv., 0.0025 mmol). The reaction was purged thoroughly with argon, to which 10% equivalent of bis(tripheylphosphine)palladium(II) dichloride (0.0025 mmol) was added. The reaction was heated to 85° C. and continue stirring for 2 hours. The reaction was worked up in water (10 mL) and $CHCl_3$:iPrOH (4:1) (15 mL×3). The organic layers were collected and washed with brine solution (10 mL). The solvent was removed under reduced pressure, and the crude was purified by reverse-phase prep-HPLC (C18) using water (0.05% trifluoroacetic acid)/methanol (0.05% trifluoroacetic acid) gradient to afford the compound 02-022 as a trifluoroacetic salt.

Compound 02-022. ¹H NMR (400 MHz, DMSO) δ 11.88 (s, 1H), 10.62-10.44 (br, 1H), 9.33-9.22 (br, 1H), 8.80 (s, 1H), 8.30 (s, 1H), 8.14 (d, J=9.0 Hz, 1H), 8.07 (d, J=9.0 Hz, 1H), 7.87 (s, 2H), 4.88 (tt, J=11.9, 3.5 Hz, 1H), 2.99 (t, J=5.7 Hz, 2H), 2.84 (s, 3H), 2.83 (s, 3H), 2.57 (m, 2H), 2.10 (m, 2H), 1.99 (m, 2H), 1.90 (m, 1H), 1.28 (m, 2H). Calculated mass: 484.143. Observed mass: 485. MELK $IC_{50}$ as determined by Z'-LYTE® biochemical assay: 1.85 nM. TFA salt.

Example 7

Scheme 5: Synthesis Scheme for 02-084.

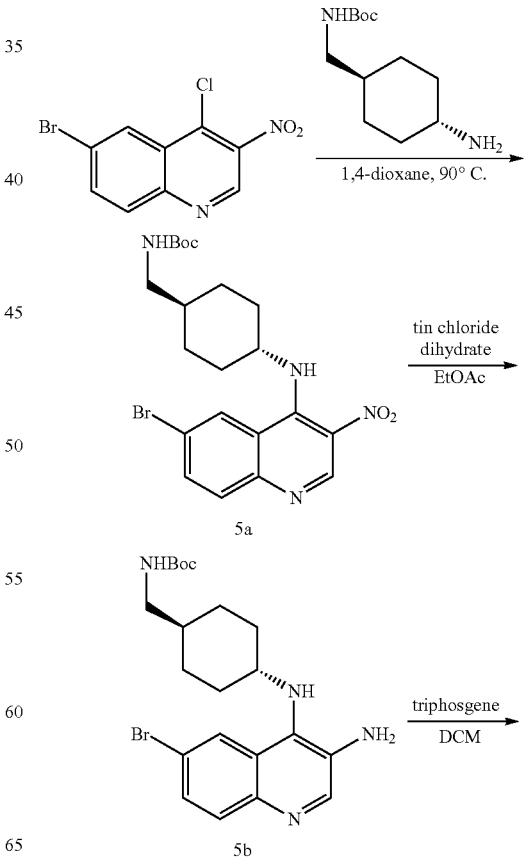

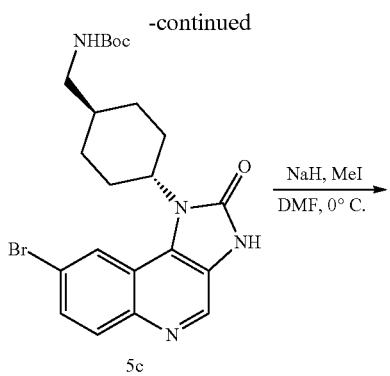

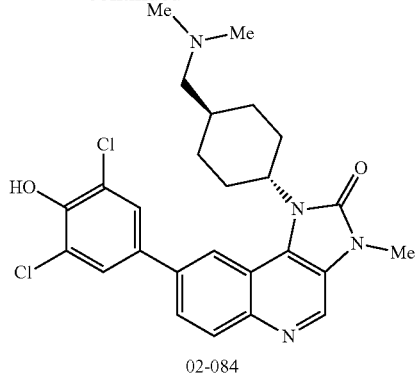

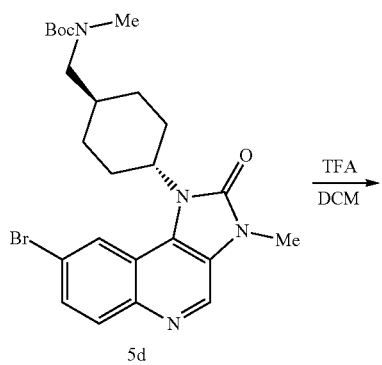

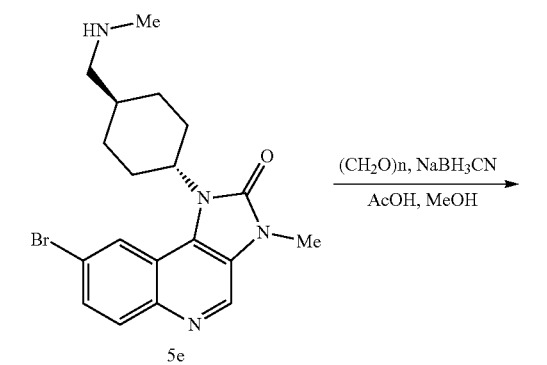

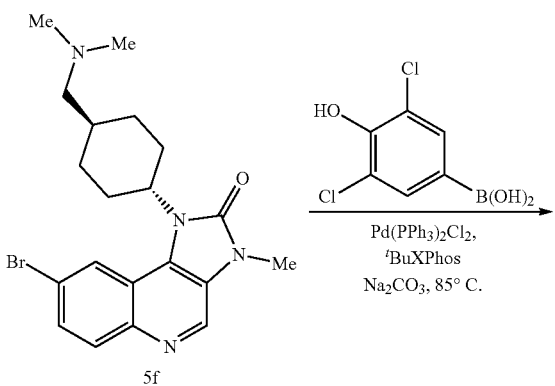

tert-butyl ((trans-4-((3-amino-6-bromoquinolin-4-yl)amino)cyclohexyl)methyl)carbamate (5b)

In a stirring tert-butanol solution (2 ml) of 6-bromo-4-chloro-3-nitroquinoline (1.0 equiv., 0.193 mmol), tert-butyl ((trans-4-aminocyclohexyl)methyl)carbamate (1.1 equiv., 0.212 mmol) and potassium carbonate (3.0 equiv., 0.579 mmol) were added and allowed to dissolve. The resulting solution was heated up to 90° C., and stirred for 12 hours before cooling to room temperature. The reaction mixture was filtered through cotton, and worked up in sat. $NaHCO_{3(aq)}$ (10 mL) and ethyl acetate (15 mL×3). The organic layers were collected, and concentrated to afford the crude product tert-butyl ((trans-4-((6-bromo-3-nitroquinolin-4-yl)amino)cyclohexyl)methyl)carbamate (5a), which was used in the next step without further purification.

To a pyridine/ethyl acetate (1:9, 1.5 mL) solution containing tert-butyl ((trans-4-((6-bromo-3-nitroquinolin-4-yl)amino)cyclohexyl)methyl)carbamate (5a, 1.0 equiv., 0.075 mmol) was added tin chloride dihydrate (5.0 equiv., 0.375 mmol). The reaction mixture was heated to 70° C. and stirred overnight. The mixture was extracted with sat. $NaHCO_{3(aq)}$ (10 mL) and $CHCl_3$:iPrOH (4:1) (20 mL×3). Purification was performed by Flash Column Chromatography on silica gel with 0-20% $CH_2Cl_2$/methanol (1.75N ammonia) gradient to afford the compound tert-butyl ((trans-4-((3-amino-6-bromoquinolin-4-yl)amino)cyclohexyl)methyl)carbamate (5b). MS (ESI) calculated for $C_{21}H_{30}BrN_4O_2$ $[M+H]^+$, 449; found 449.

tert-butyl ((trans-4-(8-bromo-2-oxo-2,3-dihydro-1H-imidazo[4,5-c]quinolin-1-yl)cyclohexyl)methyl)carbamate (5c)

To a dichloromethane (3 mL) solution containing tert-butyl ((trans-4-((3-amino-6-bromoquinolin-4-yl)amino)cyclohexyl)methyl)carbamate (5b, 1.0 equiv., 0.075 mmol) and triethylamine (10.0 equiv., 0.75 mmol) in ice bath was added triphosgene (1.0 equiv., 0.075 mmol). Stir for 1 hour. Remove the solvent under reduced pressure, and extract the mixture using sat. $NaHCO_{3(aq)}$ (10 mL) and dichloromethane (20 mL×3). Purification was performed by Flash Column Chromatography on silica gel with 0-10% $CH_2Cl_2$/methanol (1.75N ammonia) gradient to afford the compound tert-butyl ((trans-4-(8-bromo-2-oxo-2,3-dihydro-1H-imidazo[4,5-c]quinolin-1-yl)cyclohexyl)methyl)carbamate (5c). MS (ESI) calculated for $C_{22}H_{28}BrN_4O_3$ $[M+H]^+$, 475; found 475.

8-bromo-3-methyl-1-(trans-4-((methylamino) methyl)cyclohexyl)-1,3-dihydro-2H-imidazo[4,5-c] quinolin-2-one (5e)

To a stirring solution of N,N-dimethylformamide solution containing tert-butyl ((trans-4-(8-bromo-2-oxo-2,3-dihydro-1H-imidazo[4,5-c]quinolin-1-yl)cyclohexyl)methyl)carbamate (5c, 1.0 equiv., 0.032 mmol) in an ice bath was added methyl iodide (4.0 equiv., 0.128 mmol). To the reaction mixture was added sodium hydride (4.0 equiv., 0.128 mmol) slowly, and continue stirring for 1 hour. The reaction was worked up in 1N NaOH$_{(aq)}$ (10 mL) and dichloromethane (15 mL×3). The organic layers were collected, washed with brine solution (10 mL), and concentrated to afford the crude tert-butyl ((trans-4-(8-bromo-3-methyl-2-oxo-2,3-dihydro-1H-imidazo[4,5-c]quinolin-1-yl)cyclohexyl)methyl)(methyl)carbamate (5d), which was used in the next step without purification.

To a dichloromethane (1 mL) solution of tert-butyl ((trans-4-(8-bromo-3-methyl-2-oxo-2,3-dihydro-1H-imidazo[4,5-c]quinolin-1-yl)cyclohexyl)methyl)(methyl)carbamate (5d, 1.0 equiv., 0.032 mmol) was added 0.1 mL of trifluoroacetic acid. Stir for an hour, and remove the solvent under reduced pressure. Purification was performed by Flash Column Chromatography on silica gel with 0-20% CH$_2$Cl$_2$/methanol (1.75N ammonia) gradient to afford the compound 8-bromo-3-methyl-1-(trans-4-((methylamino)methyl)cyclohexyl)-1,3-dihydro-2H-imidazo[4,5-c]quinolin-2-one (5e). MS (ESI) calculated for C$_{19}$H$_{24}$BrN$_4$O [M+H]$^+$, 403; found 403.

8-bromo-1-(trans-4-((dimethylamino)methyl)cyclohexyl)-3-methyl-1,3-dihydro-2H-imidazo[4,5-c]quinolin-2-one (5f)

To a methanol (1 mL) solution containing 8-bromo-3-methyl-1-(trans-4-((methylamino)methyl)cyclohexyl)-1,3-dihydro-2H-imidazo[4,5-c]quinolin-2-one (5e, 1 equiv., 0.05 mmol) was added paraformaldehyde (3.0 equiv., 0.15 mmol) and a drop of acetic acid. The mixture was stirred for 30 min at room temperature, and added with sodium cyanoborohydride (3.0 equiv., 0.15 mmol). Continue stirring at room temperature overnight. The reaction was worked up in water (10 mL) and CHCl$_3$:iPrOH (4:1) (15 mL×3). Purification was performed by Flash Column Chromatography on silica gel with 0-20% CH$_2$Cl$_2$/methanol (1.75N ammonia) gradient to afford the compound 8-bromo-1-(trans-4-((dimethylamino)methyl)cyclohexyl)-3-methyl-1,3-dihydro-2H-imidazo[4,5-c]quinolin-2-one (5f). MS (ESI) calculated for C$_{20}$H$_{26}$BrN$_4$O [M+H]$^+$, 417; found 417.

8-(3,5-dichloro-4-hydroxyphenyl)-1-(trans-4-((dimethylamino)methyl)cyclohexyl)-3-methyl-1,3-dihydro-2H-imidazo[4,5-c]quinolin-2-one (02-084)

In a 1,4-dioxane/sat. Na$_2$CO$_3$(aq)(3:1) solution (0.8 mL) containing 8-bromo-1-(trans-4-((dimethylamino)methyl)cyclohexyl)-3-methyl-1,3-dihydro-2H-imidazo[4,5-c]quinolin-2-one (5f, 1.0 equiv., 0.018 mmol) was added (3,5-dichloro-4-hydroxyphenyl)boronic acid (1.5 equiv., 0.027 mmol) and 2-di-tert-butylphosphino-2',4',6'-triisopropylbiphenyl (10% equiv., 0.0018 mmol). The reaction was purged thoroughly with argon, to which 10% equivalent of bis(tripheylphosphine)palladium(II) dichloride (0.0018 mmol) was added. The reaction was heated to 85° C. and continue stirring for 2 hours. The reaction was worked up in water (10 mL) and CHCl$_3$:iPrOH (4:1) (15 mL×3). The organic layers were collected and washed with brine solution (10 mL). The solvent was removed under reduced pressure, and the crude was purified by reverse-phase prep-HPLC (C18) using water (0.05% trifluoroacetic acid)/methanol (0.05% trifluoroacetic acid) gradient to afford the compound 02-084 as a trifluoroacetic salt.

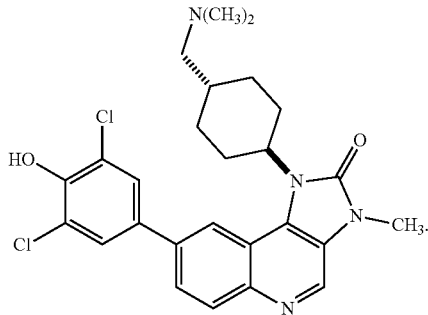

Compound 02-084

$^1$H NMR (400 MHZ, DMSO) δ 10.61-10.40 (br, 1H), 9.33-9.18 (br, 1H), 9.01 (s, 1H), 8.31 (s, 1H), 8.16 (d, J=9.0 Hz, 1H), 8.07 (d, J=9.0 Hz, 1H), 7.88 (s, 2H), 4.92 (m, 1H), 3.52 (s, 3H), 3.00 (t, J=5.5 Hz, 2H), 2.84 (s, 3H), 2.83 (s, 3H), 2.56 (m, 2H), 2.11 (m, 2H), 2.00 (m, 2H), 1.91 (m, 1H), 1.29 (m, 2H). Calculated mass: 498.159. Observed mass: 499. MELK IC$_{50}$ as determined by Z'-LYTE® biochemical assay: 2.16 nM. TFA salt.

Generally, IC$_{50}$ against MELK was determined by Z'-LYTE® biochemical assay and are measured in nM at 25 uM ATP concentration.

Example 8

To discover a selective MELK inhibitor, a few molecule scaffolds with the potential of binding to MELK were identified, including 2,4-disubstituted pyrimidines and benzonaphthyridinones. THZ-4-63-1 (FIG. 1A), a small molecule that inhibits MELK kinase activity with biochemical IC$_{50}$ value of 10.5 nM was discovered. To investigate if THZ-4-63-1 confers selective inhibition on MELK, we tested its effect on other mitotic kinases. In assays using recombinant kinases, MELK kinase activity was 20-fold more sensitive to THZ-4-63-1, than that of Aurora A, Aurora B, CDK1, or PLK1 (FIG. 1B). We also found that THZ-4-63-1 preferentially targets MELK than other AMPK family kinases including NUAK1, BRSK1, and MARK1 (FIG. 1B).

Figure 5:
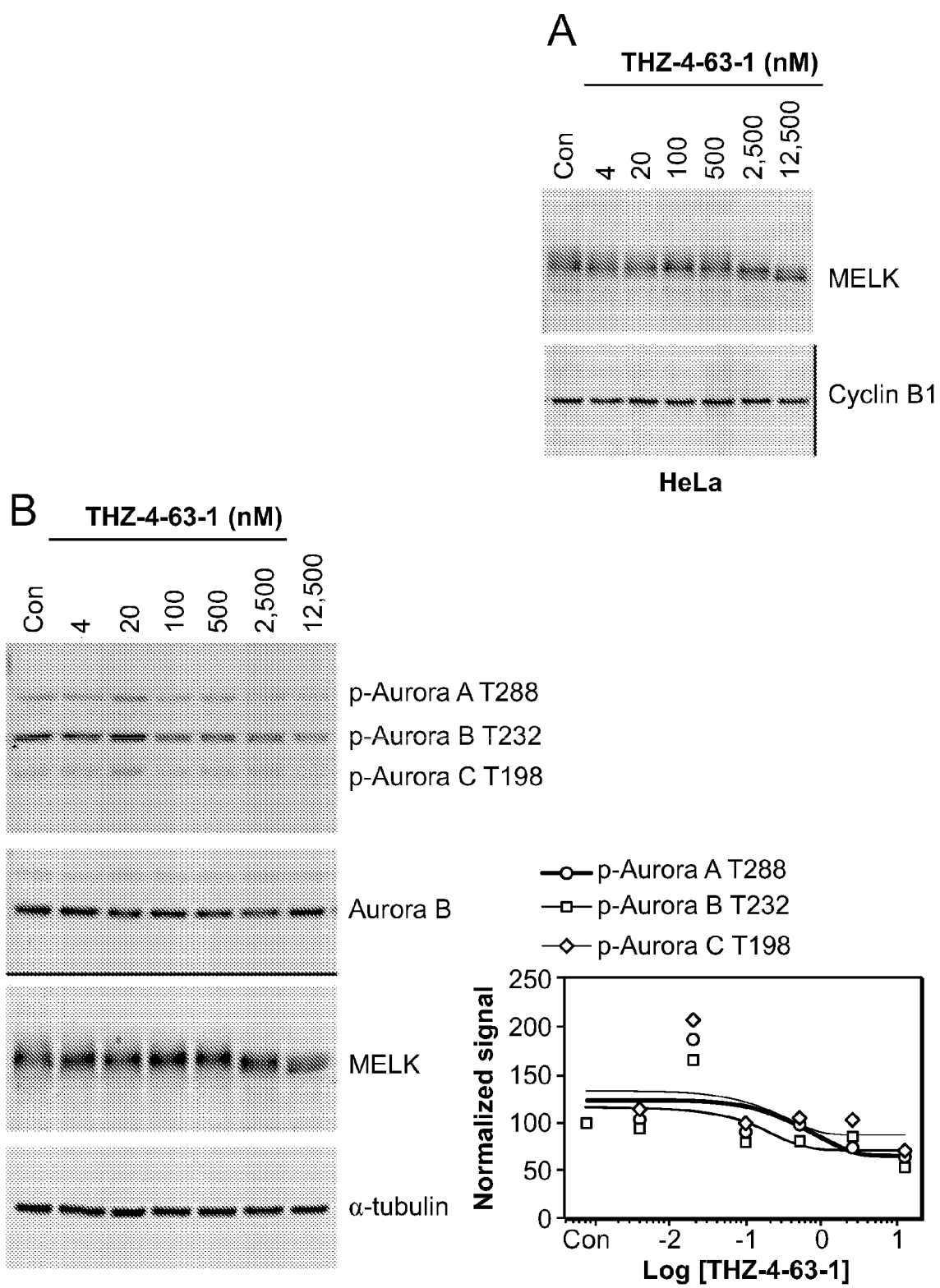
FIG. 5 demonstrates the unique characteristics of the electrophorectic mobility of MELK, and consists of Panels A-E. Nocodazole-arrested mitotic cells (HeLa cells in Panel A, MDA-MB-231 for the remaining panels) were treated for 30 min with increasing concentration of THZ-4-63-1 (Panels A and B), or VX-680 (Panel C), or MLN8054 (Panel D), or RO-3306 (Panel E). Cell lysates were subjected to immunoblotting. Panel A shows that THZ-4-63-1 treatment increases the electrophoretic mobility of mitotic MELK in HeLa cells. In Panel B, there is a lack of obvious inhibition on Aurora kinase phosphorylation by THZ-4-63-1. The fluorescent signals of immunblotting were quantified using Image Studio Lite software (Licor Biosciences, Lincoln, Neb.). The signal of phosphorylated Aurora kinases was normalized to that of loading control (α-tubulin). In Panels C and D, inhibition of Aurora kinases does not affect the electrophoretic mobility of MELK. Note that VX-580 or MLN8054 at doses that effectively suppresses the phosphorylation of Aurora kinases, does not alter the electrophoretic mobility of MELK. In Panel E, inhibiting CDK1 by the use of RO-3306 does not change the electrophoretic mobility of MELK.
Figure 5:
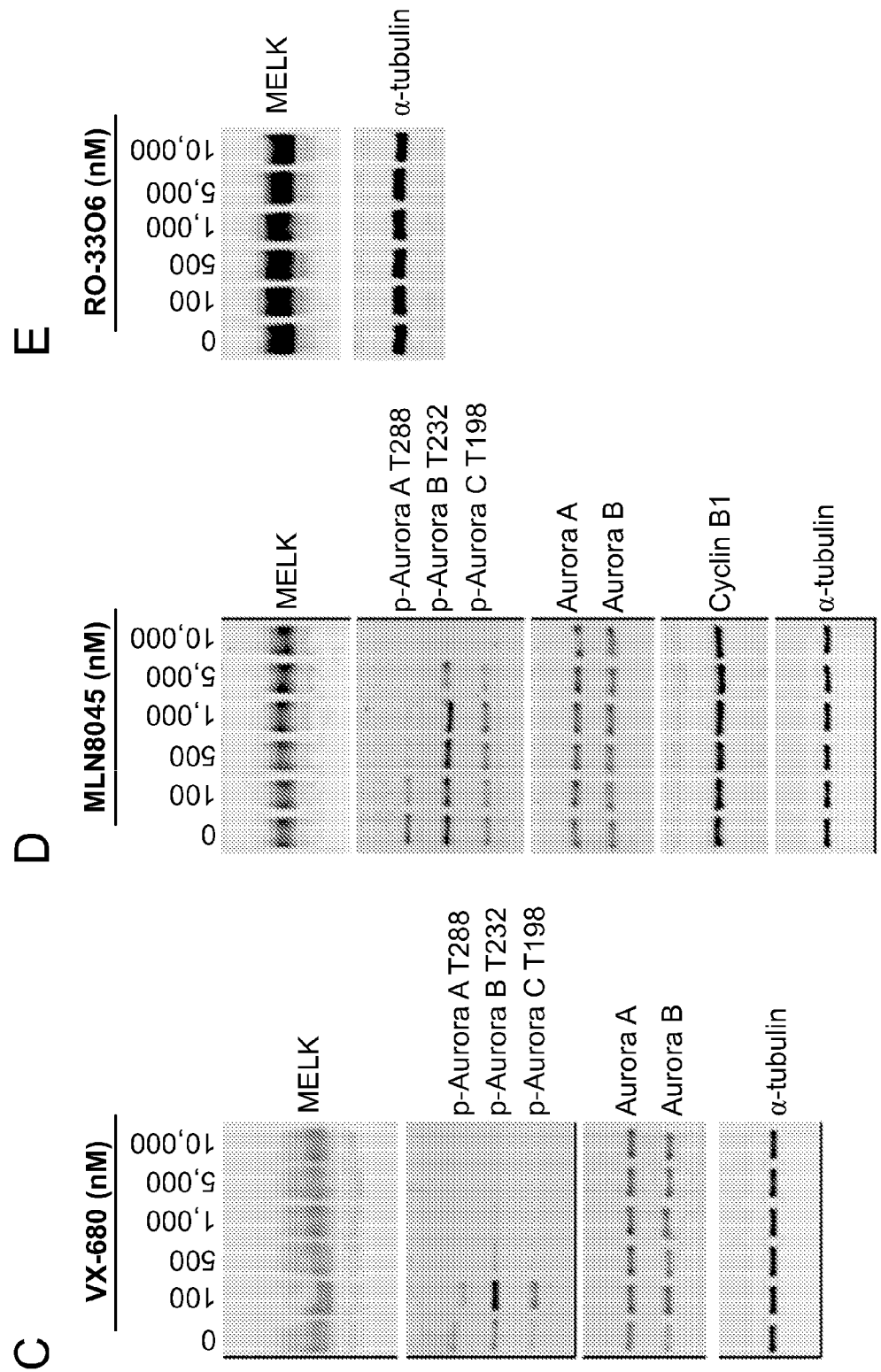
Figure 7:
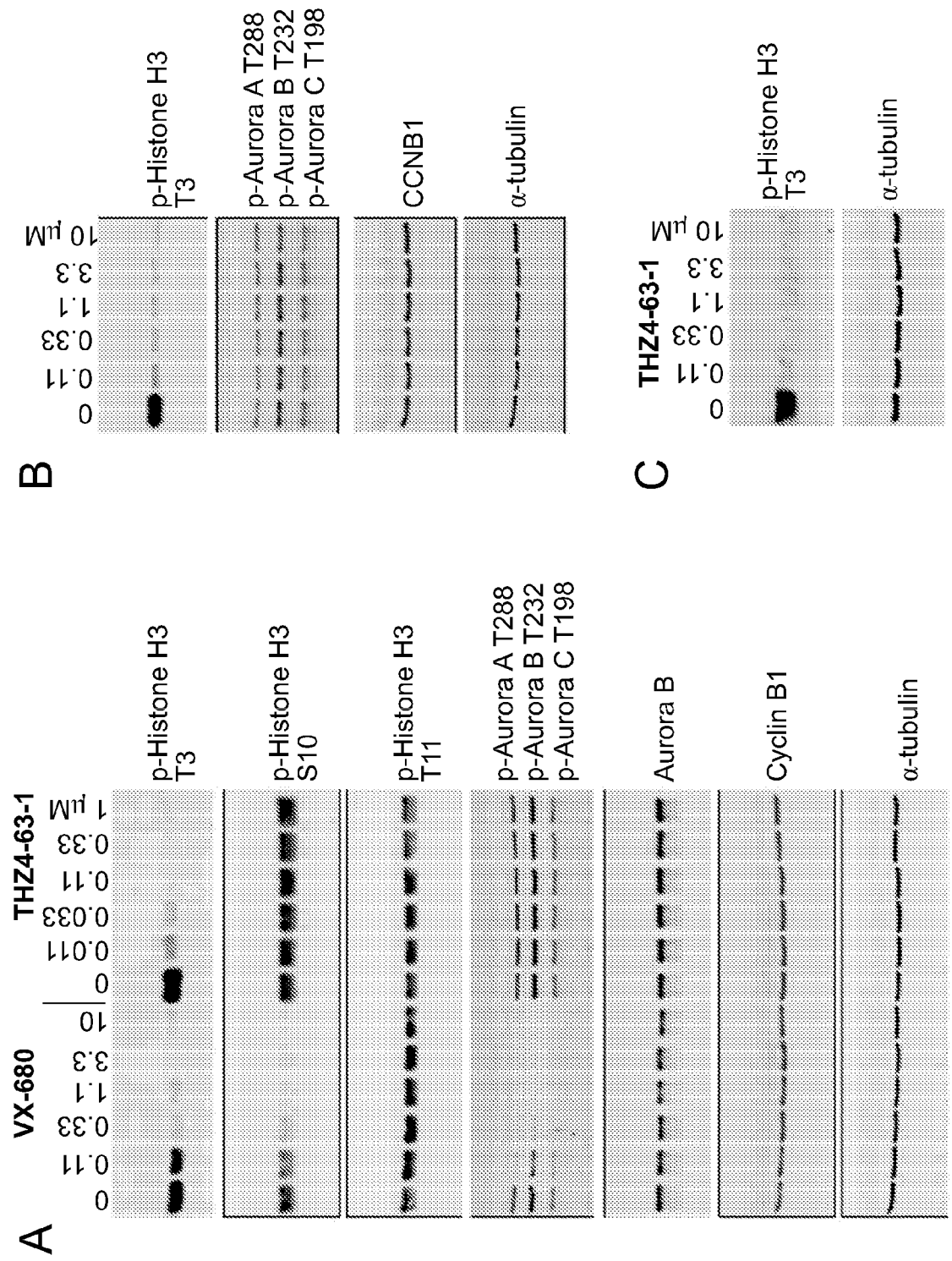
FIG. 7 presents that THZ04063-1 inhibits H3T3 phosphorylation, and consists of Panels A, B, C, and D. In Panel A, nocodazole-arrested mitotic MDA-MB-231 cells were treated for 30 min with THZ-4-63-1 or VX-680 at increasing concentrations, in the presence of nocodazole plus MG132. Cell lysates were prepared for immunoblotting. In Panels B and C, THZ-4-63-1 inhibits H3T3 phosphorylation in HeLa (B) and U2OS (C) cells. Nocodazole arrested mitotic cells were treated with THZ-4-63-1 at the indicated doses for 30 min. In Panel D, nocodazle-arrested mitotic cells were incubated with increasing concentrations of THZ-4-63-1 together with nocodazole and MG132 in the presence of absence of VX-680 (100 nM). Cell lysates were subjected to immunblotting. The signal of H3T3 phosphorylation was normalized to that of α-tubulin (right).
Figure 7:
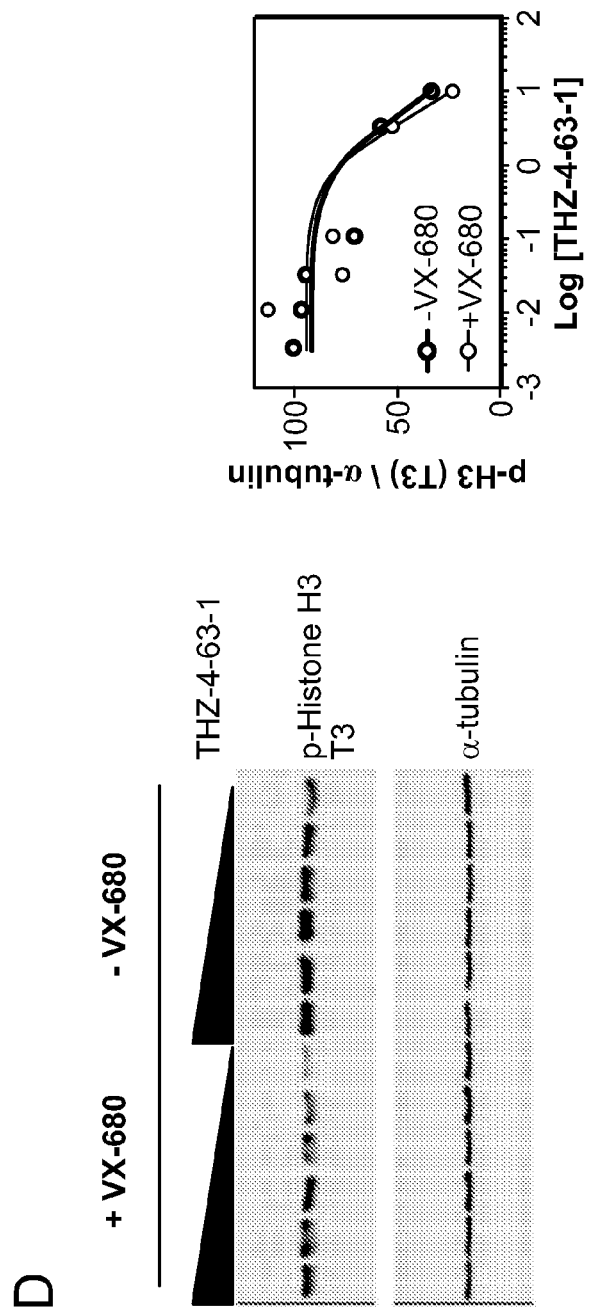

We next proceeded to test if THZ-4-63-1 inhibits MELK activity in vivo. With a lack of established kinase substrates of MELK during mitosis, we used the auto-phosphorylation of MELK as a surrogate to indicate the activity of MELK. Consistent with previous studies[1], mitotic MELK demonstrates a decreased electrophoretic mobility (FIG. 1C), a pattern that was efficiently restored by exposure to λ-phosphotase (FIG. 1D). Interestingly, the electrophoretic mobility of MELK was insensitive to the inhibitors of Aurora kinases or CDK1 (FIG. 5A-C), suggesting that MELK might not be subjected to regulation by those kinases. We then harvested nocodazole-arrested mitotic cells, and treated cells with increasing concentrations of THZ-4-63-1. Interestingly, in line with the notion of MELK auto-phosphorylation, the MELK inhibitor readily altered the mobility shift in a dose-dependent manner in multiple cell lines we tested (FIGS. 1E, 5D). In addition, consistent with selectivity of THZ-4-63-1 observed in vitro, treating mitotic cells with THZ-4-63-1 did not inhibit the phosphorylation of Aurora kinases (FIG. 5B, 7A). Together, these data indicate that THZ-4-63-1 causes a selective and potent inhibition on the activity of MELK in vivo.

Example 9

MELK Inhibition Delays Mitotic Progression.

Figure 2:
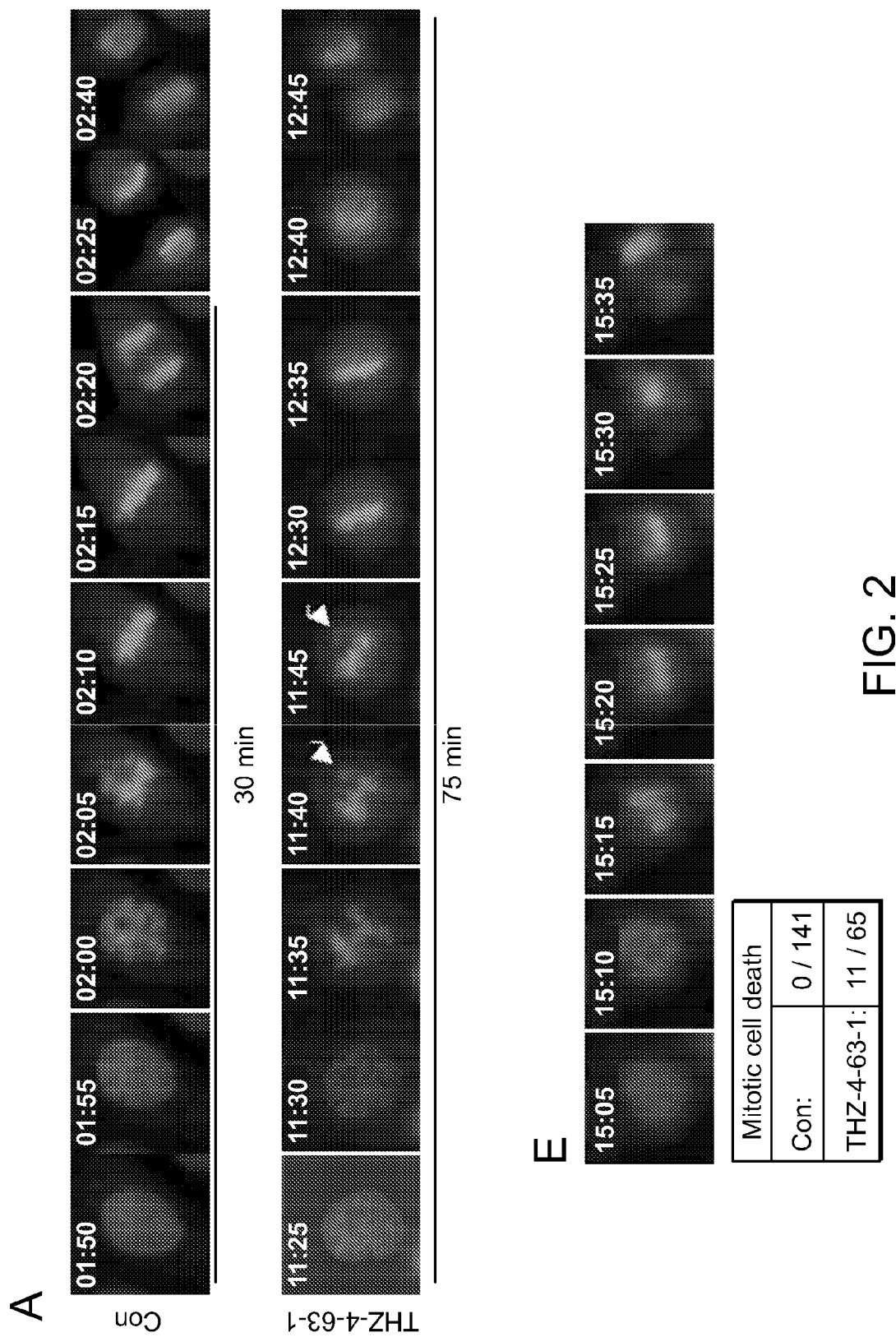
FIG. 2 contains images that demonstrate that MELK is required for chromosome alignment during mitosis, and consists of Panels A, B, C, D, E, and F. Panel A shows representative frames from time-lapse imaging. U2OS-GFP-H2B cells were treated with vehicle control (0.02% DMSO, v/v) or 1 μM THZ-4-63-1, and subjected to live imaging. Time is given in hours:minutes, relative to the initial time of drug treatment. The arrow points to chromosomes that haven't incorporated into the metaphase plate. Panel B shows a graph of time from nuclear envelope breakdown (NEBD) to anaphase onset in asynchronously growing U2OS cells, treated as in panel A. Panel C shows MELK knockdown delays mitotic progression. MDA-MB-468 cells expressing tet-on-shMELK and GFPH2B cells were treated with doxycycline for three days, before subjected to live imaging. Panel D contains images of immunoblotting of lysates from cells treated as in Panel C. Panel E contains images showing mitotic cell death in a cell treated with THZ-4-63-1. The table indicates the quantification of cell death events. Panel F contains images showing that treatment with THZ-4-63-1 impairs chromosome alignment. Cells were treated with DMSO control, or THZ-4-63-1 (5 μM) for 4 hours, followed by MG132 (10 μM) for 1 h. Cells were fixed and stained with anti-CREST, anti-α-tubulin, and DAPI to visualize chromosomes and kinetochores. The histogram indicates the quantifications of cells in metaphase with misaligned chromosomes.
Figure 2:
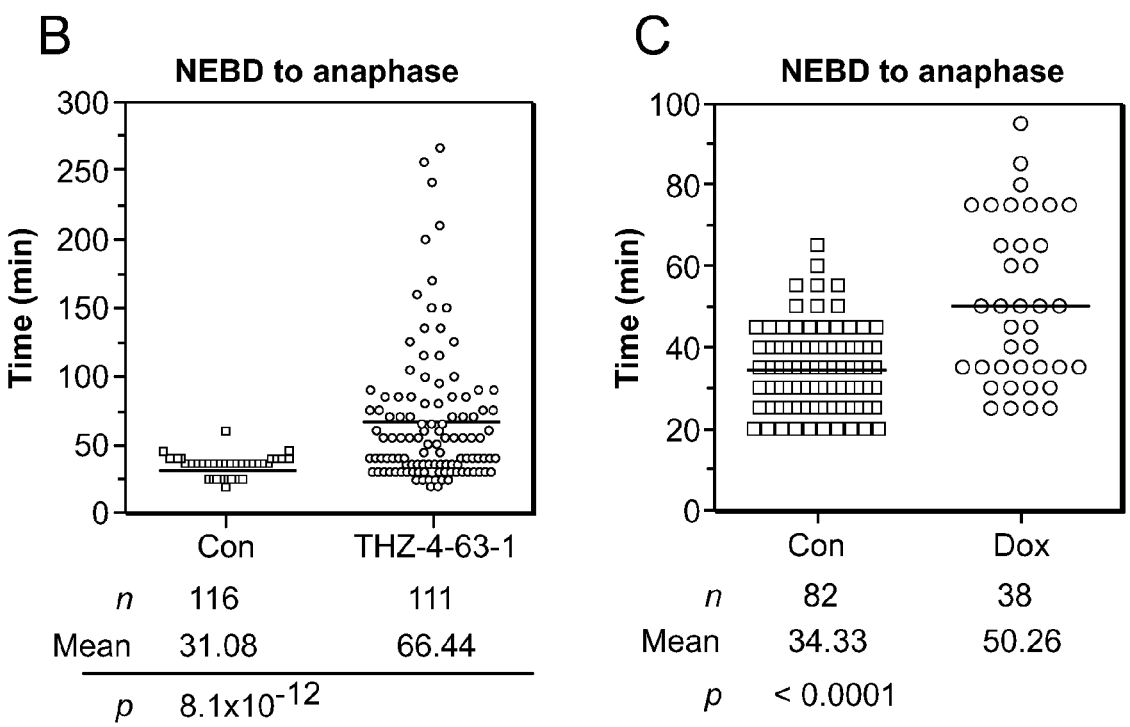
Figure 2:
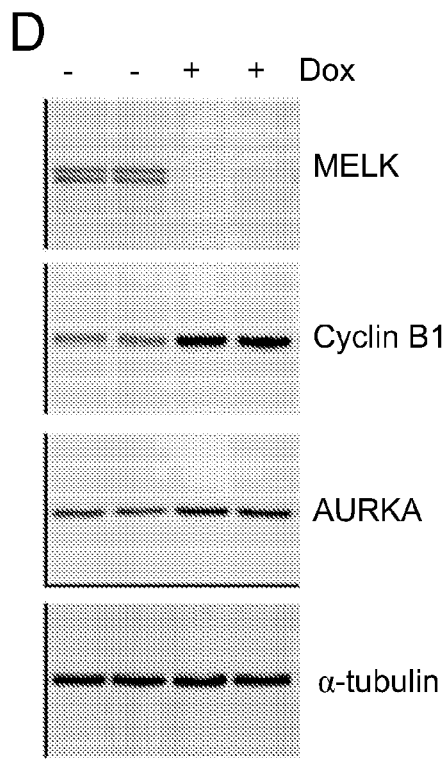
Figure 2:
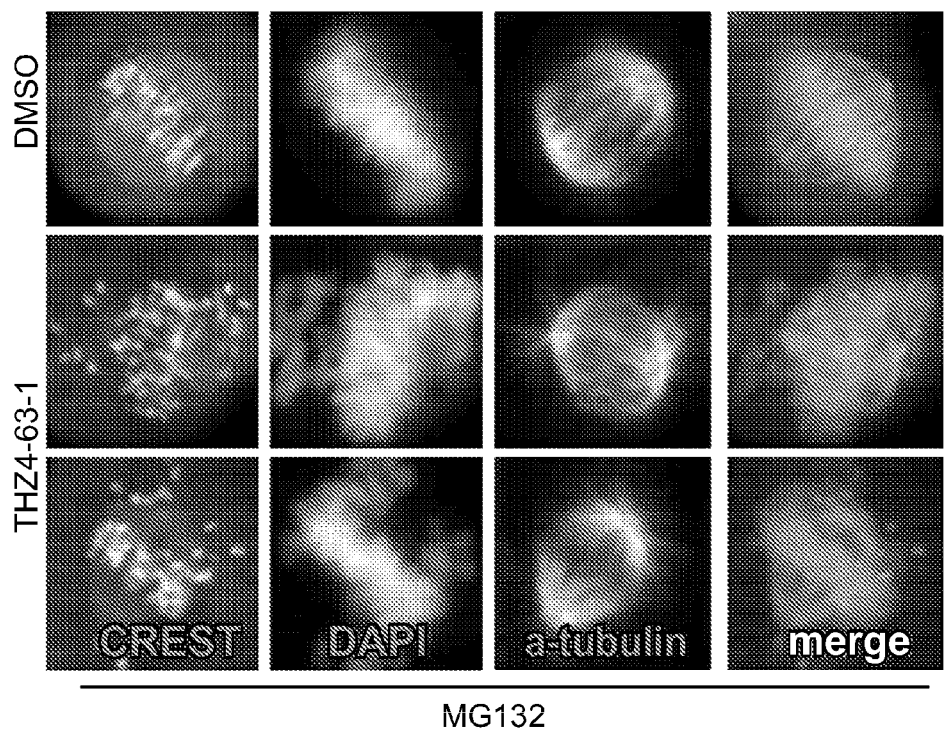
Figure 2:
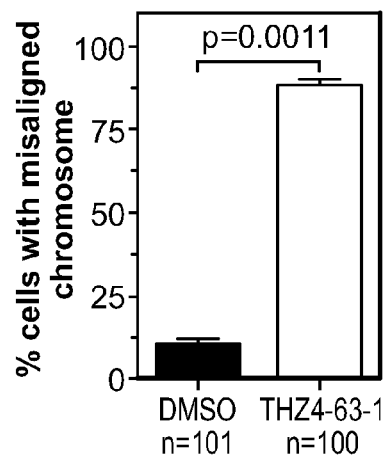
Figure 6:
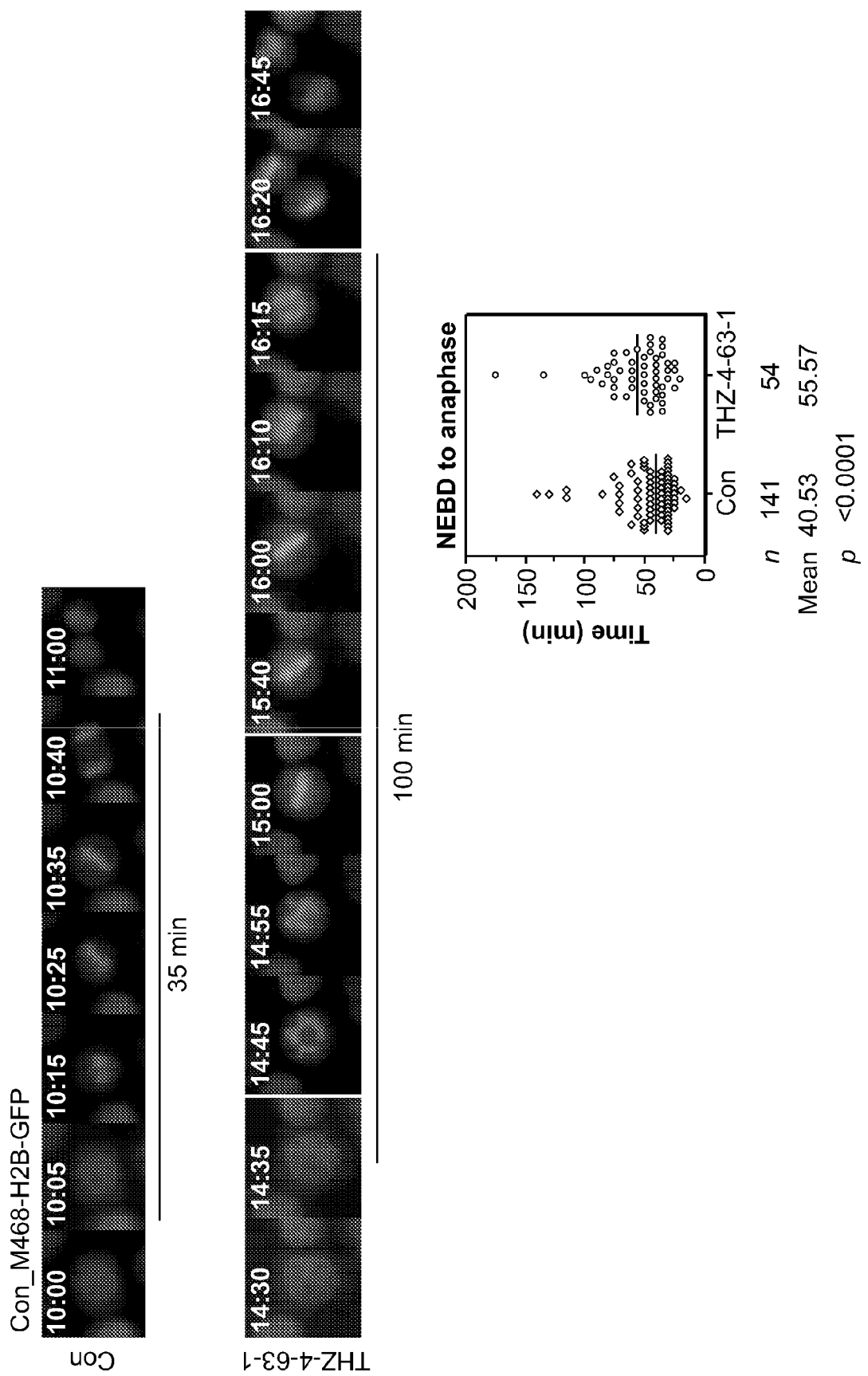
FIG. 6 shows that THZ-4-63-1 inhibits chromosome alignment in MDA-MB-468 cells. MDA-MB-468 cells stably expressing GFP-H2B were treated with vehicle control, or 1 µM THZ-4-63-1, and immediately subjected to live imaging. Time given in hours:minutes, relative to the starting point of treatment. The top of FIG. 6 shows frames from the time-lapse images. The bottom of FIG. 6 shows a histogram showing the time from nuclear envelope breakdown (NEBD) to anaphase onset. Each dot represent an individual mitotic event.

To utilize this novel compound for probing the roles of MELK in mitosis, we first treated asynchronized U2OS cells with THZ-4-63-1 (1 µM), and subjected the cells for live-cell imaging. The fusion protein GFP-Histone H2B was stably introduced into the cells to facilitate observing chromosome dynamics[2,7]. Interestingly, while control cells underwent mitosis at a normal kinetics, cells with MELK inhibited took longer time to form metaphase, and tended to pause at metaphase before the onset of chromosome segregation (FIG. 2A). In human osteosarcoma U2OS cells, THZ-4-63-1 induced a two-fold increase of the time from nuclear envelope breakdown (NEBD) to anaphase (mean of 31.1 vs 66.4 min; FIG. 2B). MELK inhibition also delayed mitotic progression in human breast cancer cell line, MDA-MB-468 (FIG. 6). In addition, we found that doxycycline-inducible knockdown of MELK also increased the duration from nuclear envelope breakdown to anaphase onset (mean of 34.3 vs 50.2 min; FIG. 2C-D), suggesting that the observed delay in mitotic progression upon THZ-4-63-1 treatment results from an on-target inhibition of MELK. Together, these findings indicate that MELK is novel regulator for the normal progression of mitosis, and that inactivation or depletion of MELK induces a metaphase-like arrest in cancer cells.

Perturbation of normal mitotic kinetic can lead to various cellular outcomes including cell death. We previously found that knocking down MELK in basal-like breast cancer cells induces cell death both during mitosis and in cells derived from failed cytokinesis[2]. Consistent with the observation based on genetic manipulation of MELK expression, THZ-4-63-1 efficiently induced mitotic cell death, an event that was often observed during or after the formation of metaphase plate (FIG. 2E).

MELK Inhibition Induces Chromosome Misalignment.

The delayed mitotic progression (including a potential defect in metaphase formation) upon MELK inhibition, suggest a role of MELK in regulating alignment of chromosome, a process that duplicated chromosomes form a bi-polar attachment to microtubule before an equal segregation of DNA can be achieved in anaphase. Indeed, we observed in asynchronized cells that MELK inhibition caused the appearance of scatted chromosome near the metaphase plate (arrowed, FIG. 2A). To investigate a potential role of MELK in regulating chromosome alignment, we treated cells with MELK inhibitor for 4 h followed by an additional 1 h with proteasome inhibitor, MG132, to allow cells sufficient time for chromosome alignment. Strikingly, while a majority of control cells had normal chromosome alignment, approximately 80% cells with MELK inhibited demonstrated a failure in metaphase chromosome alignment, forming a partial metaphase plate into which some chromosomes did not incorporate (FIG. 2F). In addition, the unaligned chromosome demonstrate doublets of centromere, suggesting mono-oriented pairs of sister chromatid (FIG. 2F, arrowed). These data suggest a role of MELK in regulating chromosome alignment, a mechanism that potentially explains for a delayed mitotic progression upon MELK inhibition.

Example 10

MELK Phosphorylates Histone H3 at Thr3.

Proper chromosome alignment relies on multiple factors and the associated post-translational modificationsr[8]. In particular, Aurora B kinase, the enzymatic component of the chromosome passenger complex (CPC), plays a central role. CPC is responsible for correcting erroneous attachment between microtubule and kinetochore, to form a bi-polar attachment allowing an equal distribution of duplicated chromosomes. This function of CPC requires the docking of the complex onto kinetochore, a process that was recently demonstrated to involve Haspin-mediated phosphorylation of Histone H3 at Thr3 (H3T3)[9,10]. Aurora B phosphorylates and activates Haspin to promote H3T3 phosphorylation leading to the chromosomal localization of CPC.

Figure 3:
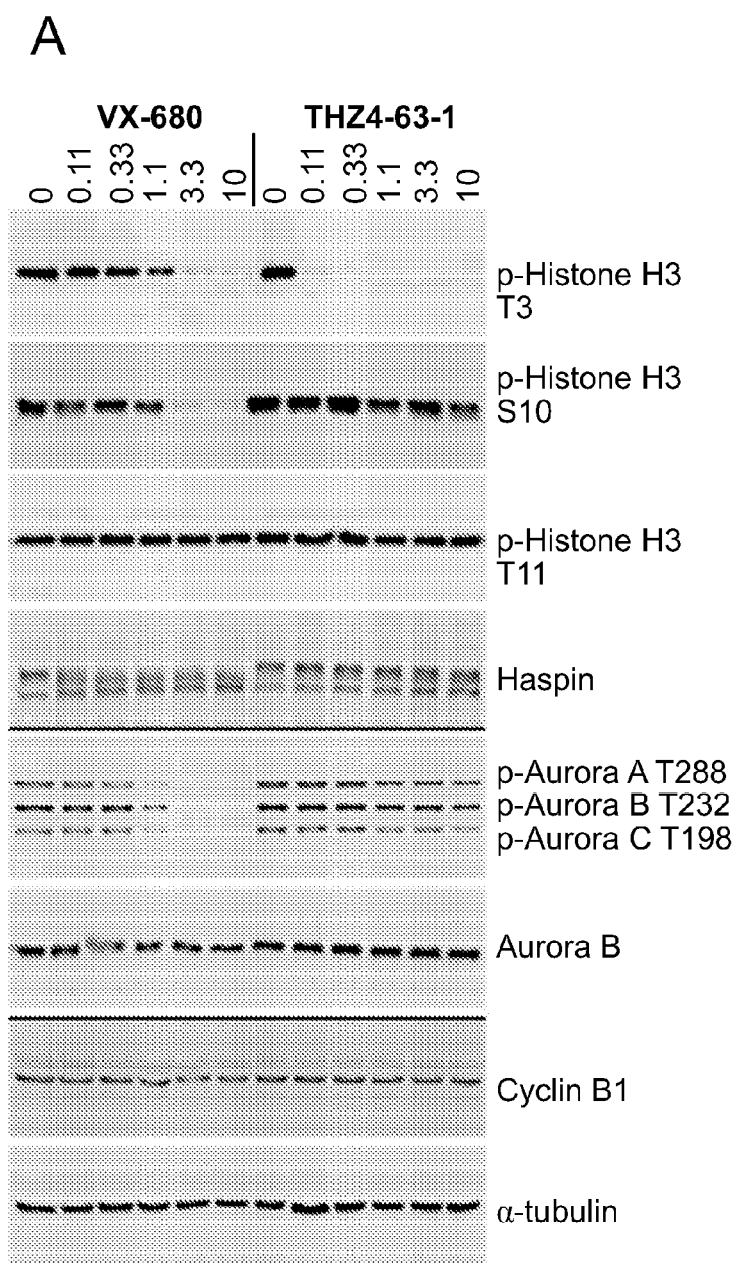
FIG. 3 contains images that indicate that MELK phosphorylates H3T3, and regulates localization of CPC, and contains panels A-I. Panel A shows that the MELK inhibitor suppresses H3T3 phosphorylation in an Aurora B-independent manner. Mitotic cells were treated for 30 min with THZ-4-63-1 or VX-680 at increasing concentrations, in the presence of paclitaxel (100 nM) and MG132 (10 µM). Cell lysates were prepared for immunoblotting. Panel B shows the results of an immunofluorescence assay of H3T3 phosphorylation. HeLa cells were treated with DMSO or THZ-4-63-1 (5 µM) for 4 h followed by 1 h treatment of MG132 (10 µM). Cells were fixed and stained with anti-H3T3ph and anti-CREST. Panel C shows that doxycycline-inducible MELK knockdown suppresses H3T3 phosphorylation. Cells were treated as in FIG. 2, Panel D, and additionally treated with MG132 (10 µM) for 1 h before fixation. The histogram indicates the quantification of H3S10ph signal. Panel D shows MELK overexpression increases H3T3 phosphorylation. MCF-10A cells stably expressing empty vector (EV) or MELK were fixed for immunostaining. Images were captured with identical exposure time. H3T3ph intensity was quantified by the use of ImageJ. Panel E shows that MELK phosphorylates H3 in vitro. Recombinant MELK protein (kinase domain) was incubated with recombinant Histone H3 for 30 min at 30° C. Samples were subjected to immunoblotting using the indicated antibodies. Panel F shows the localization of GFP-MELK during cell cycle. Cells stably expressing GFP-MELK were fixed by formaldehyde and stained with anti-H3S10ph. Panel G shows subcellular localization of endogenous MELK. Asynchronized (Async.) or nocodazole-arrested mitotic cells were subjected to fractionation, with sample prepared for immunoblotting. Panels H and I are images showing that MELK inhibition impairs the localization of chromosome passenger complex (CPC), indicated by the immunofluorescence detecting Survivin (G) and Aurora B (H). In addition to the presence of doxycyclin or THZ-4-63-1, cells were treated with nocodazole (0.33 µM) and MG132 (10 µM) for 3 h before fixation.
Figure 3:
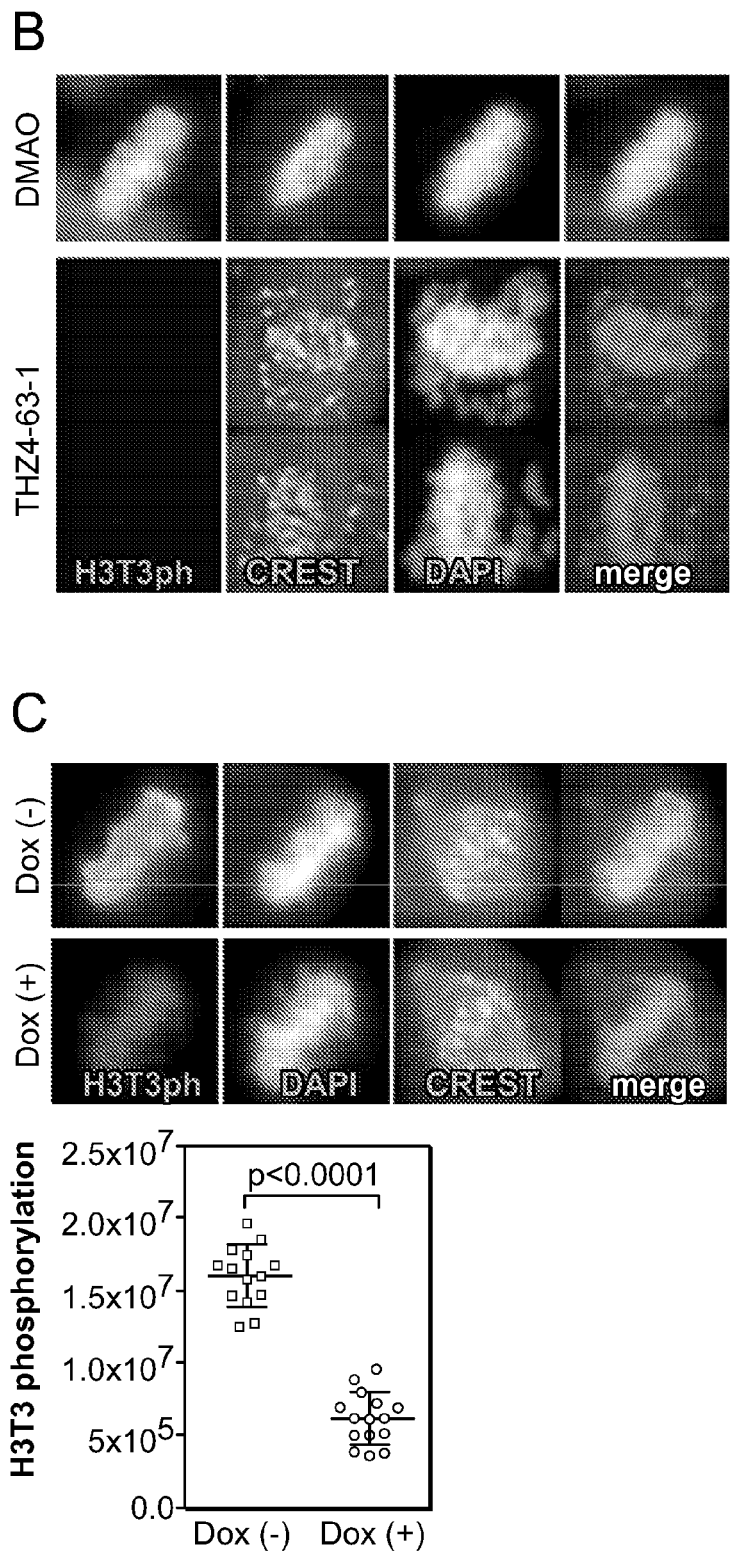
Figure 3:
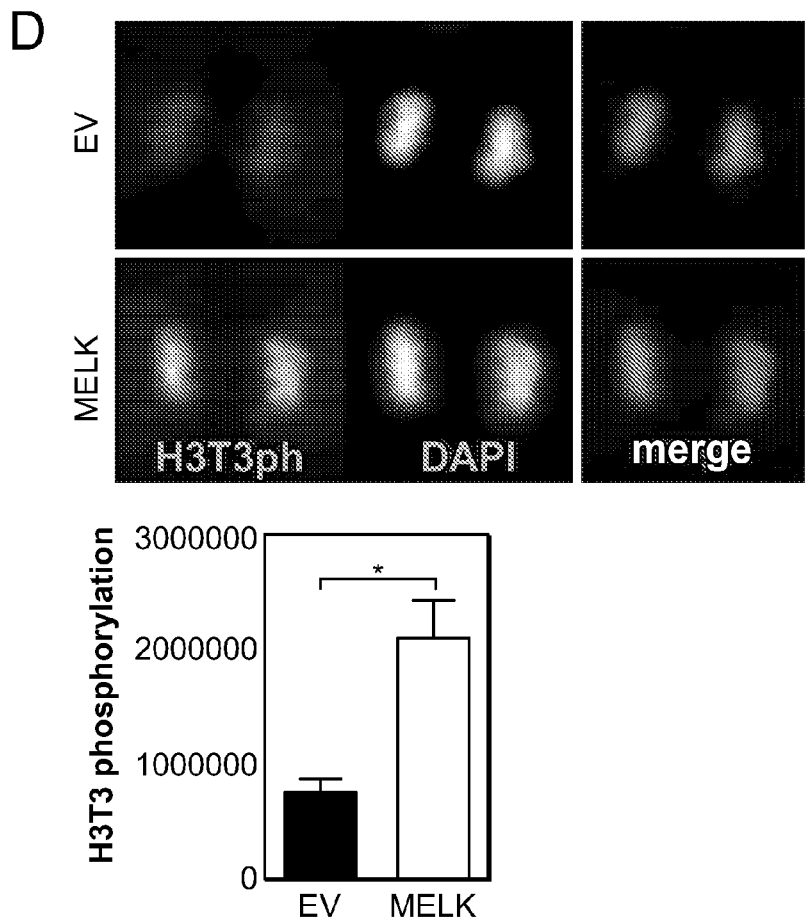
Figure 3:
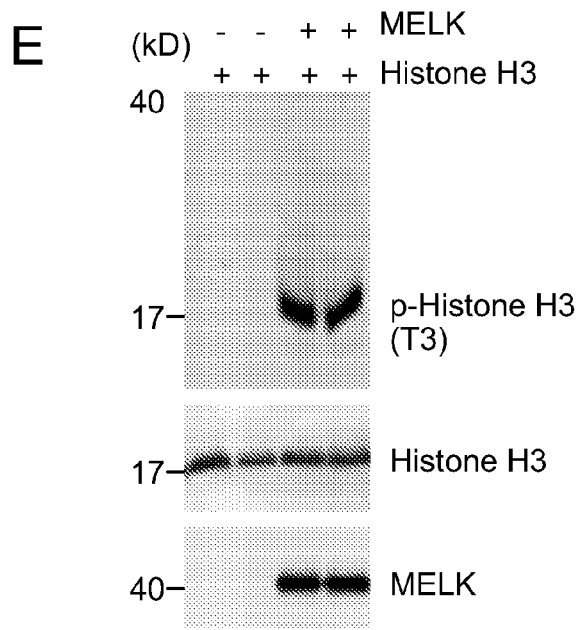
Figure 3:
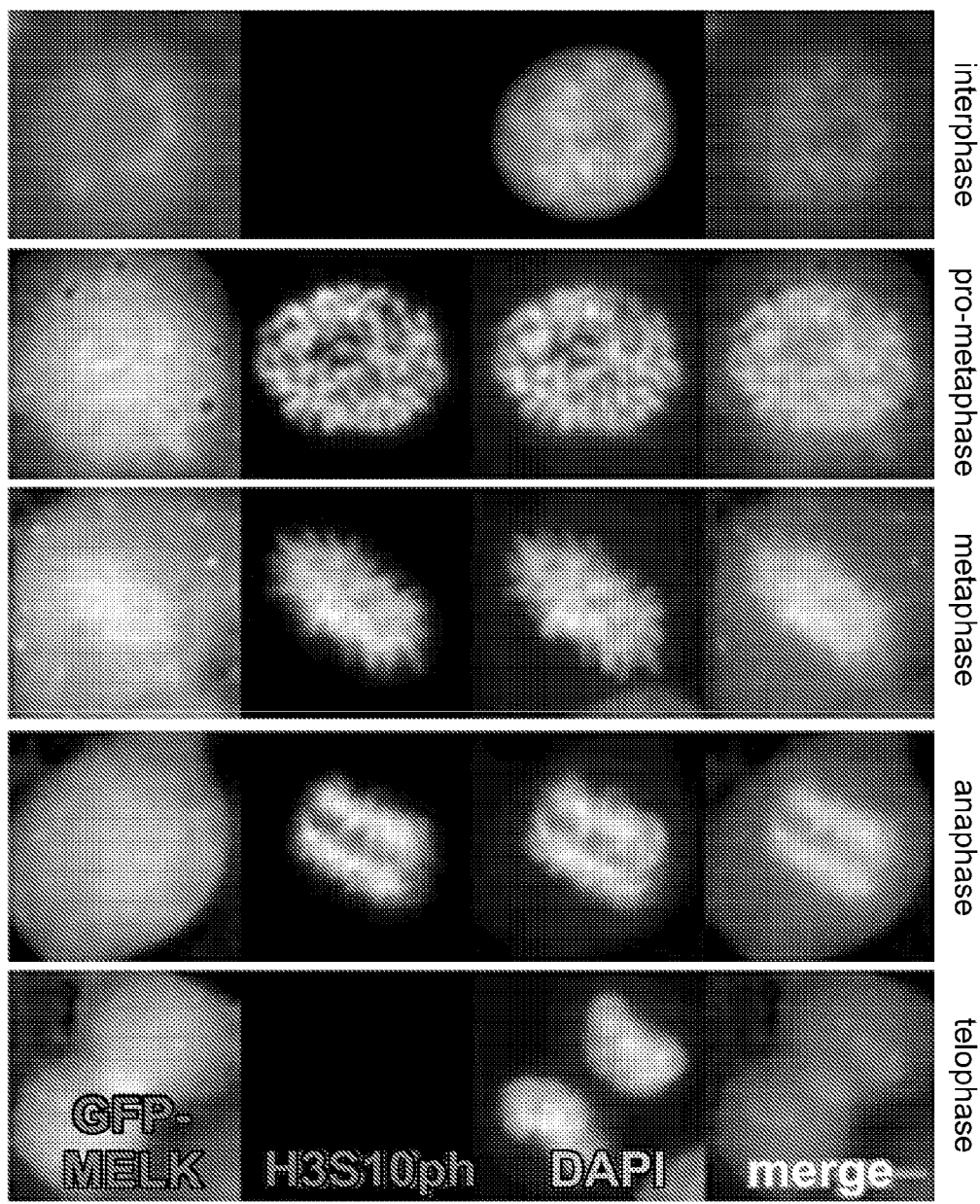
Figure 3:
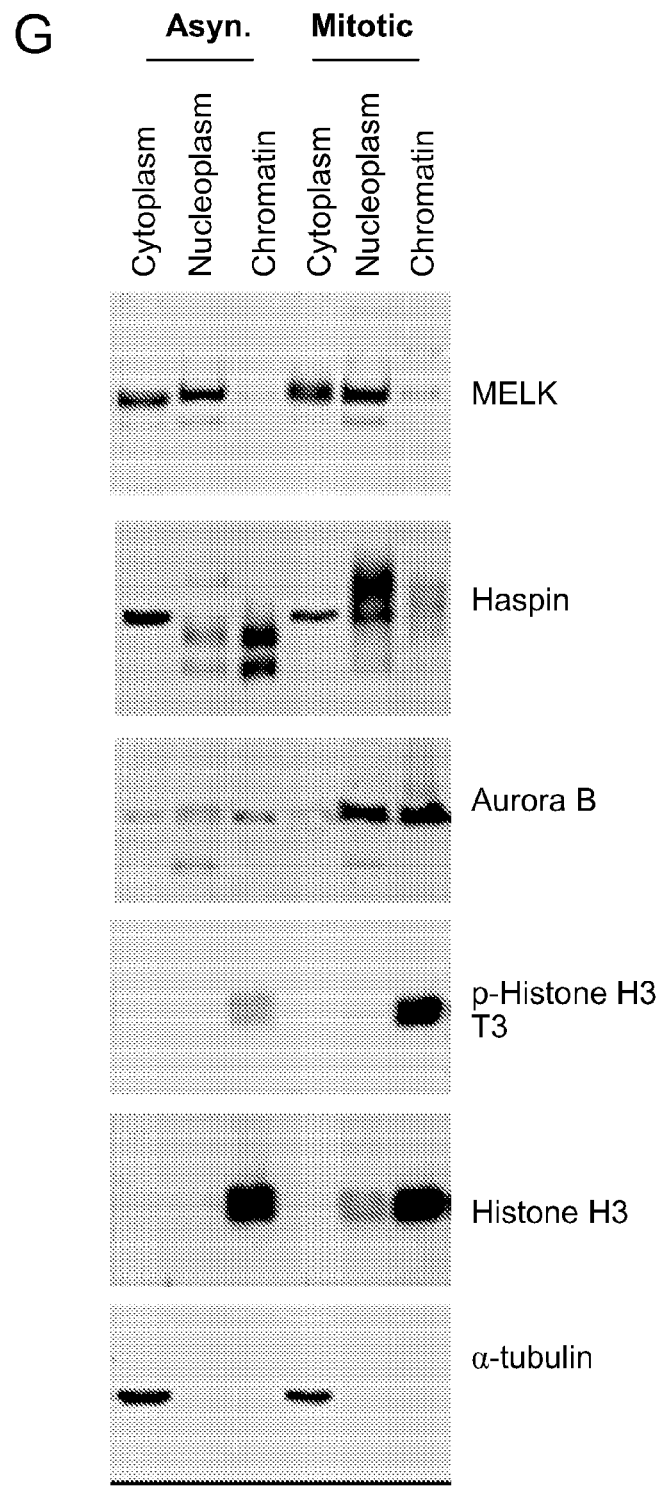
Figure 3:
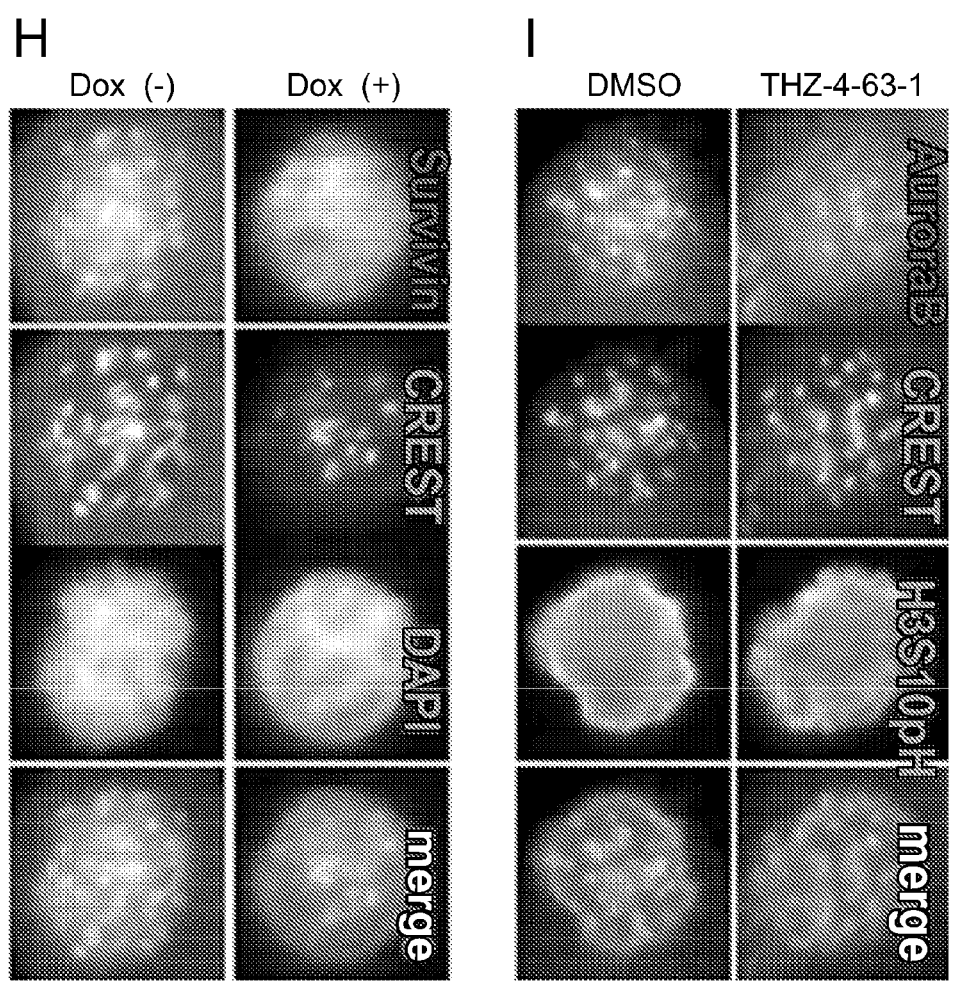
Figure 8:
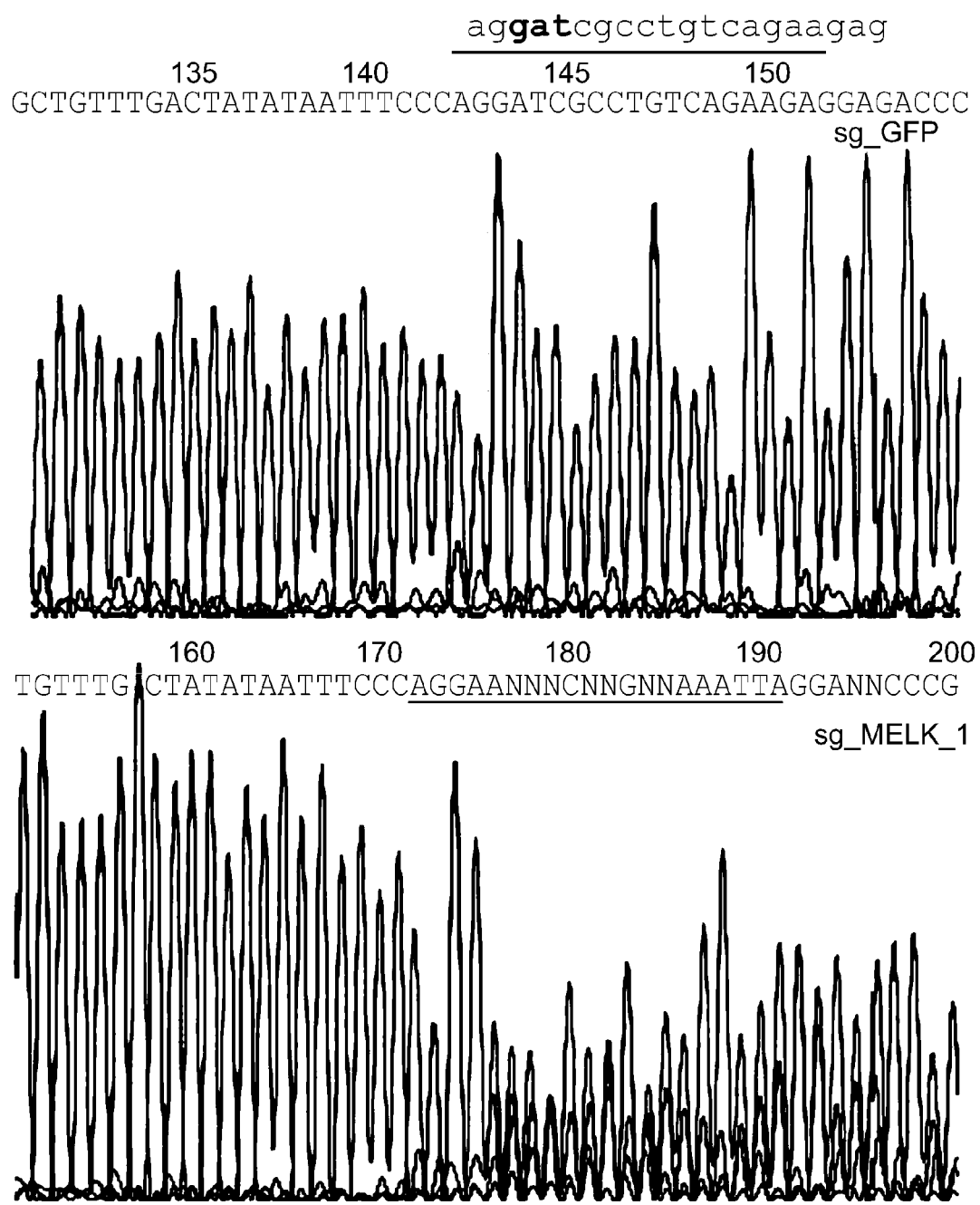
FIG. 8 presents data that establish that MELK depletion abolishes H3T3 phosphorylation in mitosis and consists of Panels A, B, and C. MDA-MB-468 cells were infected with virus encoding sgRNA targeting GFP (as a negative control) or MELK After puromycin selection, cells were seeded for harvest of genomic DNA, nocodazole-arrested mitotic cells for preparation of lysates. Panel A shows examination of MELK gene in cells infected with sg-MELK_1. Amplified DNA covering the exon 5 of MELK was subjected to sequencing. The region corresponding to the target of sgRNA (sequence shown) is highlighted with a line. Note that multiple different nucleotides can be found in DNA amplified from sg_MELK_1-infected cells. Panel A discloses SEQ ID NOS 1-3, respectively, in order of appearance. Panel B shows DpnII digestion of the amplified PCR products. sg_MELK_1 contains a DpnII site (depicted blue), rendering DpnII digestion as a way to measure the efficiency of gene editing. Panel B discloses SEQ ID NO: 1. Panel C shows immunoblotting of mitotic lysates using the indicated antibodies. Note that sg_MELK downregulates H3T3 phosphorylation, and does not influence of signaling of MAPK-mTOR.
Figure 8:
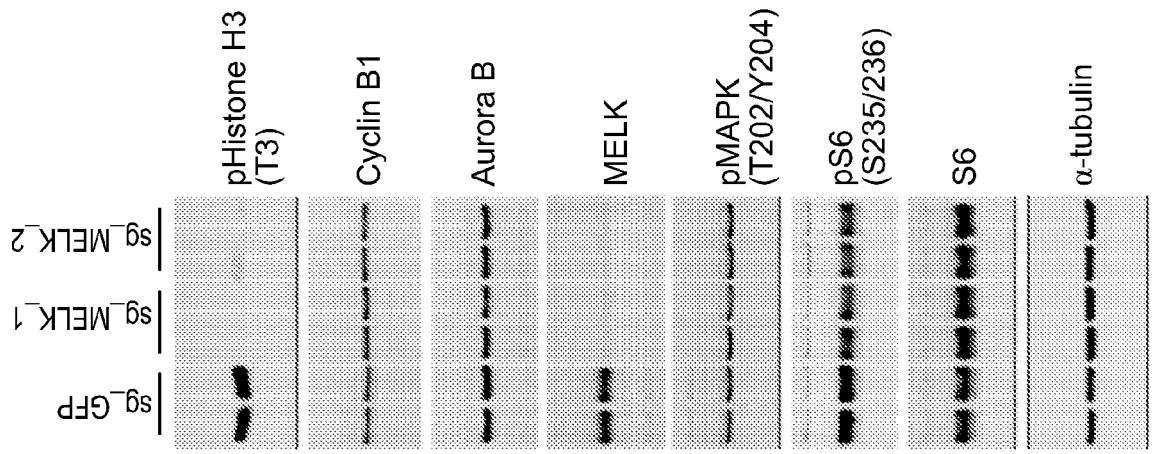
Figure 8:
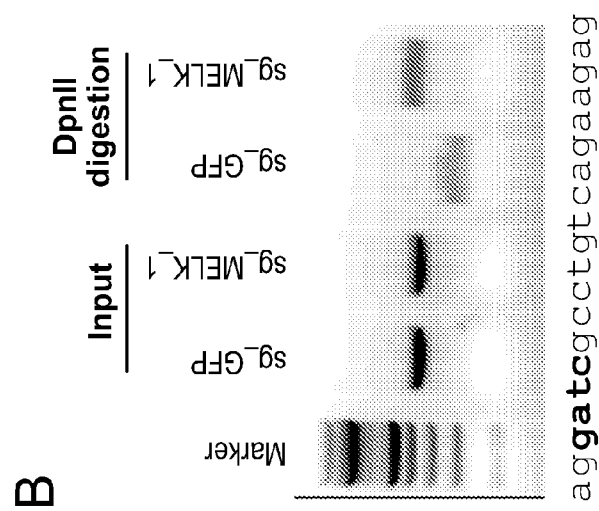

To understand how MELK inhibition influences chromosome alignment, we treated cells with THZ-4-63-1, or VX-680, an Aurora A/B/C inhibitor[11]. We exposed paclitaxel- or nocodazole-arrested mitotic cells to the individual inhibitor for 30 min in the presence of MG132, and collected lysates for examining signaling involved in chromosome alignment. As expected, VX-680 efficiently suppressed the auto-phosphorylation of Aurora kinases, and the phosphorylation of its direct substrate (Histone H3 at Ser10)[12,13] (FIGS. 3A, 8A). Recent studies unravel a novel role of Aurora B in phosphorylating Haspin[7], a major factor responsible for phosphorylating Histone H3 at Thr3[14]. Consistent with these findings, VX-680 treatment induced a potential de-phosphorylation of Haspin (suggested by an increased electrophoretic mobility of Haspin), and the inhibition of the downstream Histone H3 phosphorylation at Thr3 (FIG. 3A). By contrast, neither Aurora kinase nor Haspin phosphorylation was obviously impacted by THZ-4-63-1 (FIG. 3A, 7B-C), suggesting a potential Aurora-independent function of MELK. Surprisingly, MELK inhibition caused an strong suppression on Histone H3 phosphorylation at the residue of Thr3 (FIG. 3A, 7B-C). To further confirm such a paralleled action of MELK in regulating H3T3 phosphorylation, we treated cells with THZ-4-63-1 alone or combined with low dose of VX-680. We found that the presence of VX-680 did not apparently alter the potency of THZ-4-63-1 in inhibiting H3T3 phosphorylation (FIG. 7D). Together, these studies identify MELK as a novel signaling in regulating the phosphorylation of Histone H3, and that MELK likely acts in an Aurora-independent manner to promote H3T3 phosphorylation.

We further analyzed the impact of THZ-4-63-1 on H3T3 phosphorylation in individual cells by immunofluorescence assays. Similar to what we observed from cell population-based studies, MELK inhibition or knockdown induced a sufficient loss of H3T3 phosphorylation (FIG. 3B-C). In addition, overexpressing MELK in human mammary epithelial cells (MCF-10A), an untransformed line that expresses low level of endogenous MELK, significantly increased H3T3 phosphorylation in mitotic cells (FIG. 3D).

We also knocked down MELK expression via CRIPSR/Cas9-mediated genome editing[15]. Introducing a single lentiviral vector encoding both Cas9 and MELK-targeted sgRNA caused a robust alteration of the targeted region of MELK, indicated by both sequencing of amplified fragments and an altered sensitivity to restriction enzyme recognizing an endogenous site in the target sequence of MELK (FIG. 8A-B). Protein expression of MELK was efficiently decreased, as detected by an antibody that recognizes epitope on the N-terminus of MELK (FIG. 8C). In cells arrested at prometaphase by the treatment of nocodazole and MG132, sg_MELK resulted in an efficient suppression of H3T3 phosphorylation (FIG. 8C).

To investigate if MELK represents a kinase that directly phosphorylates Histone H3 at Thr3, we purified recombinant human MELK from insect cells, and subjected the protein to assay determining its in vitro activity towards phosphorylating recombinant Histone H3. Indeed, Histone H3 was robustly phosphorylated by MELK at Thr3 site (FIG. 3E). Together, these data based on the use of MELK inhibitor, knocking down or expressing MELK, and in vitro kinase activity study, propose MELK as a novel regulator of H3T3 phosphorylation, potentially acting as a direct kinase for H3T3.

Example 11

MELK Localizes in the Nucleus.

Since factors regulating Histone phosphorylation tend to localize either on or in the vicinity of chromosomes, we proceeded to characterize MELK by investigating its subcellular localization. In cells ectopically expressing fluorescent protein-tagged MELK (GFP-MELK), the fusion protein was mostly found in the nucleus during interphase (FIG. 3F, top row). In mitotic cells MELK tended to concentrate in the region of chromosomes, and on the contractile ring in telophase (FIG. 3F). We also determined the abundance of endogenous MELK in the fractions of cytosol, nucleoplasm, or chromatin in both asynchronized and mitotic cells. Consistent with the localization of GFP-MELK, endogenous MELK largely resides in nucleus, mostly in nucleoplasm (FIG. 3G). As expected, Auora B, a component of chromosome passenger complex (CPC), was readily recovered in the fraction of chromatin (FIG. 3G). Interestingly, endogenous Haspin, an recognized kinase phosphorylating H3T3[9], demonstrated a highly similar sub-cellular localization pattern as MELK, with most protein found in the nucleoplasm of mitotic cells (FIG. 3G). These data suggest that the MELK is largely residing in nucleus; and similar to Haspin, MELK might rely on a physical proximity with chromatin to phosphorylate Histone H3.

MELK Inhibition Alters the Localization of Chromosome Passenger Complex.

Figure 4:
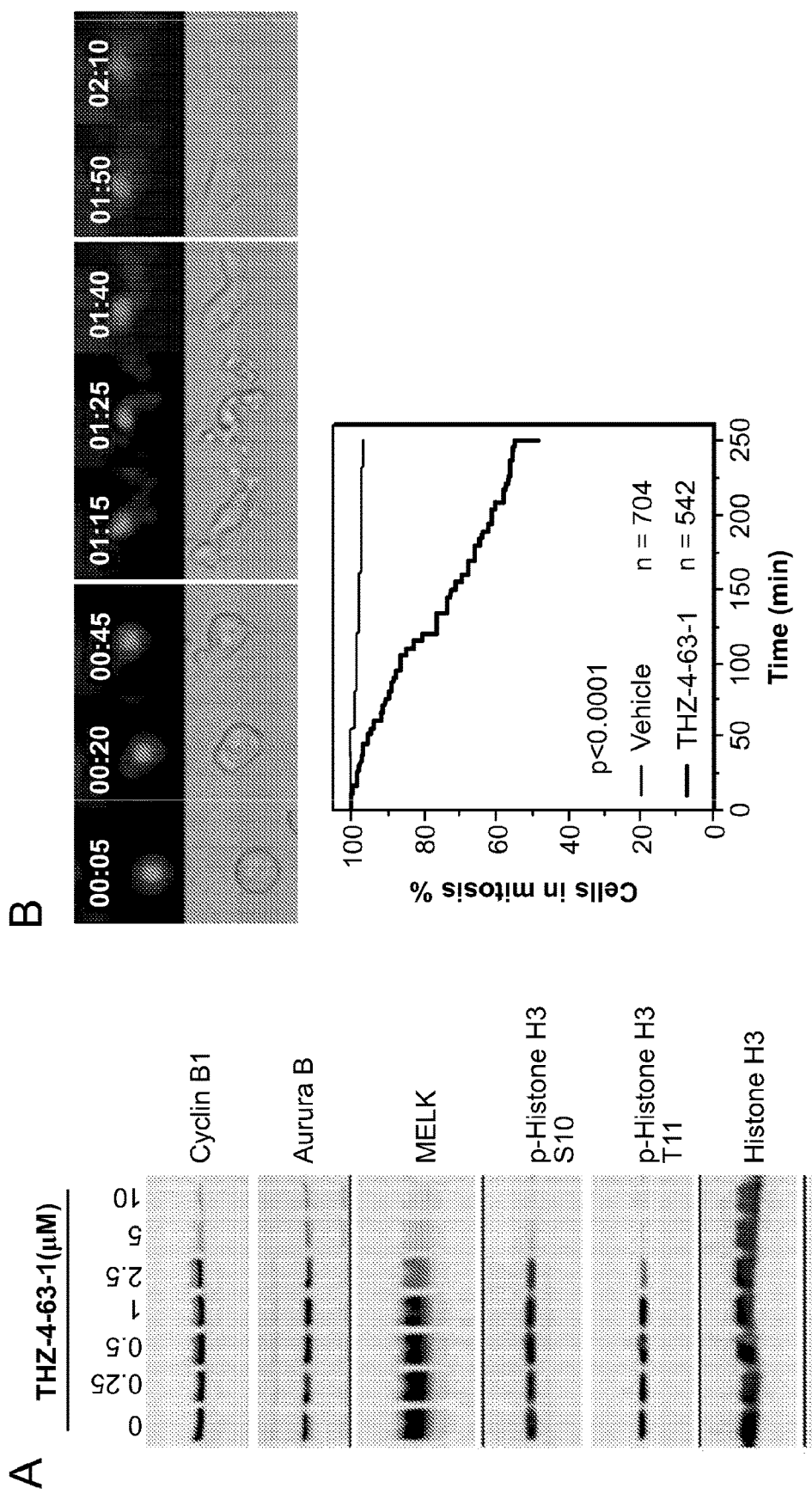
FIG. 4 consists of Panels A, B, C, D, and E, and demonstrates that MELK regulates mitotic checkpoint, and is essential for the growth of cancer cells. Panel A shows that THZ-4-63-1 inhibits spindle assembly checkpoint signaling in nocodazole-arrested cells. Mitotic cells were treated with THZ-4-63-1 at indicated concentrations for 4 h. Cells were collected for immunoblotting. Panel B contains time-lapse images of U2OS-(H2B-GFP) cells treated with THZ-4-63-1 (5 µM). The bottom shows the statistics of cells escaping mitosis. Panel C contains blots showing proteasome-mediated degradation of Cyclin B1, Aurora B and MELK in THZ-4-63-1-induced mitotic slippage. Mitotic cells were treated as in Panel A with THZ-4-63-1 (5 µM), or MG132 (10 µM), or both for 4 h. Panel D contains a graph showing quantification of cell proliferation in the indicated breast cancer cell lines, which were treated with vehicle control or THZ-4-63-1 for one week (Top) and also contains brightfield images acquired from control cells or cells treated with THZ-4-63-1 (111 nM) (Bottom). Panel E shows MELK inhibitions synergies with low dose of paclitaxel in suppressing tumor cell growth. Cells were treated with indicated drugs, and harvested in ten days for quantification of cell growth. The bold curve depicts the theoretic prediction of an additive action between paclitaxel and THZ-4-63-1.
Figure 4:
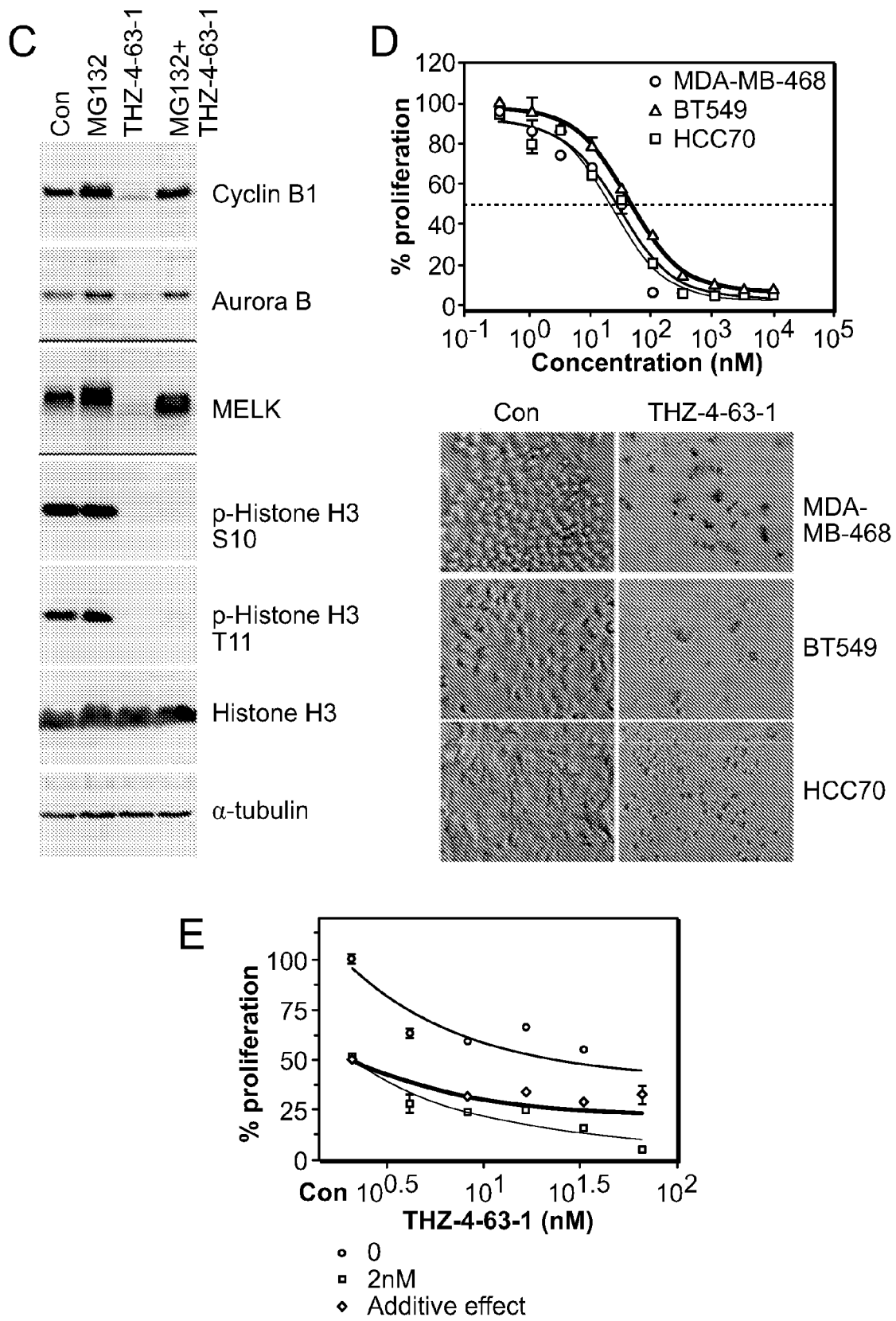

One of the roles of H3T3 phosphorylation is to, via binding to Survivin (a subunit of CPC), target CPC to centromeres[16-18]. We thus next investigated if MELK is required for the centromeric localization of CPC. In control cells, the CPC subunits, Survivin or Aurora B, showed a robust particle-like localization, which largely overlapped with centromere staining (FIG. 4G-H). By contrast, in cells with loss of MELK or treated with THZ-4-63-1, these CPC subunits became diffusive, indicating a defective targeting onto centromere (FIG. 4G-H).

Example 12

MELK is Required for Mitotic Checkpoint Signaling.

Figure 9:
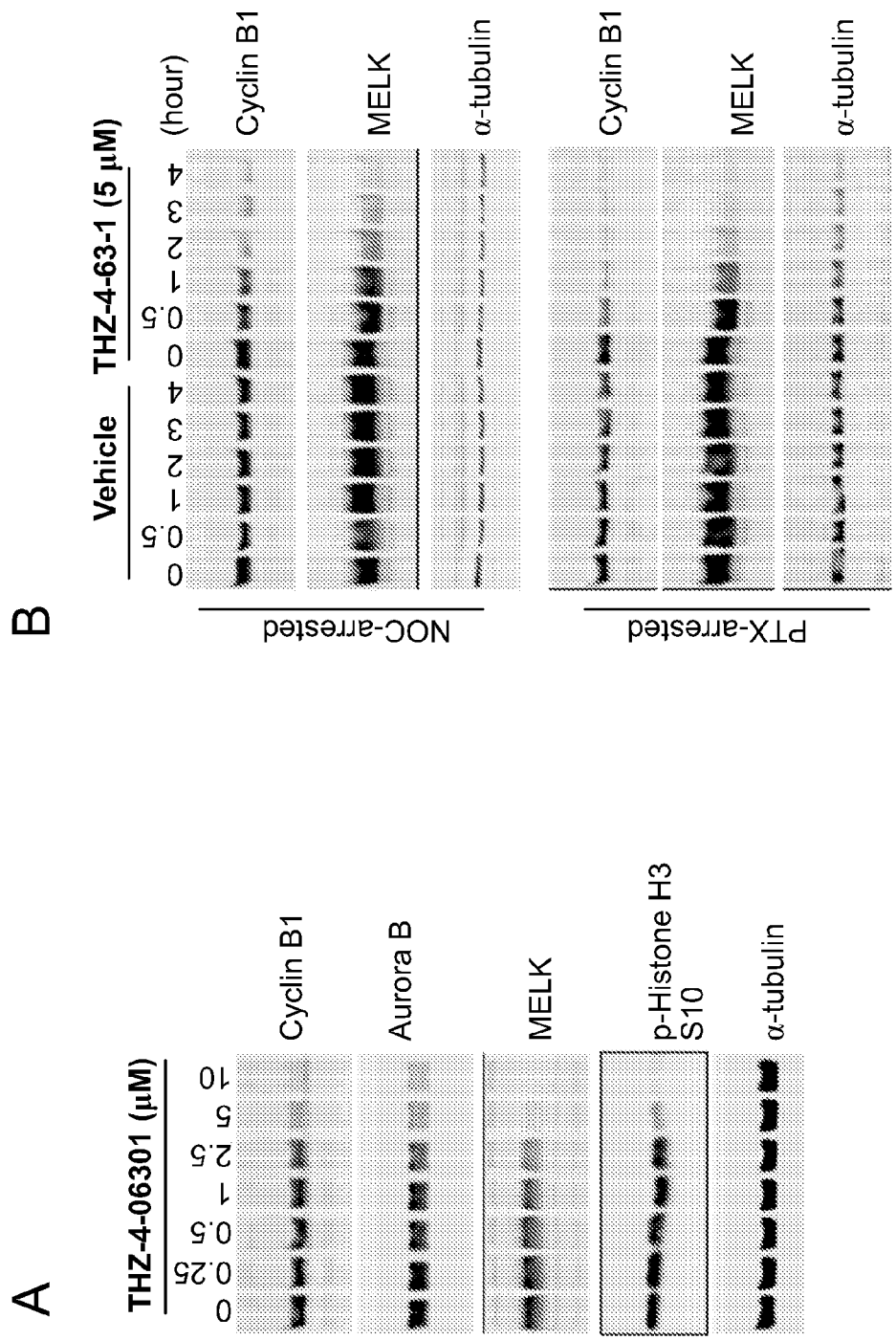
FIG. 9 contains images that show that MELK is required for spindle assembly checkpoint. In Panel A, paclitaxel-arrested cells were treated with THZ-4-63-1 at indicated concentrations for 4 h. Cells were collected for immunoblotting. In Panel B, nocodazole- (top) or paclitaxel-arrested mitotic cells were treated with vehicle control or THZ-4-63-1 (5 µM) for increasing time. Cell lysates were collected for immunoblotting. In Panel C, proteasome-mediated degradation of Cyclin B1, Aurora B and MELK in THZ-4-63-1-induced mitotic slippage. Mitotic cells were treated as in Panel A with THZ-4-63-1 (5 µM), or MG132 (10 µM), or both for 4 h. In Panel D, siRNA-mediating MELK knockdown impairs spindle checkpoint assembly. HeLa cells were transfected with control or MELK-targeted siRNA. Two days after transfection, cells were treated with nocodazole to activate spindle assembly checkpoint. (Top) representative brightfield images of cells following 20 hours of nocodazole treatment. (Middle) DAPI staining of the cells, scale bar is 10 µm. (Bottom) immunblotting showing the knockdown efficiency.
Figure 9:
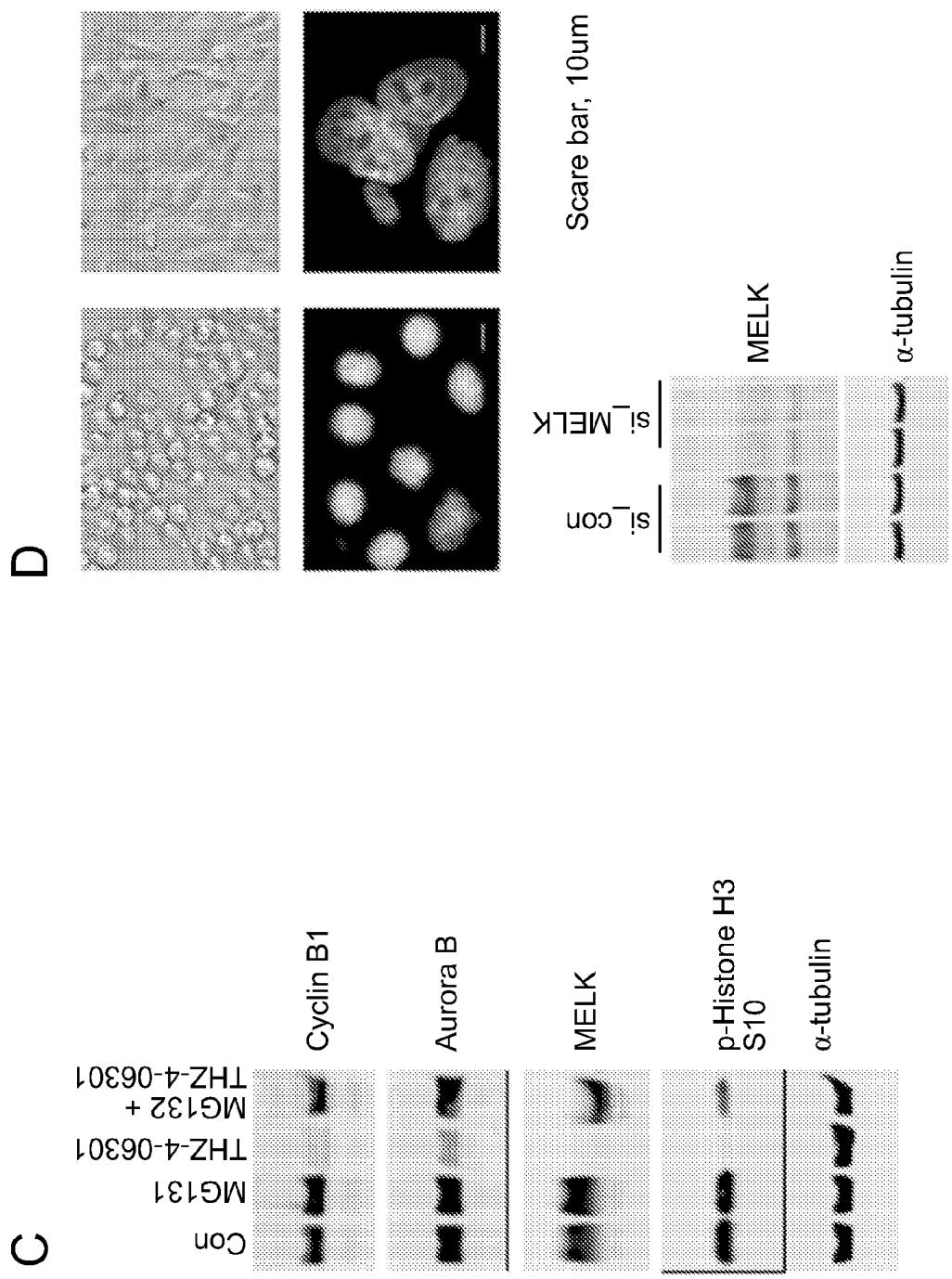

Centromeric localization of CPC has been implicated in checkpoint signaling[8]. Since we found that MELK is important for the generation of H3T3 phosphorylation and the docking of CPC onto kinetochore, we asked if MELK also regulates mitotic checkpoint. In cells arrested at prometaphase by treatment of either nocodazole or paclitaxel, THZ-4-63-1 was applied, and cell lysates were used to determine the abundance of mitotic factors including Cyclin B1, MELK, and Aurora B. MELK inhibition efficiently reduced the protein amount of these mitotic factors, in a time- and dose-dependent manner (FIGS. 4A, 9A-B), indicating an induction of mitotic slippage. We also imaged cells expressing GFP-H2B, and found that nearly half of cells underwent mitotic slippage after 4 h exposure to THZ-4-63-1 (FIG. 4B). We further found an impaired spindle checkpoint in cells with MELK knockdown (FIG. 9C). Together, these data suggest MELK as a novel regulator of the spindle checkpoint.

We also asked if inhibiting the degradation of mitotic factors including Cyclin B1, MELK and Aurora kinases, would rescue the otherwise abrogated checkpoint. Toward this purpose, we treated cells with THZ-4-63-1 or MG132 individually, or combined. As expected, MG132 treatment restored the protein abundance of these mitotic factors in the presence of THZ-4-63-1 (FIGS. 4C, 9C). However, mitotic slippage induced by the inhibitor was not rescued by MG132, indicated by the phosphorylation of Histone H3 at S10 and T11, two markers of mitosis. Therefore, it is the activity of MELK rather than the protein itself that is crucial for maintaining the spindle assembly checkpoint.

Example 13

THZ-4-63-1 Inhibits the Growth of Tumor Cells.

We previously proposed MELK as a drug target for basal breast cancer, which demonstrate dramatic overexpression of MELK[2]. With the identification of a selective MELK inhibitor, we next tested if THZ-4-63-1 is an effective agent for those cancer cells. As expected, THZ-4-63-1 potently inhibited the proliferation of basal breast cancer cells, with an IC50 of approximating 50 nM; and low nanomolar dose of THZ-4-63-1 caused a nearly complete cell death (FIG. 4D). The high potency of THZ-4-63-1 not only confirm the previous identification of MELK as an essential kinase for breast cancer, but also poise the compound itself for immediate translational implications.

Because microtubule-targeting chemotherapy is the mainstay of treatment for many types of cancer including basal-like breast cancer, we asked if MELK inhibition could combine with drugs that impair microtubule dynamics. Notably, a recent study finds that partially knocking down mitotic factors involved in both checkpoint signaling and chromosome alignment, remarkably synergies with lose doses of paclitaxel, causing apparent growth inhibition in cancer cells[19]. We treated basal breast cancer cell, MDA-MB-468 with increasing concentration of THZ-4-63-1 (0-50 nM) in the absence of presence of paclitaxel at a clinically relevant dose (2 nM). The treatment of paclitaxel alone led a half reduction of cell proliferation; and when combined with THZ-4-63-1 (33.3 or 66.6 nM) caused a significant synergistic effect with 80% or more inhibition (FIG. 4E).

In this study we reported the discovery of a novel small inhibitor MELK, and after demonstrating its selective action, utilized this tool for exploiting functions of MELK in mitosis. Our investigation based on the use of THZ-4-63-1, combined with approaches to genetically interfere MELK expression, has led to novel findings that (a) MELK is important for metaphase chromosome alignment; (b) MELK is a previously unrecognized kinase regulating spindle assembly checkpoint; (c) MELK is a novel kinase for the Thr3 site of Histone H3, and is required for the recruitment of chromosomal passenger complex to centromere.

Our study adds new insights into how H3T3 phosphorylation is regulated. Previous studies clearly demonstrate Haspin as one such kinase for H3T3. However, Haspin depletion causes defects in mitotic checkpoint that is much less prominent than what is observed in cells with dysfunctions in chromosomal passenger complex (ref), suggesting a possible existence of another paralleled pathway regulating H3T3 phosphorylation and the localization of chromosomal passenger complex. Our studies suggest that MELK, the novel kinase for H3T3 phosphorylation, act in a way that is likely independent of Aurora B, because (a) MELK inhibition does not impair the auto-phosphorylation of Aurora kinases or Haspin; (b) The auto-phosphorylation status of MELK is insensitive to the inhibition of Aurora kinases. These intriguing observations also lead to a number of questions such as how MELK activity is regulated in mitosis, whether MELK is constitutively active during mitosis, and if and how MELK co-ordinates with other kinase such as Haspin in phosphorylating H3T3. Despite these unresolved questions, the high potency of THZ-4-63-1, together with previous findings that MELK is an oncogenic target, makes this novel compound a candidate with a potential to be readily translated to an expected clinical efficacy in treating cancer patients.

REFERENCES

1. Badouel, C., Chartrain, I., Blot, J., & Tassan, J. P. (2010). Maternal embryonic leucine zipper kinase is stabilized in mitosis by phosphorylation and is partially degraded upon mitotic exit. *Experimental cell research*, 316(13), 2166-2173.
2. Wang, Y., et al. (2014). MELK is an oncogenic kinase essential for mitotic progression in basal-like breast cancer cells. *eLife*, e01763-e01763.
3. Le Page, Y., Chartrain, I., Badouel, C., & Tassan, J. P. (2011). A functional analysis of MELK in cell division reveals a transition in the mode of cytokinesis during Xenopus development. *Journal of cell science*, 124(6), 958-968.
4. Davezac, N., Baldin, V., Blot, J., Ducommun, B., & Tassan, J. P. (2002). Human pEg3 kinase associates with and phosphorylates CDC25B phosphatase: a potential role for pEg3 in cell cycle regulation. *Oncogene*, 21(50), 7630-7641.
5. Liu, Q., et al. (2010). Discovery of 1-(4-(4-propionylpiperazin-1-yl)-3-(trifluoromethyl) phenyl)-9-(quinolin-3-yl) benzo [h][1, 6] naphthyridin-2 (1H)-one as a highly potent, selective mammalian target of rapamycin (mTOR) inhibitor for the treatment of cancer. *Journal of medicinal chemistry*, 55(19), 7146-7155.
6. Liu, Q., et al. (2011). Discovery of 9-(6-Aminopyridin-3-yl)-1-(3-(trifluoromethyl) phenyl) benzo [h][1, 6] naphthyridin-2 (1H)-one (Torin2) as a Potent, Selective, and Orally Available Mammalian Target of Rapamycin (mTOR) Inhibitor for Treatment of Cancer. *Journal of medicinal chemistry*, 54(5), 1473-1480.
7. Kanda, T., Sullivan, K. F., & Wahl, G. M. (1998). Histone-GFP fusion protein enables sensitive analysis of chromosome dynamics in living mammalian cells. *Current Biology*, 8(7), 377-385.
8. Carmena, M., Wheelock, M., Funabiki, H., & Earnshaw, W. C. (2012). The chromosomal passenger complex (CPC): from easy rider to the godfather of mitosis. *Nature reviews Molecular cell biology*, 13(12), 789-803.
9. Dai, J., Sultan, S., Taylor, S. S., & Higgins, J. M. (2005). The kinase haspin is required for mitotic histone H3 Thr 3 phosphorylation and normal metaphase chromosome alignment. *Genes & development*, 19(4), 472-488.
10. Dai, J., & Higgins, J. M. (2005). Haspin: a mitotic histone kinase required for metaphase chromosome alignment. *Cell cycle*, 4(5), 665-668.
11. Harrington, E. A., et al. (2004). VX-680, a potent and selective small-molecule inhibitor of the Aurora kinases, suppresses tumor growth in vivo. *Nature medicine*, 10(3), 262-267.
12. Hsu, J. Y., et al. (2000). Mitotic phosphorylation of histone H3 is governed by Ipl1/aurora kinase and Glc7/PP1 phosphatase in budding yeast and nematodes. *Cell*, 102(3), 279-291.
13. Giet, R., & Glover, D. M. (2001). Drosophila aurora B kinase is required for histone H3 phosphorylation and condensin recruitment during chromosome condensation and to organize the central spindle during cytokinesis. *The Journal of cell biology*, 152(4), 669-682.
14. Wang, F., Ulyanova, N. P., van der Waal, M. S., Patnaik, D., Lens, S., & Higgins, J. M. (2011). A positive feedback loop involving Haspin and Aurora B promotes CPC accumulation at centromeres in mitosis. *Current Biology*, 21(2), 1061-1069.
15. Shalem, O., et al. (2014). Genome-scale CRISPR-Cas9 knockout screening in human cells. *Science*, 343(6166), 84-87.
16. Kelly, A. E., et al. (2010). Survivin reads phosphorylated histone H3 threonine 3 to activate the mitotic kinase Aurora B. *Science*, 330(6001), 235-239
17. Wang, F., et al. (2010). Histone H3 Thr-3 phosphorylation by Haspin positions Aurora B at centromeres in mitosis. *Science*, 330(6001), 231-235.
18. Yamagishi, Y., Honda, T., Tanno, Y., & Watanabe, Y. (2010). Two histone marks establish the inner centromere and chromosome bi-orientation. *Science*, 330(6001), 239-243.
19. Janssen, A., Kops, G. J., & Medema, R. H. (2009). Elevating the frequency of chromosome mis-segregation as a strategy to kill tumor cells. *Proceedings of the National Academy of Sciences*, 106(45), 19108-19113.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A compound represented by formula (IV) or a pharmaceutically acceptable salt thereof:

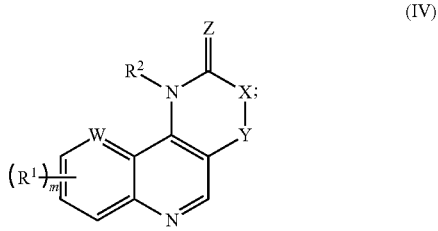

(IV)

wherein:

Z represents O, S, NH, or N(alkyl);

—X—Y— represents —CR$^3$=CR$^4$— or —CHR$^3$—CHR$^4$—;

R$^1$, independently for each occurrence, represents aryl, substituted by at least three occurrences of substituent R$^x$;

R$^x$, independently for each occurrence, is selected from the group consisting of halo, (C$_1$-C$_6$)alkyl, (C$_1$-C$_6$)alkenyl, (C$_1$-C$_6$)alkynyl, (C$_1$-C$_6$)haloalkyl, aryl, —OH, (C$_3$-C$_6$)cycloalkyl, (C$_1$-C$_6$)alkoxyl, (C$_1$-C$_6$)haloalkoxyl, —SH, —S((C$_1$-C$_6$)alkyl), (C$_1$-C$_6$)hydroxyalkyl, (C$_1$-C$_6$)alkoxy(C$_1$-C$_6$)alkyl, —CN, —CF$_3$, —NO$_2$, —NH$_2$, —NH(R$^6$), —N(R$^6$)$_2$, (C$_1$-C$_6$)alkyl substituted by —N(R$^6$)$_2$, —C(O)NH$_2$, —C(O)NH(R$^6$), —C(O)N(R$^6$)$_2$, —N(H)C(O)(R$^6$), —N(R$^6$)C(O)(R$^6$), —S(O)$_2$NH$_2$, —S(O)$_2$NH(R$^6$), —S(O)$_2$N(R$^6$)$_2$, —N(H)S(O)$_2$(R$^6$), and —N(R$^6$)S(O)$_2$(R$^6$);

wherein at least one occurrence of $R^x$ is OH;

$R^2$ represents aryl, aralkyl, heteroaryl, heteroaralkyl, cycloalkyl, cycloalkylalkyl, heterocycloalkyl, or heterocycloalkylalkyl, optionally substituted by one or more occurrences of substituent $R^5$;

$R^3$ and $R^4$ are each independently selected from the group consisting of H, alkyl, aralkyl, and aryl;

$R^5$, independently for each occurrence, is selected from the group consisting of substituted or unsubstituted alkyl, alkenyl, alkynyl, halo, haloalkyl, alkoxyl, amino, aminoalkyl, hydroxy, hydroxyalkyl, aryl, aryloxy, arylalkoxy, heteroaryl, heteroaryloxy, heteroarylalkoxy, cyano, nitro, cycloalkyl, and heterocycloalkyl;

$R^6$, independently for each occurrence, is selected from the group consisting of $(C_1-C_6)$alkyl, aryl, and aryl$(C_1-C_6)$alkyl, or, for —$N(R^6)_2$, —$C(O)N(R^6)_2$, and —$S(O)_2$ $N(R^6)_2$, or two occurrences of $R^6$, together with the nitrogen atom to which they are attached can be taken together to form an optionally substituted ring;

W represents N, CH, or $CR^1$; and m is an integer from 1-3.

2. The compound of claim 1, wherein —X—Y— is —CH=CH—.

3. The compound of claim 1, represented by formula (IVa):

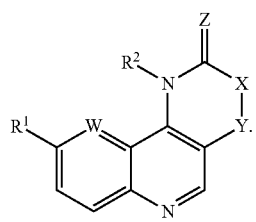

(IVa)

4. The compound of claim 1, wherein $R^2$ is substituted by one or more occurrences of substituent $R^5$, wherein at least one occurrence of $R^5$ is amino or aminoalkyl.

5. The compound of claim 1, represented by formula (V),

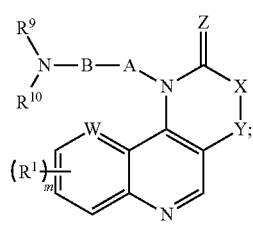

(V)

wherein:

A represents 1,4-cyclohexanediyl, 1,3-cyclohexanediyl, 1,2-cyclohexanediyl, 1,4-phenylene, 1,4-cycloheptanediyl, 1,3-cycloheptanediyl, 1,3-cyclooctanediyl, 1,4-cyclooctanediyl, 1,5-cyclooctanediyl;

B represents $(C_1-C_6)$alkylene or a bond; and $R^9$ and $R^{10}$ are each independently selected from the group consisting of H, $(C_1-C_6)$alkyl, aryl, and aryl$(C_1-C_6)$alkyl, or, $R^9$ and $R^{10}$, together with the nitrogen atom to which they are attached can be taken together to form an optionally substituted heterocyclic ring.

6. The compound of claim 1, represented by any one of the following formulae:

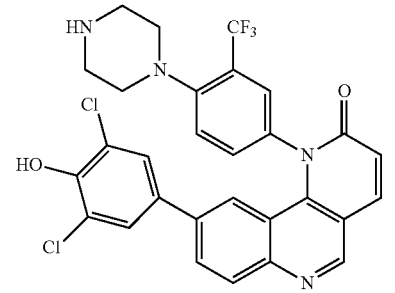

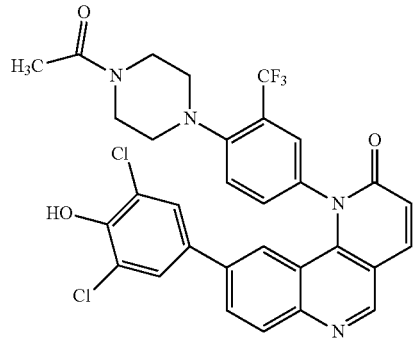

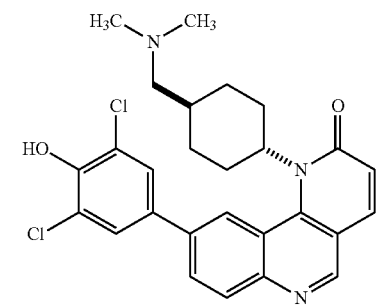

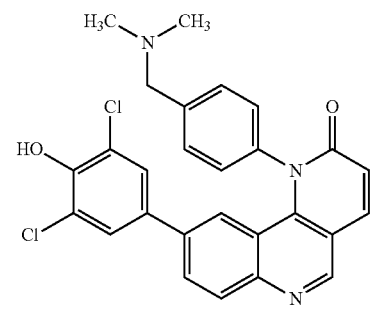

7. A method of treating cancer, comprising administering to a subject in need thereof a therapeutically effective amount of a compound of claim 1.

8. The method of claim 7, wherein the cancer is associated with overexpression of MELK.

9. A method of inhibiting maternal embryonic leucine zipper kinase (MELK), comprising contacting MELK with an amount of a compound of claim 1 effective to inhibit MELK.

10. A method for treating or preventing a condition associated with aberrant maternal embryonic leucine zipper kinase (MELK), comprising administering to a subject in need thereof a therapeutically effective amount of a compound of claim 1.

11. A method for decreasing the rate of mitosis in a cancer cell, comprising contacting a cancer cell with an amount of a compound of claim 1 effective to decrease the rate of mitosis of the cancer cell.

12. A pharmaceutical composition comprising a compound of claim 1, and a pharmaceutically acceptable carrier.

13. The compound of claim 1, wherein Z is O.

14. The compound of claim 1, wherein W is N.

15. The compound of claim 1, wherein W is CH.

16. The compound of claim 1, wherein each occurrence of $R^x$ is independently selected from the group consisting of $(C_1\text{-}C_6)$alkyl, $(C_1\text{-}C_6)$alkoxy, $(C_1\text{-}C_6)$haloalkyl, halo, —OH, $(C_1\text{-}C_6)$haloalkoxyl, —SH, —S$((C_1\text{-}C_6)$alkyl$)$, $(C_1\text{-}C_6)$hydroxyalkyl, and —CF$_3$.

17. The compound of claim 1, wherein each occurrence of $R^x$ is independently selected from the group consisting of $(C_1\text{-}C_6)$haloalkyl, halo, —OH, $(C_1\text{-}C_6)$hydroxyalkyl, and —CF$_3$.

18. The compound of claim 1, wherein $R^1$ represents

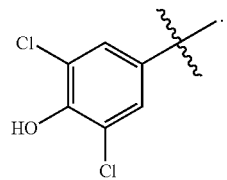

19. The compound of claim 1, wherein m is 1.

20. The compound of claim 3, wherein $R^2$ represents aryl, aralkyl, cycloalkyl, cycloalkylalkyl, heterocycloalkyl, or heterocycloalkylalkyl, optionally substituted by one or more occurrences of substituent $R^5$;

wherein $R^5$, independently for each occurrence, is selected from the group consisting of substituted or unsubstituted alkyl, halo, haloalkyl, amino, aminoalkyl, heteroaryl, heteroaryloxy, and heterocycloalkyl.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Unknown
<220> FEATURE:
<223> OTHER INFORMATION: Description of Unknown: MELK sequence

<400> SEQUENCE: 1
aggatcgcct gtcagaagag                                          20

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
gctgtttgac tatataattt cccaggatcg cctgtcagaa gaggagaccc          50

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (20)..(22)
<223> OTHER INFORMATION: a, c, t, g, unknown or other
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: modified_base
<222> LOCATION: (27)..(28)
<223> OTHER INFORMATION: a, c, t, g, unknown or other
<220> FEATURE:
<221> NAME/KEY: modified_base
<222> LOCATION: (38)..(39)
<223> OTHER INFORMATION: a, c, t, g, unknown or other

<400> SEQUENCE: 3
ctatataatt tcccaggaan nncnngnnaa attaggannc ccg                 43